US007094571B2

(12) United States Patent
Harvey et al.

(10) Patent No.: US 7,094,571 B2
(45) Date of Patent: *Aug. 22, 2006

(54) COMBINATORIAL PROTEIN LIBRARY SCREENING BY PERIPLASMIC EXPRESSION

(75) Inventors: Barrett R. Harvey, Austin, TX (US); George Georgiou, Austin, TX (US); Brent L. Iverson, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/620,278

(22) Filed: Jul. 15, 2003

(65) Prior Publication Data

US 2004/0058403 A1    Mar. 25, 2004

Related U.S. Application Data

(63) Continuation-in-part of application No. 09/699,023, filed on Oct. 27, 2000.

(60) Provisional application No. 60/396,058, filed on Jul. 15, 2002.

(51) Int. Cl.
| | |
|---|---|
| C12P 21/06 | (2006.01) |
| C12P 21/04 | (2006.01) |
| C12N 15/09 | (2006.01) |
| G01N 33/53 | (2006.01) |

(52) U.S. Cl. .................. 435/69.1; 435/69.2; 435/69.3; 435/69.7; 435/7.1

(58) Field of Classification Search ............... 435/7.32, 435/7.21, 7.1, 69.7, 69.1, 69.2, 69.3, 69.9
See application file for complete search history.

(56) References Cited

U.S. PATENT DOCUMENTS

| | | | |
|---|---|---|---|
| 5,233,409 A | 8/1993 | Schwab | ...................... 356/402 |
| 5,571,698 A | 11/1996 | Ladner et al. | .............. 435/69.7 |
| 5,780,279 A | 7/1998 | Matthews et al. | ........ 435/172.3 |
| 5,824,520 A | 10/1998 | Mulligan-Kehoe | ....... 435/91.41 |
| 5,837,500 A | 11/1998 | Ladner et al. | .............. 435/69.7 |
| 5,922,545 A | 7/1999 | Mattheakis et al. | ............. 435/6 |
| 6,001,823 A * | 12/1999 | Hultgren et al. | ............... 514/99 |

FOREIGN PATENT DOCUMENTS

| | | | |
|---|---|---|---|
| WO | WO 98/49286 | * | 11/1998 |

OTHER PUBLICATIONS

Thomas E. Creighton, in his book, "Proteins: Structures and Molecular Properties, 1984", (p. 315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Ames (Journal of Bioenergetics and Biomembranes, Feb., 1988, 20(1) 1-17).*
Decad et al, (Journal of Bacteriology, Oct. 1976, 128(1):325-36).*
Nakae et al (The Journal of Biological Chemistry, Vo. 250, No. 18, Sep. 1975).*
Higgins et al (Journal of Bioenergetics and Biomembranes, vol. 22., No. 4, 1990).*
Webster's Ninth New Collegiate Dictionary, 1990.*
Staudenmaier et al (Journal of Bacteriology, May 1989, p. 2626-2633).*
Ames (Journal of Bioenergetics and Biomembranes, Feb., 1988, 20(1) 1-18).*
Nakae et al (The Journal of Biological Chemistry, vol. 250, No. 18, Sep. 1975).*
Nosoh, Y. et al in "Protein Stability and Stabilization through Protein Engineering, 1991".*
Thomas E. Creighton, in his book."Protein Structure: A Practical Approach, 1989; pp. 184-186".*
Thomas E. Creighton, in his book, "Proteins: Structures and Molecular Properties, 1984", (pp. 314-315).*
Boder et al., "Directed evolution of antibody fragments with monovalent femtomolar antigen-binding affinity," *Proc. Natl. Acad. Sci. USA*, 97(20):10701-10705, 2000.
Burioni et al., "A new supbraction technique for molecular cloning or rare antiviral antibody specificities from phage display libraries," *Res. Virol.*, 149:327-330, 1998.
Burman et al., *J. Bacteriol.*, "Murein and the outer penetration barrier of *Escheriachia coli* K-12, *Proteus mirabilis*, and *Pseudomonas aeruginosa*," Journal of Bacteriology, 112(3):1364-1374, 1972.
Chen et al., "Selection and analysis of an optimized anti-VEGF antibody: crystal structure of an affinity-matured Fab in complex with antigen," *J. Mol. Biol.*, 293:865, 1999.

(Continued)

*Primary Examiner*—Lynette R. F. Smith
*Assistant Examiner*—Vanessa L. Ford
(74) *Attorney, Agent, or Firm*—Fulbright & Jaworski L.L.P.

(57) ABSTRACT

The invention overcomes the deficiencies of the prior art by providing a rapid approach for isolating binding proteins capable of binding small molecules and peptides. In the technique, libraries of candidate binding proteins, such as antibody sequences, are expressed in the periplasm of gram negative bacteria and mixed with a labeled ligand. In clones expressing recombinant polypeptides with affinity for the ligand, the concentration of the labeled ligand bound to the binding protein is increased and allows the cells to be isolated from the rest of the library. Where fluorescent labeling of the target ligand is used, cells may be isolated by fluorescence activated cell sorting (FACS). The approach is more rapid than prior art methods and avoids problems associated with the outer surface-expression of ligand fusion proteins employed with phage display.

48 Claims, 10 Drawing Sheets

OTHER PUBLICATIONS

Chen et al., *Nat. Biotechnol.*, "Isolation of high-affinity ligand-binding proteins by periplasmic expression with cytometric screening (PECS)," 19(6):537-542, 2001.

Chen et al., "In vitro scanning saturation mutagenesis of all the specificity determining residues in an antibody binding site," *Protein Eng.*, 12(4):349-356, 1999.

Chowdhury and Pastan, "Improving antibody baffinity by mimicking somatic hypermutation in vitro," *Nat. Biotech.*, 17:568, 1999.

Coia et al., "Use of mutator cells as a means for increasing production levels of a recobinant antibody directed against Hepititis B," *Gene*, 201:203, 1997.

Corey et al., "Trypsin display on the surface of bacteriophage," *Gene*, 128:129, 1993.

Dall'Aqua and Carter, "Antibody engineering," *Curr. Opin. Struct. Biol.*, 8:443, 1998.

Daugherty et al., "Flow cytometric screening of cell-based libraries," *J. Immunol. Methods*, 243:211, 2000.

Daugherty et al., "Quantitative analysis of the effect of the mutation frequency on the affinity maturation of single chain Fv antibodies," *Proc. Natl. Acd. Sci. USA*, 97:2029-2034, 2000.

Daugherty et al., "Development of an optimized expression system for the screening of antibody libraries displayed on the *Escherichia coli* surface," *Protein Eng.*, 12:613-621, 1999.

de Haard et al., "A large non-immunized human fab fragment phage library that permits rapid isolation and kinetic analysis of high affinity antibodies," *J. Biol. Chem.*, 274:18218, 1999.

De Haard et al., "Creating and engineering human antibodies for immunotherapy," *Advanced Drug Delivery Reviews*, 31:5-31, 1998.

Decad and Nikaido, "Outer membrane of gram-negative bacteria," *J. Bacteriol.*, 128:325, 1976.

Deng et al., "Selection of antibody single-chain variable fragments with improved carbohydrate binding by phage display," *J. Biol. Chem.*, 269:9533, 1994.

Deng et al., "Basis for selection of improved carbohydrate-binding single-chain antibodies from synthetic gene libraries," *Proc. Natl. Acad. Sci. USA*, 92:4992, 1995.

deWilt et al., "Antibody arrays for high-throughput acreening of antibody-antigen interactions," *Nat. Biotechnol.*, 18:989, 2000.

Dueñas and Borrebaeck, "Clonal selection and amplification of phage displayed antibodies by linking antigen recognition and phage recognition," *Biotechnology*, 12:999, 1994.

Georgiou et al., "Display of heterologous proteins on the surface of microorganisms: from the screening of combinatorial libraries to live recombinant vaccines," *Nat. Biotechnol.*, 15:29-34, 1997.

Georgiou, "Analysis of large libraries of protein mutants using flow cytometry," *Adv. Protein Chem.*, 55:293-315, 2000.

Giep et al., "pSKAP/S: an expression vector for the production of single-chain Fv alkaline phosphatase fusion proteins," *Prot. Exp. Purif.*, 16:63-69, 1999.

Griffiths et al., "Isolation of high affinity human antibodies directly from large synthetic repertoires," *EMBO J.*, 13:3245-3260, 1994.

Hawkins et al., "Selection of phage antibodies by binding affinity mimicking affinity maturation," *J. Mol. Biol.*, 226:889-896, 1992.

Hayhurst and Georgiou, "High-throughput antibody isolation," *Curr. Opin. Chem. Biol.*, 5:683-689, 2001.

Hayhurst et al., "Isolation and expression of recombinant antibody fragments to the biological warfare pathogen *Brucella melitensis*," *J. Immunol. Methods*, 276:185-196, 2003.

Hayhurst, "Improved expression characteristics of single-chain Fv fragments when downstream of the *Escherichia coli* maltose-binding protein or upstream of a single immunoglobulin-constant domain," *Protein Expr. Purif.*, 18:1-10, 2000.
Hoess, *Chem. Rev.*, "Protein design and phage display," 101:3205-3218, 2001.
Hoichen et al., *Applied and Environmental Microbiology*, "Novel bacterial membrane surface display system using cell wall-less L-forms of *Proteys mirabilis* and *Escherichia coli*," 68(2):525-531, 2002.
Hudson et al., "Recombinant antibody fragments," *Curr. Opin. Biotechnol.*, 9:395, 1998.
Hultgren et al., "Pilus and nonpilus bacterial adhesins: assembly and function in cell recognition," *Cell*, 73:887-901, 1993..
Johns et al., "In vivo selection of sFv from phage display libraries," *J. Immunol. Methods*, 239:137-151, 2000.
Kjaer et al., "Glycerol diversities phage repertoire selections and lowers non-specific phage absorption," *FEBS Lett.*, 431:448-452, 1998.
Knappik et al., "Fully synthetic human cmbinatorial antibody libraries(HuCAL) based on modular consensus frameworks and CDRs randomized with trinucleotides," *J. Mol. Biol.*, 296:57-86, 2000.
Krebber et al., "Inclusion of an upstream transcriptional terminator inphage display vectors abolishes background expressiono f toxic fusions with coat protein g3p," *Gene*, 178:71-74, 1996.
Krebber et al., "Reliable cloning of functional antibody variable domains form hybridomas and spleen cell repertoires employing a reengineered phage display system," *J. Immunol. Methods*, 201:35-55, 1997.
Levitan, "Stochastic modeling and optimization of phage display," *J. Mol. Biol.*, 277:893-916, 1998.
Low et al., "Mimicking somatic hypermutation: affinity maturation of antibodies displayed on bacteriophage using a bacterial mutator strain," *J. Mol. Biol.*, 260: 359-368, 1996.
MacKenzie and To, "The role of valency in the selection of anti-carbohydrate single-chain Fvs from phage display libraries," *J. Immunol. Methods*, 220:39-49, 1998.
MacKenzie et al., "Analysis by surface plasmon resonance of the influence of valence on the ligand binding affinity and kinetics of an anti-carbohydrate antibody," *J. Biol. Chem.*, 271(3):1527-1533, 1996.
Maenaka et al., "A stable phage-display system using a phagemid vector: phage display of hen egg-white lysozyme (HEL), *Escherichia coli* alkaline, phosphatase, and anti-HEL monoclonal antibody, HyHEL10," *Biochem. Biophys. Res. Commun.*, 218:682, 1996.
Malmborg et al., "Selection of binders form phage displayed antibody libraries using the BIAcore biosensor," *J. Immunol. Methods*, 198:51-57, 1996.
Maynard and Georgiou, "Antibody Engineering," *Annu. Rev. Biomed. Eng.*, 339-76, 2000.
Maynard et al., "Protection against anthrax toxin by recombinant antibody fragments correlates with antigen affinity," *Nat. Biotechnol.*, 20:597-601, 2002.
Mingarro et al., "Membrane-protein engineering," *Trends Biotechnol.*, 15:432-437, 1997.
Miroux and Walker, "Over-production of proteins in *Escherichia coli*: mutant hosts that allow synthesis of some membrane proteins and globular proteins at high levels," *J. Mol. Biol.*, 260:289-298, 1996.
Mutuberria et al., "Model systems to study the parameters determining the success of phage antibody selections on complex antigens," *J. Immunol. Methods*, 231:65-81, 1999.
Nikaido and Vaara, "Molecular basis of bacterial outer membrane permeability," *Microbiol. Rev.*, 49(1):1-32, 1985.
Nikaido, "Multidrug efflux pumps of gram-negative bacteria," *Journal of Bacteriology*, 178(20):5853-5859, 1996.
Oliver, "Periplasm," 88-103, 1996.
Pini et al., "Design and use of a phage display library," *J. Biol. Chem.*, 273(34):21769, 1998.
Pugsley, "The complete general secratory pathway in gram-negative bacteria," *Microbiol. Rev.*, 57(1):50-108, 1993.
Rodi and Makowski, "Phage-display technology-finding a needle in a vast molecular haystack," *Curr. Opin. Biotechnol.*, 10:87-93, 1999.
Sagt et al., "Impaired cutinase secretion in *Saccharomyces cerevisiae* induces irregular endoplasmic reticulum (ER) membran proliferation, oxidative stress, and ER-associated degradation," *Appl. Environ. Microbiol.*, 68(5):2155-2160, 2002.
Sblattero and Bradbury, "Exploiting recombination in single bacteria to make large phage antibody libraries," *Nat. Biotechnol.*, 18:75-80, 2000.

Seydel et al., "Testing the '2+ rule' for lipoprotein sorting in the *Escherichia coli* cell envelope with a new genetic selection," *Mol. Microbiol.*, 34(4):810-821, 1999.

Sheets et al., "Efficient construction of a large nonimmune phage antibody library: the production of high-affiity human single-chain antibodies to protien antigens," *Proc. Natl. Acad. Sci. USA*, 95:6157-6162, 1998.

Shusta et al., "Yeast polypeptide fusion surface display levels predict thermal stability and soluble secreation efficiency," *J. Micro. Biol.*, 292:949-956, 1999.

Stathopoulos et al., "Characterization of *Escherichia coli* expressing an Lpp'OmpA(46-159)-PhoA fusion protein localized in the outer membrane," *Appl. Microbiol. Biotechnol.*, 45:112-119, 1996.

Thompson et al., "Affinity maturation of a high-affinity human monoclonal antibody agaisnt the third hypercvariable loop of human immunodeficiency virus: use of phage display to improve affinity and broaden strain reactivity," *J. Mol.Biol.*, 256:77-88, 1996.

Vaughan et al., "Human antibodies with sub-nanometer affinites isolated from a large non-immunized phage display library," *Nat. Biotechnol.*, 14:309-314, 1996.

Wittrup, "The single cell as a microplate well," *Nat. Biotechnol.*, 18:1039-1040, 2000.

Yakushi et al., "Lethality of the covalent linkage between mislocalized major outer membrane lipoprotein and the poptidoglycan of *Escherichia coli*," *Journal of Bacteriology*, 179(9):2857, 1997.

Yakushi et al., "A new ABC transporter mediating the detachment of lipid-modified proteins from membranes," *Nat. Cell. Biol.*, 2:212-218, 2000.

Yamaguchi, "A single amino acid determinant of the membrane localization of lipoproteins in *E. coli*," *Cell*, 53(3):423-432, 1988.

Yu et al., "Lipoprotein-28, a cytoplasmic membrane lipoprotein from *Escherichia coli*," *J. Biol. Chem.*, 261(5):2284-2288, 1986.

Co-pending U.S. Appl. No. 09/699,023, filed on Oct. 27, 2000.

Co-pending U.S. Appl. No. 10/620,049, filed on Jul. 15, 2002..

Harvey et al., "Anchored periplasmic expression, a versatile technology for the isolation of high-affinity antibodies from *Escherichia coli*-expressed libraries," *Proc. Natl. Acad. Sci., USA*, 101(25):9193-9198, 2004.

Boder et al., "Directed evolution of antibody fragments with monovalent femtomolar antigen-binding affinity," *Proc. Natl. Acad. Sci. USA*, 97(20):10701-10705, 2000.

Burman et al., *J. Bacteriol.*, "Murein and the outer penetration barrier of *Escheriachia coli* K-12, *Proteus mirabilis*, and *Pseudomonas aeruginosa*," Journal of Bacteriology, 112(3):1364-1374, 1972.

Chen et al., "Selection and analysis of an optimized anti-VEGF antibody: crystal structure of an affinity-matured Fab in complex with antigen," *J. Mol. Biol.*, 293:865, 1999.

Chen et al., *Nat. Biotechnol.*, "Isolation of high-affinity ligand-binding proteins by periplasmic expression with cytometric screening (PECS)," 19(6):537-542, 2001.

* cited by examiner

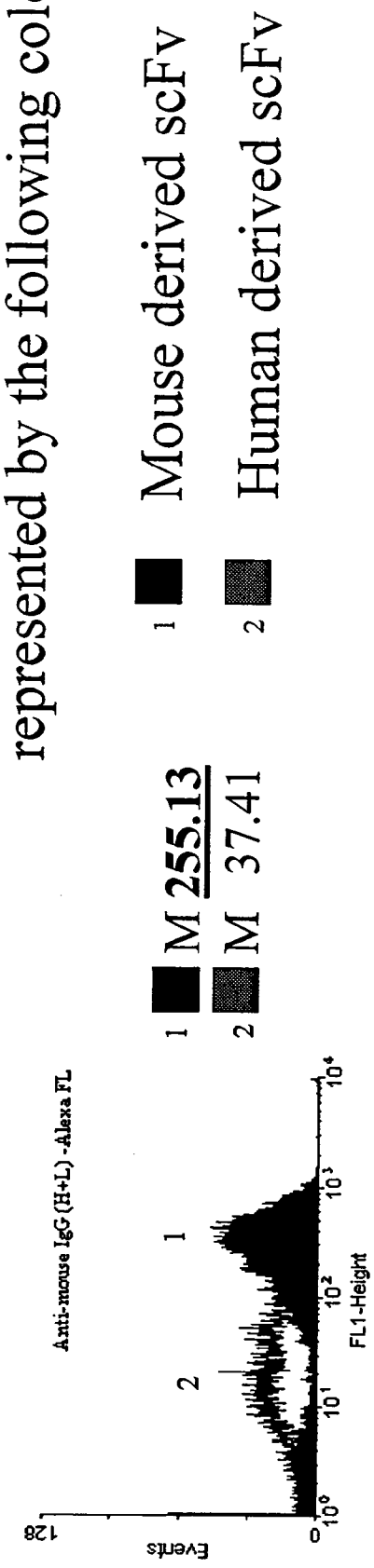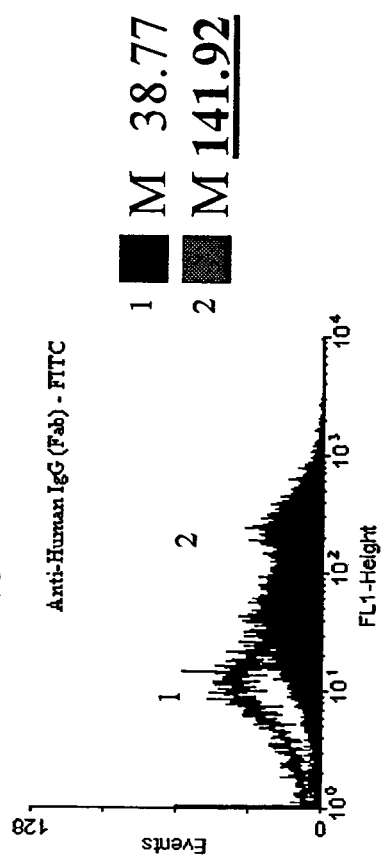
FIG. 2A
FIG. 2B

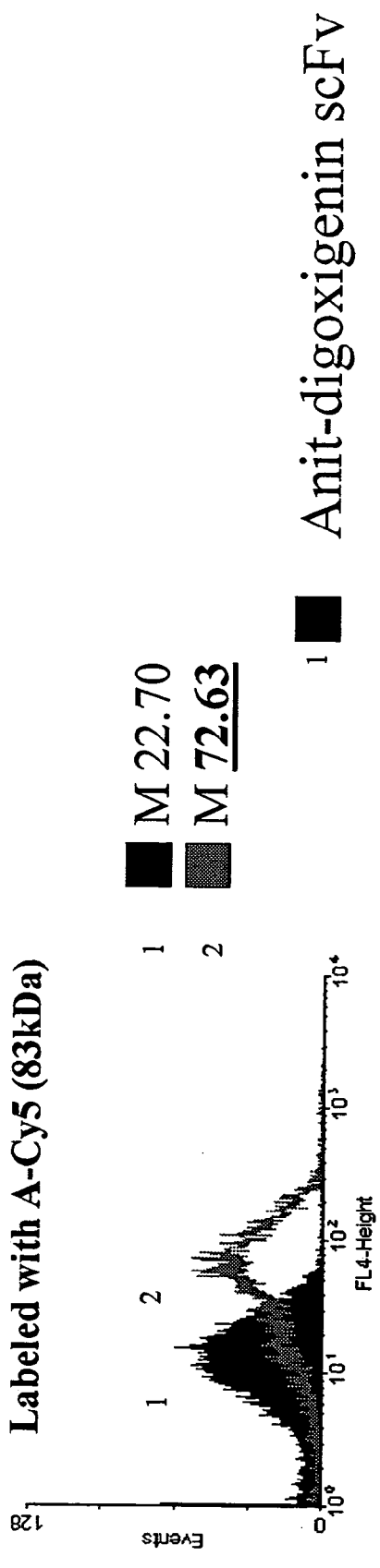
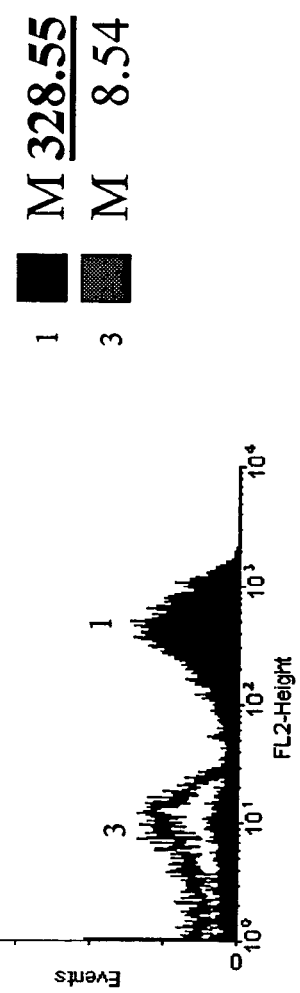
FIG. 3A
FIG. 3B

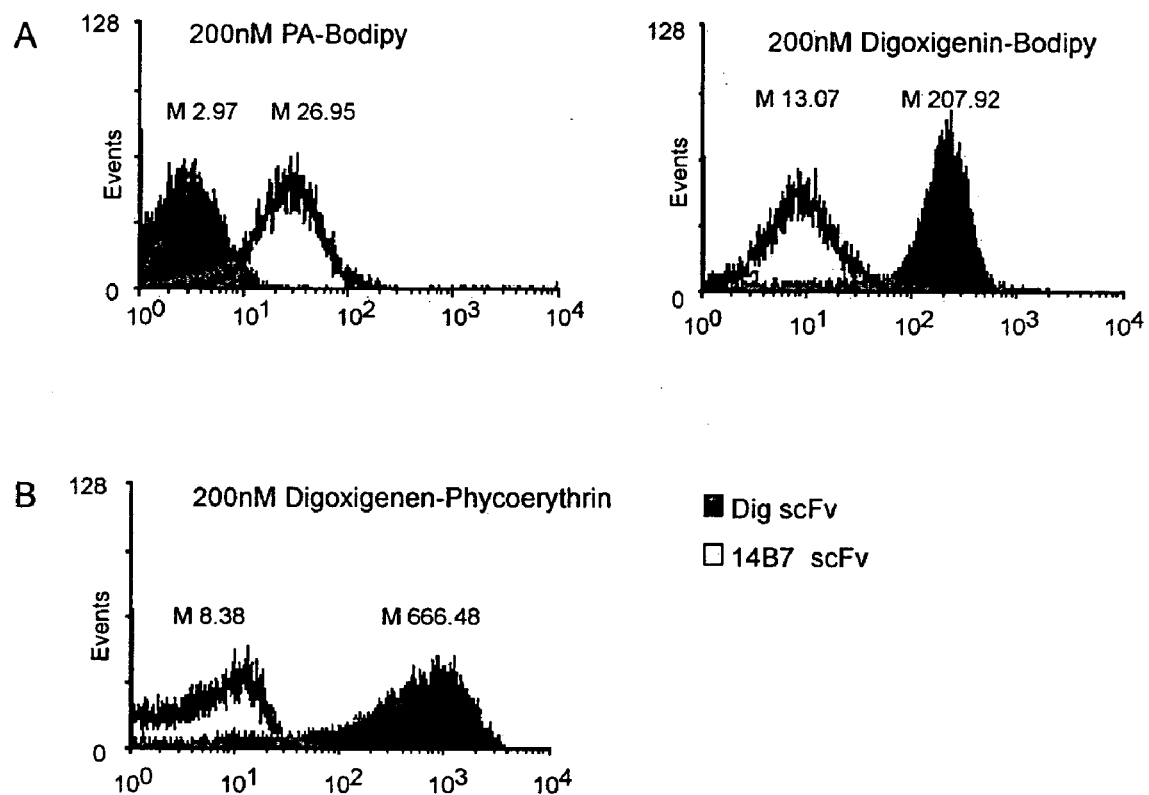
FIG. 7A, B

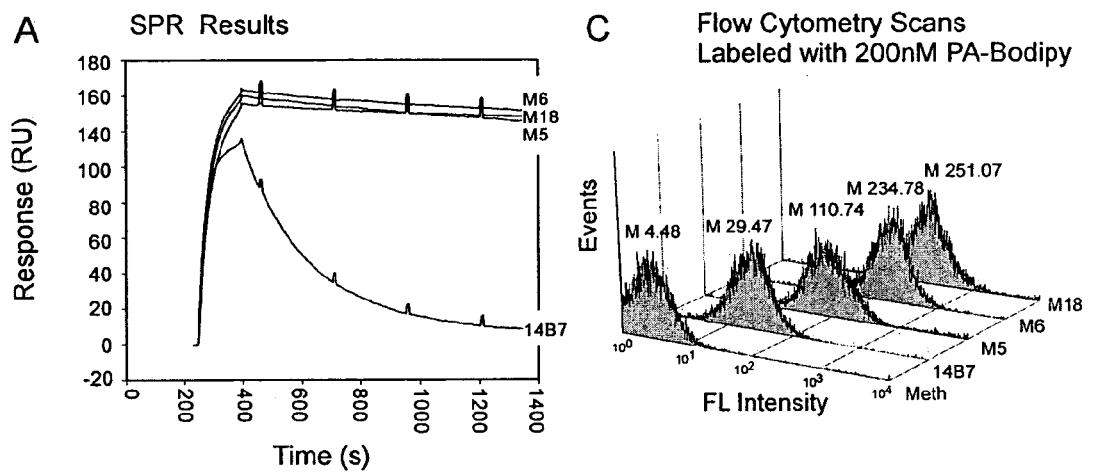
FIG. 8A-C

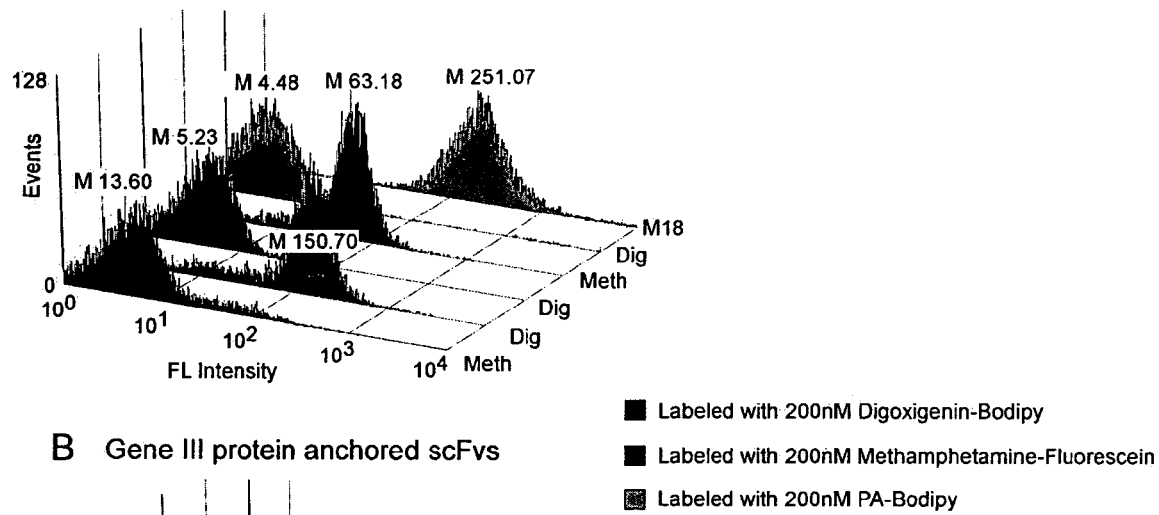
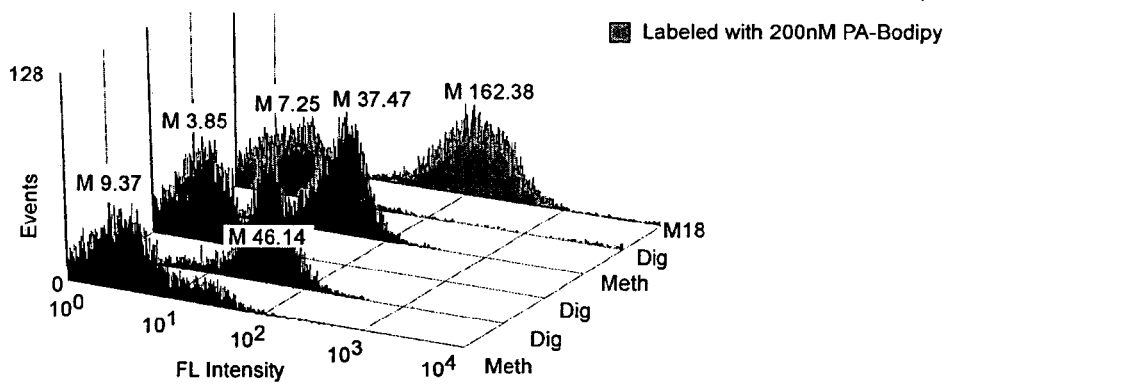
FIG. 9A, B

SEQUENCE LISTING

<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic Primer

```
<400> SEQUENCE: 1
caggaaacag ctatgac                                                  17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gaattttctg tatgagg                                                  17

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
gccacctccg cctgaacc                                                 18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
ctatgcggcc ccattca                                                  17

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5 aaaaa                                                                5

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaaggagata tacatatgaa actgacaaca catcatcta                          39

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer
```

-continued

```
<400> SEQUENCE: 7
ctgggccatg gccggctggg cctcgctgct actctggtcg caacc          45

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Gln Thr Thr His Val Pro Pro
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Gln Thr Thr His Val Pro Pro
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gln Thr Thr His Ser Pro Ala
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gln Thr Thr His Leu Pro Thr
  1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Gln Thr Thr His Thr Pro Pro
  1               5

<210> SEQ ID NO 13
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      Peptide

<400> SEQUENCE: 13

Gln Thr Thr His Thr Pro Pro
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Gln Thr Thr His Ile Pro Thr
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Gln Thr Thr His Val Pro Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Gln Thr Thr His Val Pro Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Gln Thr Thr His Ile Pro Ala
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Gln Thr Thr His Leu Pro Ala
 1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Gln Thr Thr His Val Pro Cys
 1               5

<210> SEQ ID NO 20
<211> LENGTH: 741
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gatattcaga tgacacagac tacatcctcc ctgtctgcct ctctgggaga cagagtcacc    60
atcagttgca gggcaagtca ggacattagg aattatttaa actggtatca gcagaaacca   120
gatggaactg ttaaactcct gatctactac acatcaagat acagtcagg agtcccatca    180 aggttcagtg gcagtgggtc tggaacagat tattctctca ccattagcaa ccaggagcaa   240
gaagatattg cacttacttt tgccaacag ggtaatacgc ttccgtggac gttcggtgga    300
ggcaccaagc tggaaataaa acgtggtggt ggtggttctg gtggtggtgg ttctggcggc   360
ggcggctccg gtggtggtgg atccgaggtc caactgcaac agtctggacc tgagctggtg   420
aagcctgggg cctcagtgaa gatttcctgc aaagattctg gctacgcatt cagtagctct   480
tggatgaact gggtgaagca gaggcctgga cagggtcttg agtggattgg acggatttat   540
cctggagatg gagatactaa ctacaatggg aagttcaagg gcaaggccac actgactgca   600
gacaaatcct ccagcacagc ctacatgcag ctcagcagcc tgacctctgt ggactctgcg   660
gtctatttct gtgcaagatc ggggttacta cgttatgcta tggactactg gggtcaagga   720
acctcagtca ccgtctcctc g                                              741

<210> SEQ ID NO 21
<211> LENGTH: 247
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Gln Glu Gln
65                  70                  75                  80

Glu Asp Ile Gly Thr Tyr Phe Cys Gln Gln Gly Asn Thr Leu Pro Trp
                85                  90                  95

-continued

```
Thr Phe Gly Gly Gly Thr Lys Leu Glu Ile Lys Arg Gly Gly Gly
            100                 105                 110
Ser Gly Gly Gly Gly Ser Gly Gly Gly Ser Gly Gly Gly Ser
        115                 120                 125
Glu Val Gln Leu Gln Gln Ser Gly Pro Glu Leu Val Lys Pro Gly Ala
    130                 135                 140
Ser Val Lys Ile Ser Cys Lys Asp Ser Gly Tyr Ala Phe Ser Ser Ser
145                 150                 155                 160
Trp Met Asn Trp Val Lys Gln Arg Pro Gly Gln Gly Leu Glu Trp Ile
                165                 170                 175
Gly Arg Ile Tyr Pro Gly Asp Gly Asp Thr Asn Tyr Asn Gly Lys Phe
            180                 185                 190
Lys Gly Lys Ala Thr Leu Thr Ala Asp Lys Ser Ser Ser Thr Ala Tyr
        195                 200                 205
Met Gln Leu Ser Ser Leu Thr Ser Val Asp Ser Ala Val Tyr Phe Cys
    210                 215                 220
Ala Arg Ser Gly Leu Leu Arg Tyr Ala Met Asp Tyr Trp Gly Gln Gly
225                 230                 235                 240
Thr Ser Val Thr Val Ser Ser
                245
```

```
<210> SEQ ID NO 22
<211> LENGTH: 741
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
gatattcaga tgacacagac tacatcctcc ctgtctgcct ctctgggaga cagagtcacc    60
gtcagttgca gggcaagtca ggacattagg aattatttaa actggtatca gcagaaacca   120
gacggaactg ttaaattcct gatctactac acatcaagat acagccagg agtcccatca    180 aggttcagtg gcagtgggtc tggaacagat tattccctca ccattaacaa cctggagcag   240
gaagatattg cacttacttt tgccaacag ggcaatacgc ctccgtggac gttcggtgga    300
ggcaccaagc tggaaataaa acgtggtgga ggtggttctg atggtggtgg ttctggcggc   360
ggcggctccg gtggtggtgg atccgaggtc caactgcaac agtctggacc tgagctggtg   420
aagcctgggg cctcagtgaa gatttcctgc aaagattctg gctacgcatt caatagctct   480
tggatgaact gggtgaagca gaggcctgga caggtcttg agtggattgg acggatttat    540
cctggagatg gagattctaa ctacaatggg aaattcgagg gcaaggccat actgactgca   600
gacaaatcct ccagcacagc ctacatgcag ctcagcagcc tgacctctgt ggactctgcg   660
gtctatttct gtgcaagatc gggggttgcta cgttatgcta tggactactg ggtcaagga   720 acctcagtca ccgtctcctc g                                             741
```

```
<210> SEQ ID NO 23
<211> LENGTH: 247
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 23
```

```
Asp Ile Gln Met Thr Gln Thr Thr Ser Ser Leu Ser Ala Ser Leu Gly
 1               5                  10                  15

Asp Arg Val Thr Val Ser Cys Arg Ala Ser Gln Asp Ile Arg Asn Tyr
                20                  25                  30

Leu Asn Trp Tyr Gln Lys Pro Asp Gly Thr Val Lys Phe Leu Ile
            35                  40                  45

Tyr Tyr Thr Ser Arg Leu Gln Pro Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Gly Thr Tyr Phe Cys Gln Gln Gly Asn Thr Pro Pro Trp
                85                  90                  95

Thr Phe Gly Gly Gly Thr Lys Leu Glu Ile Lys Arg Gly Gly Gly Gly
            100                 105                 110

Ser Asp Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
        130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Ser Asn Tyr Asn Gly Lys Phe
            180                 185                 190

Glu Gly Lys Ala Ile Leu Thr Ala Asp Lys Ser Ser Ser Thr Ala Tyr
        195                 200                 205

Met Gln Leu Ser Ser Leu Thr Ser Val Asp Ser Ala Val Tyr Phe Cys
        210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245
```

<210> SEQ ID NO 24
<211> LENGTH: 741
<212> TYPE: DNA
<213> ORGANISM: Artificial Sequence
<220> FEATURE:
<223> OTHER INFORMATION: Description of Artificial Sequence: Synthetic Primer

<400> SEQUENCE: 24

```
gatattcaga tgacacagac tacatcctcc ctgtctgcct ctctgggaga cagagtcacc    60
gtcagttgca gggcaagtca ggacattagg aattatttaa actggtatca gcagaaacca   120
gacggaactg ttaaattcct gatctactac acatcaagat actgccagg  agtcccatca   180 aggttcagtg gcagtgggtc tggaacagat tattcccta  ccattaacaa cctggagcag   240
gaagatattg gcacttactt ttgccaacag ggcaatacgc ctccgtggac gttcggtgga   300
ggcaccaagc tggaaataaa acgtggtgga ggtggttctg atggtggtgg ttctggcggc   360
ggcggctccg gtggtggtgg atccgaggtc caactgcaac agtctggacc tgagctggtg   420
aagcctgggg cctcagtgaa gatttcctgc aaagattctg gctacgcatt caatagctct   480
tggatgaact gggtgaagca gaggcctgga cagggtcttg agtggattgg acggatttat   540
```

-continued

```
cctggagatg gagattctaa ctacaatggg aaattcgagg gcaaggccat actgacagca    600
gacaaatcct ccagcacagc ctacatgcag ctcagcagcc tgacctctgt ggactctgcg    660
gtctatttct gtgcaagatc ggggttgcta cgttatgcta tggactactg gggtcaagga    720
acctcagtca ccgtctcctc g                                              741
```

<210> SEQ ID NO 25
<211> LENGTH: 247
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

```
Asp Ile Gln Met Thr Gln Thr Thr Ser Ser Leu Ser Ala Ser Leu Gly
  1               5                  10                  15

Asp Arg Val Thr Val Ser Cys Arg Ala Ser Gln Asp Ile Arg Asn Tyr
             20                  25                  30

Leu Asn Trp Tyr Gln Gln Lys Pro Asp Gly Thr Val Lys Phe Leu Ile
         35                  40                  45

Tyr Tyr Thr Ser Arg Leu Leu Pro Gly Val Pro Ser Arg Phe Ser Gly
 50                  55                  60

Ser Gly Ser Gly Thr Asp Tyr Ser Leu Thr Ile Asn Asn Leu Glu Gln
 65                  70                  75                  80

Glu Asp Ile Gly Thr Tyr Phe Cys Gln Gln Gly Asn Thr Pro Pro Trp
             85                  90                  95

Thr Phe Gly Gly Gly Thr Lys Leu Glu Ile Lys Arg Gly Gly Gly Gly
            100                 105                 110

Ser Asp Gly Gly Ser Gly Gly Gly Ser Gly Gly Gly Ser
            115                 120                 125

Glu Val Gln Leu Gln Gln Ser Gly Pro Glu Leu Val Lys Pro Gly Ala
130                 135                 140

Ser Val Lys Ile Ser Cys Lys Asp Ser Gly Tyr Ala Phe Asn Ser Ser
145                 150                 155                 160

Trp Met Asn Trp Val Lys Gln Arg Pro Gly Gln Gly Leu Glu Trp Ile
                165                 170                 175

Gly Arg Ile Tyr Pro Gly Asp Gly Asp Ser Asn Tyr Asn Gly Lys Phe
            180                 185                 190

Glu Gly Lys Ala Ile Leu Thr Ala Asp Lys Ser Ser Thr Ala Tyr
        195                 200                 205

Met Gln Leu Ser Ser Leu Thr Ser Val Asp Ser Ala Val Tyr Phe Cys
210                 215                 220

Ala Arg Ser Gly Leu Leu Arg Tyr Ala Met Asp Tyr Trp Gly Gln Gly
225                 230                 235                 240

Thr Ser Val Thr Val Ser Ser
                245
```

COMBINATORIAL PROTEIN LIBRARY SCREENING BY PERIPLASMIC EXPRESSION

This application claims the priority of U.S. Provisional Patent App. No. 60/396,058, filed Jul. 15, 2002, and is also a continuation-in-part of U.S. patent application Ser. No. 09/699,023, filed Oct. 27, 2000. The entire disclosures of the foregoing applications are incorporated herein by reference.

The government may own rights in the present invention pursuant to the U.S. Army ARO MURI program and the Texas Consortium for Development of Biological Sensors and in connection with contract number DADD17-01-D-0001 with the U.S. Army Research Laboratory.

BACKGROUND OF THE INVENTION

1. Field of the Invention

The present invention relates generally to the field of protein engineering. More particularly, it concerns improved methods for the screening of combinatorial libraries of polypeptides to allow isolation of ligand binding polypeptides.

2. Description of Related Art

The isolation of polypeptides that either bind to ligands with high affinity and specificity or catalyze the enzymatic conversion of a reactant (substrate) into a desired product is a key process in biotechnology. Ligand-binding polypeptides, including proteins and enzymes with a desired substrate specificity can be isolated from large libraries of mutants, provided that a suitable screening method is available. Small protein libraries composed of $10^3$–$10^5$ distinct mutants can be screened by first growing each clone separately and then using a conventional assay for detecting clones that exhibit specific binding. For example, individual clones expressing different protein mutants can be grown in microtiter well plates or separate colonies on semisolid media such as agar plates. To detect binding the cells are lysed to release the proteins and the lysates are transferred to nylon filters, which are then probed using radiolabeled or fluorescently labeled ligands (DeWildt et al. 2000). However, even with robotic automation and digital image systems for detecting binding in high density arrays, it is not feasible to screen large libraries consisting of tens of millions or billions of clones. The screening of libraries of that size is required for the de novo isolation of enzymes or protein binders that have affinities in the subnanomolar range.

The screening of very large protein libraries has been accomplished by a variety of techniques that rely on the display of proteins on the surface of viruses or cells (Ladner et al. 1993). The underlying premise of display technologies is that proteins engineered to be anchored on the external surface of biological particles (i.e., cells or viruses) are directly accessible for binding to ligands without the need for lysing the cells. Viruses or cells displaying proteins with affinity for a ligand can be isolated in a variety of ways including sequential adsorption/desorption form immobilized ligand, by magnetic separations or by flow cytometry (Ladner et al. 1993, U.S. Pat. No. 5,223,409, Ladner et al. 1998, U.S. Pat. No. 5,837,500, Georgiou et al. 1997, Shusta et al. 1999).

The most widely used display technology for protein library screening applications is phage display. Phage display is a well-established and powerful technique for the discovery of proteins that bind to specific ligands and for the engineering of binding affinity and specificity (Rodi and Makowski, 1999). In phage display, a gene of interest is fused in-frame to phage genes encoding surface-exposed proteins, most commonly pIII. The gene fusions are translated into chimeric proteins in which the two domains fold independently. Phage displaying a protein with binding affinity for a ligand can be readily enriched by selective adsorption onto immobilized ligand, a process known as "panning". The bound phage is desorbed from the surface, usually by acid elution, and amplified through infection of *E. coli* cells. Usually, 4–6 rounds of panning and amplification are sufficient to select for phage displaying specific polypeptides, even from very large libraries with diversities up to $10^{10}$. Several variations of phage display for the rapid enrichment of clones displaying tightly binding polypeptides have been developed (Duenas and Borrebaeck, 1994; Malmborg et al., 1996; Kjaer et al., 1998; Burioni et al., 1998; Levitan, 1998; Mutuberria et al., 1999; Johns et al., 2000).

One of the most significant applications of phage display technology has been the isolation of high affinity antibodies (Dall'Acqua and Carter, 1998; Hudson et al., 1998; Hoogenboom et al., 1998; Maynard and Georgiou, 2000). Very large and structurally diverse libraries of scFv or $F_{AB}$ fragments have been constructed and have been used successfully for the in vitro isolation of antibodies to a multitude of both synthetic and natural antigens (Griffiths et al., 1994; Vaughan et al., 1996; Sheets et al., 1998; Pini et al., 1998; de Haard et al., 1999; Knappik et al., 2000; Sblattero and Bradbury, 2000). Antibody fragments with improved affinity or specificity can be isolated from libraries in which a chosen antibody had been subjected to mutagenesis of either the CDRs or of the entire gene CDRs (Hawkins et al., 1992; Low et al., 1996; Thompson et al., 1996; Chowdhury and Pastan, 1999). Finally, the expression characteristics of scFv, notorious for their poor solubility, have also been improved by phage display of mutant libraries (Deng et al., 1994; Coia et al., 1997).

However, several spectacular successes notwithstanding, the screening of phage-displayed libraries can be complicated by a number of factors. First, phage display imposes minimal selection for proper expression in bacteria by virtue of the low expression levels of antibody fragment gene III fusion necessary to allow phage assembly and yet sustain cell growth (Krebber et al., 1996, 1997). As a result, the clones isolated after several rounds of panning are frequently difficult to produce on a preparative scale in *E. coli*. Second, although phage displayed proteins may bind a ligand, in some cases their un-fused soluble counterparts may not (Griep et al., 1999). Third, the isolation of ligand-binding proteins and more specifically antibodies having high binding affinities can be complicated by avidity effects by virtue of the need for gene III protein to be present at around 5 copies per virion to complete phage assembly. Even with systems that result in predominantly monovalent protein display, there is nearly always a small fraction of clones that contain multiple copies of the protein. Such clones bind to the immobilized surface more tightly and are enriched relative to monovalent phage with higher affinities (Deng et al., 1995; MacKenzie et al., 1996, 1998). Fourth, theoretical analysis aside (Levitan, 1998), panning is still a "black box" process in that the effects of experimental conditions, for example the stringency of washing steps to remove weakly or non-specifically bound phage, can only be determined by trial and error based on the final outcome of the experiment. Finally, even though pIII and to a lesser extent the other proteins of the phage coat are generally tolerant to the fusion of heterologous polypeptides, the need to be incorporated into the phage biogenesis process imposes biological constraints that can limit library diversity. Therefore, there is a great need in the art for techniques capable of overcoming these limitations.

Protein libraries have also been displayed on the surface of bacteria, fungi, or higher cells. Cell displayed libraries are typically screened by flow cytometry (Georgiou et al. 1997, Daugherty et al. 2000). However, just as in phage display, the protein has to be engineered for expression on the outer cell surface. This imposes several potential limitations. For example, the requirement for display of the protein on the surface of a cell imposes biological constraints that limit the diversity of the proteins and protein mutants that can be screened. Also, complex proteins consisting of several polypeptide chains cannot be readily displayed on the surface of bacteria, filamentous phages or yeast. As such, there is a great need in the art for technology which circumvents all the above limitations and provides an entirety novel means for the screening of very large polypeptide libraries.

SUMMARY OF THE INVENTION

In one aspect, the invention provides a method of obtaining a bacterium comprising a nucleic acid sequence encoding a binding polypeptide having specific affinity for a target ligand comprising the steps of: (a) providing a Gram negative bacterium comprising an inner and an outer membrane and a periplasm, said bacterium expressing a nucleic acid sequence encoding a candidate binding polypeptide in the periplasm of said bacterium; (b) contacting the bacterium with a labeled ligand capable of diffusing into said periplasm; and (c) selecting said bacterium based on the presence of said labeled ligand bound to said candidate binding polypeptide. In one embodiment of the invention, the method comprises the steps of: (a) providing a Gram negative bacterium expressing a nucleic acid sequence encoding a fusion polypeptide comprising a candidate binding polypeptide and a polypeptide anchored to the outer side of the inner membrane of the bacterium; (b) contacting the bacterium with a labeled ligand capable of diffusing into the bacterium; and (c) selecting the bacterium based on the presence of the labeled ligand bound to the candidate binding polypeptide.

In certain embodiments of the invention, the method may be further defined as a method of obtaining a nucleic acid sequence encoding a binding polypeptide having a specific affinity for a target ligand, the method further comprising the step of: (d) cloning a nucleic acid sequence encoding the candidate binding polypeptide from the bacterium. In the method, the nucleic acid sequence may be further defined as operably linked to a leader sequence capable of directing the expression of the fusion polypeptide to the outer side of the inner membrane.

In one embodiment of the invention, the Gram negative bacterium is an *E. coli* bacterium. In certain further embodiments of the invention, the method may be further defined as comprising use of a population of Gram negative bacteria. Such a population may collectively express a plurality of fusion polypeptides comprising a plurality of candidate binding polypeptides. The population may be obtained by a method comprising the steps of: (a) preparing a plurality of nucleic acid sequences encoding a plurality of fusion polypeptides comprising a candidate binding polypeptide and a inner membrane anchor polypeptide; and (b) transforming a population of Gram negative bacteria with the DNA inserts. In the method, the population of Gram negative bacteria may be contacted with the labeled ligand.

In one embodiment of the invention, a candidate binding polypeptide is further defined as an antibody or fragment thereof or, alternatively, may be a binding protein other than an antibody. The candidate binding polypeptide may also be further defined as an enzyme. The labeled ligand may comprise a peptide, polypeptide, enzyme, nucleic acid and/or synthetic molecule. The labeled ligand may be labeled by any suitable means, including fluorescently labeled. In certain embodiments of the invention, the nucleic acid encoding a candidate binding polypeptide if further defined as flanked by known nucleic acid sequences, whereby the nucleic acid is capable of being amplified following the selection.

In certain embodiments of the invention, the method of obtaining a bacterium comprising a nucleic acid sequence encoding a binding polypeptide comprises treating the bacterium to increase the permeability of the outer membrane of the bacterium to the labeled ligand. Treating may comprise, in one embodiment of the invention, treating the bacterium with hyperosmotic conditions, treating the bacterium with physical stress and/or treating the bacterium with a phage. The method may comprise removing the outer membrane of the bacterium or alternatively using mutant bacteria having a defective outer membrane that allows the diffusion of polypeptides of various molecular weights. The method may also comprise growing the bacterium at a sub-physiological temperature, including about 25° C. The method may still further comprise removing labeled ligand not bound to the candidate binding polypeptide.

Selecting in accordance with the invention may comprise any suitable method. In one embodiment of the invention, the selection comprises flow cytometry (e.g., fluorescence activated cell sorting (FACS)). In another embodiment, the selection comprises magnetic separation. The ligand and candidate binding polypeptide may be reversibly bound. The polypeptide may be anchored to the outer side of the inner membrane by any suitable anchor, including an N-terminal fusion to a 6 residue sequence derived from the native *E. coli* lipoprotein NlpA, any transmemebrane protein or fragment thereof, and the gene III protein of filamentous phage or a fragment thereof.

In still yet another aspect, the invention provides an isolated antibody or fragment thereof that binds immunologically to *Bacillus anthracis* protective antigen with an affinity Kd of between about 140 pM and about 21 pM as determined by surface plasmon resonance. Such an antibody or fragment thereof may be further defined as binding immunologically to *Bacillus anthracis* protective antigen with a binding affinity Kd of between about 96 pM and about 21 pM and/or between about 35 pM and about 21 pM. The isolated antibody or fragment thereof may still further be defined as comprising an Fc domain of IgA, IgD, IgE, IgG or IgM. The antibody may be a humanized antibody and may be a human antibody. In certain embodiments, the isolated antibody or fragment thereof comprises an scFv fragment and antibody constant regions forming a monovalent antibody portion of at least 40 kDa.

In still yet another aspect, the invention provides an isolated antibody or fragment thereof that binds immunologically to *Bacillus anthracis* protective antigen and comprises the variable light and variable heavy chain of SEQ ID NO:21, with the exception that the variable light and variable heavy chain comprise a modification selected from the group consisting of: I21V, S22G, L33S, Q38R, L46F, Q55L, S56P, T74A, S76N, Q78L, L94P, S7P, K19R, S30N, T57S, K62R, K64E, T68I, and M80L; wherein said I21V, S22G, L33S, Q38R, L46F, Q55L, S56P, T74A, S76N, Q78L and L94P are in the variable light chain and wherein said S7P, K19R, S30N, T57S, K62R, K64E, T68I and M80L are in the variable heavy chain. In certain embodiments of the invention, the isolated antibody or fragment thereof may be defined as comprising from about two to at all of said modifications, including about 3, 4, 5, 6, 7, 8, 9, 10, 11, 12, 13, 14, 15, 16, 17, 18 or all of the modifications, including all possible combinations of the foregoing modifications.

In certain aspects of the invention, the isolated antibody or fragment thereof is further defined as binding immunologically to *Bacillus anthracis* protective antigen with an affinity Kd of between about 140 pM and about 21 pM as determined by surface plasmon resonance. In further embodiments of the invention the antibody or fragment thereof comprises Q55L and S56P. The isolated antibody or fragment thereof may comprising the variable light and/or variable heavy chain of SEQ ID NO:22 or SEQ ID NO:24. In one embodiment, the isolated antibody or fragment thereof comprises SEQ ID NO:22 and/or SEQ ID NO:24. The isolated antibody or fragment thereof may be further defined as a scAb, Fab or SFv and may also be further defined as comprising an Fc domain of IgA, IgD, IgE, IgG or IgM. The isolated antibody or fragment thereof may be a humanized antibody and may be human. In particular embodiments, the isolated antibody or fragment thereof comprises an scFv fragment and antibody constant regions forming a monovalent antibody portion of at least 40 kDa.

In still yet another aspect, the invention provides an isolated nucleic acid encoding an antibody or fragment thereof provided by the invention. In one embodiment, the nucleic acid encodes the variable light chain of SEQ ID NO:23 and/or SEQ ID NO:25. In another embodiment, the nucleic acid encodes the variable heavy chain of SEQ ID NO:23 and/or SEQ ID NO:25. In yet another embodiment, nucleic acid encodes the polypeptide of SEQ ID NO:23 and, in another embodiment, the polypeptide of SEQ ID NO:25.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A–B: Detection of ScFvs on the Surface of Spheroplasts. APEx expressed scFvs in *E. coli* represented as indicated. ScFvs expressed were capable of binding large antigens, e.g., PA-Cy5 (83 kD), Phycoerythrin-digoxigenin (240 kD). Provides evidence that scFvs expressed via APEx are accessible to large proteins.

FIGS. 3A–B: Detection of ScFvs for Larger Target Antigen conjugated fluorophores.

FIG. 7: Examples of targets visualized by APEx. (A) Fluorescence distribution of ABLEC™ cells expressing PA specific (14B7) and digoxigenin specific (Dig) scFv and labeled with 200 nM Bodipy™ conjugated fluorescent antigens. Histograms represent the mean fluorescence intensity of 10,000 *E. Coli* events. (B) Histograms of cells expressing 14B7 or Dig scFv labeled with 200 nM of the 240 kDa digoxigenin-phycoerythrin conjugate.

FIG. 8: Analysis of anti-PA antibody fragments selected using APEx (A) Signal Plasmon Resonance (SPR) analysis of anti-PA scAb binding to PA. (B) Table of affinity data acquired by SPR. (C) FC Histogram of anti-PA scFv in pAPEx1 expressed in *E. coli* and labeled with 200 nM PA-Bodipy™ conjugate as compared with anti-methamphetamine (Meth) scFv negative control.

FIG. 9: N-Terminal vs. C-Terminal anchoring strategy comparison. (A) Anti-digoxigenin Dig scfv, anti-PA M18 scFv and anti-methamphetamine Meth scFv expressed as N-terminal fusions in the pAPEx1 vector in *E. coli* specifically label with 200 nM of their respective antigen. (B) C-terminal fusions of same scFv in pAK200 vector specifically labeled with 200 nM of their respective antigen.

DESCRIPTION OF ILLUSTRATIVE EMBODIMENTS

Figure 1A:
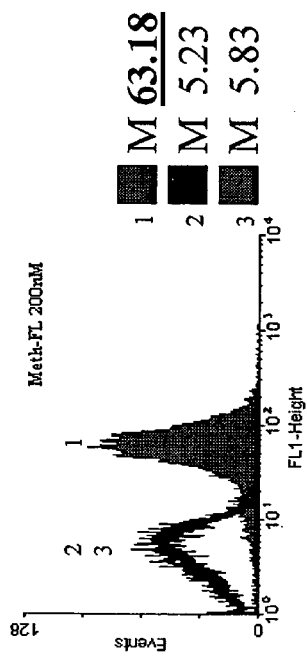
FIGS. 1A–C: Selective identification of Antigen targets with APEx. APEx expressed scFvs in *E. coli* represented as indicated. Shows scFvs expressed that bind small molecules, (A) digoxigenin-Bodipy FL, (B) methamphetamine-FL; or ScFvs expressed that bind peptides (C) e.g., peptide 18aa.

The invention overcomes the limitations of the prior art by providing a novel method for isolating binding polypeptides, including antibodies or antibody fragments, that recognize specific molecular targets. In the technique, a library of polypeptide (e.g., antibody or other binding polypeptides) mutants can be constructed and expressed in Gram negative bacteria. The mutant polypeptides can be expressed as fusion proteins that are anchored on the inner (cytoplasmic) membrane of the bacterium facing the periplasm. A fusion polypeptide is a polypeptide comprised of two or more starting polypeptides linked to form a continuous polypeptide. The polypeptides linked are typically derived from distinct sources. Subsequently, the periplasmic (outer) membrane of the bacterium is made permeable using a variety of chemical, physical or other treatments or using mutations that result in increased permeability. Permeabilization of the bacterial outer membrane renders the polypeptides anchored on the membrane accessible to target large molecules added to the external solution.

The display of heterologous proteins on microbial scaffolds has attractive applications in many different areas including vaccine development, bioremediation and protein engineering. In Gram negative bacteria there have been display systems designed which by virtue of a N or C terminal chimera fusion, proteins are displayed to the cell surface. Although there have been many different strategies used to direct protein localization, including fusions to outer membrane proteins, lipoproteins, surface structural proteins and leader peptides, many share the same limitations. One limitation is the size of the protein which can be displayed.

Many display scaffolds can only tolerate a few hundred amino acids, which significantly limits the scope of proteins which can be displayed. Also, display implies that the protein of interest is situated such that it can interact with its environment, yet the major limitation of many of these systems is that the architecture of the outer surface of gram negative bacteria and in particular the presence of lipopolysaccharide (LPS) molecules having steric limitations that inhibit the binding of externally added ligands. Another limitation arises from the requirement that the displayed protein is localized on the external surface of the outer membrane. For this purpose the polypeptide must first be secreted across the cytoplasmic membrane must then transverse the periplasmic space and finally it must be assemble properly in the outer membrane. A binding polypeptide may be any type of molecule of at least two amino acid residues capable of binding a given ligand. By binding it is meant that immunological interaction takes place. Biosynthetic limitations restrict the kinds of proteins that can be displayed in this fashion. For example, large polypeptides (e.g., alkaline phosphatase) cannot be displayed on the *E. coli* surface (Stathopoulos et al., 1996).

In accordance with the invention, the limitations of the prior techniques can be overcome by the display of proteins anchored to the outer surface of the inner membrane. It was demonstrated using the technique that, by utilizing conditions that permeabilize the outer membrane, *E. coli* expressing inner membrane anchored scFv antibodies (approx. 30 kDa in size) can be labeled with a target antigen conjugated, for example, to a fluorophore and can subsequently be used to sort protein libraries utilizing flow cytometry for isolation of gain of function mutants.

Following disruption of the outer bacterial membrane, which is well known to those of skill in the art and may comprise, for example, use of Tris-EDTA-lysozyme, labeled antigens with sizes up to at least 240 kDa can be detected. With fluorescent labeling, cells may be isolated by flow cytometry and the DNA of isolated clones rescued by PCR. Using two rounds of APEx, the inventors demonstrate that the affinity of a neutralizing antibody to the *Bacillus anthracis* protective antigen (PA) was improved over 120-fold, exhibiting a final $K_D$=35 pM.

In one embodiment of the invention, target molecules are labeled with fluorescent dyes. Thus, bacterial clones expressing polypeptides that recognize the target molecule bind to the fluorescently labeled target and in turn become fluorescent. The fluorescent bacteria expressing the desired binding proteins can then be enriched from the population using automated techniques such as flow cytometry.

The polypeptide library can be attached to the periplasmic face of the inner membrane of *E. coli* or other Gram negative bacteria via fusion to an inner membrane anchor polypeptide. One anchor that can be used comprises the first six amino acids of the NlpA (New Lipoprotein A) gene of *E coli*. However, other single transmembrane or polytropic membrane proteins or peptide sequences can also be used for anchoring purposes.

One benefit of the technique is that anchoring candidate binding polypeptides to the periplasmic face of the inner membrane allows the permeabilization of the bacterial outer membrane, which would normally limit the accessibility of the polypeptides to labeled target molecules. The anchoring of the binding polypeptide to the periplasmic face of the membrane prevents it from being released from the cell when the outer membrane is compromised. The technique can thus be used for the isolation of large binding polypeptides and ligands, including antibodies and other binding proteins from combinatorial libraries. The technique not only provides a high signal-to-noise ratio, but also allows the isolation of polypeptide or antibody binders to very large antigen molecules. Because the method allows selection of targets of greater size, there is the potential for use in the selection of targets such as specific antigen markers expressed on cells including tumor cells such as melanoma or other specific types of tumor cells. Tumor specific antibodies have shown great promise in the treatment of cancer.

The periplasm comprises the space defined by the inner and outer membranes of a Gram-negative bacterium. In wild-type *E. coli* and other Gram negative bacteria, the outer membrane serves as a permeability barrier that severely restricts the diffusion of molecules greater than 600 Da into the periplasmic space (Decad and Nikado, 1976). Conditions that increase the permeability of the outer membrane, allowing larger molecules to diffuse in the periplasm, have two deleterious effects in terms of the ability to screen libraries: (a) the cell viability is affected to a significant degree and (b) the diffusion of molecules into the cell is accompanied by the diffusion of proteins and other macromolecules.

The inventors, by anchoring candidate binding polypeptides to the outer (periplasmic) side of the inner membrane, or expressing candidate binding polypeptides in soluble form in the periplasm, have identified techniques that allow fluorescent conjugates of ligands and polypeptides to pass the outer membrane and bind to candidate binding proteins and remain bound to the inner membrane. Therefore, in bacterial cells expressing recombinant polypeptides with affinity for the ligand, the labeled ligand bound to the binding protein can be detected, allowing the bacteria to be isolated from the rest of the library. Where fluorescent labeling of the target ligand is used, cells may efficiently be isolated by flow cytometry (fluorescence activated cell sorting (FACS)). With this approach, existing libraries of expressed fusion proteins in bacteria can be easily tested for ligand binding without the need for subcloning into a phage or outer cell surface display systems.

Periplasmic expression may also be carried out in accordance with the invention by expression in soluble form. Techniques for soluble expression in the periplasm and screening of candidate binding proteins that may be used in accordance with the invention are described in detail in U.S. patent application Ser. No. 09/699,023, filed Oct. 27, 2000, the entire disclosure of which is specifically incorporated herein by reference.

I. Anchored Periplasmic Expression

Prior art methods of both phage display and bacterial cell surface display suffer from a limitation in that the protein is required, by definition, to be physically displayed on the outer surface of the vehicle used, to allow unlimited access to the targets (immobilized for phage or fluorescently conjugated ligands for flow cytometry) (U.S. Pat. No. 5,223,409, the disclosure of which is specifically incorporated herein by reference in its entirety). However, certain proteins are known to be poorly displayed on phage (Maenaka et al., 1996; Corey et al., 1993) and the toxic effects of outer cell surface display have been treated at length (Daugherty et al., 1999). Further, there is no lipopolysaccharide to interfere with binding on the inner membrane.

Herein, the inventors have described a technique in which binding proteins can be expressed on the periplasmic face of the inner membrane as fusion proteins yet still be accessible to relatively large ligands. As used herein, the term "binding polypeptide" includes not only antibodies, but also fragments of antibodies, as well as any other peptides, including proteins potentially capable of binding a given target molecule. The antibody or other binding peptides may be expressed with the invention as fusion polypeptides with polypeptides capable of serving as anchors to the periplasmic face of the inner membrane. Such a technique may be termed "Anchored Periplasmic Expression" or "APEx".

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations (Mg2+ and Ca2+) and link each other electrostatically to form a highly ordered quasi-crystalline ordered "tiled roof" on the surface (Labischinski et al., 1985). The membrane forms a very strict permeability barrier allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Naeke, 1976; Nikaido and Nakae, 1979; Nikaido and Vaara, 1985). With such strict physiological regulation of access by molecules to the periplasm it may appear, at first glance, inconceivable that APEx should work unless the ligands employed are at or below the 650 Da exclusion limit or are analogues of normally permeant compounds. However, the inventors have shown that ligands greater than 2000 Da in size can diffuse into the periplasm without disruption of the periplasmic membrane. Such diffusion can be aided by one or more treatments of a bacterial cell, thereby rendering the outer membrane more permeable, as is described herein below.

II. Anchor-less Display Library Screening

Prior art methods of both phage display and bacterial cell surface display suffer from a limitation in that the protein is required, by definition, to be physically displayed on the surface of the vehicle used, to allow unlimited access to the targets (immobilized for phage or fluorescently conjugated ligands for FACS) (U.S. Pat. No. 5,223,409, the disclosure of which is specifically incorporated herein by reference in its entirety). Certain proteins are known to be poorly displayed on phage (Maenaka et al., 1996; Corey et al., 1993) and the toxic effects of cell surface display have been treated at length (Daugherty et al., 1999). The proteins to be displayed also need to be expressed as fusion proteins, which may alter their function. The selection constraints imposed by any display system may, therefore, limit the application to relatively small and "simple" proteins and deny access to a multitude of large and complex multisubunit species. The latter are very likely to be incapable of partaking efficiently in the complex process of phage assembly termination or outer-membrane translocation without very serious effects on host cell viability.

Herein, conditions are described whereby expressed binding proteins, for example, an antibody, may be targeted to the periplasmic compartment of E. coli and yet are amenable to binding ligands and peptides. As used herein, the term "binding protein" includes not only antibodies, but also fragments of antibodies, as well as any other polypeptide or protein potentially capable of binding a given target molecule. As well as being anchored, the antibody or other binding proteins may be expressed with the invention directly and not as fusion proteins. Such a technique may be termed "anchor-less-display" (ALD). To understand how it may work, one needs to be aware of the location in which it functions.

The periplasmic compartment is contained between the inner and outer membranes of Gram negative cells (see, e.g., Oliver, 1996). As a sub-cellular compartment, it is subject to variations in size, shape and content that accompany the growth and division of the cell. Within a framework of peptidoglycan heteroploymer is a dense mileau of periplasmic proteins and little water, lending a gel-like consistency to the compartment (Hobot et al., 1984; van Wielink and Duine, 1990). The peptidoglycan is polymerized to different extents depending on the proximity to the outer membrane, close-up it forms the murein sacculus that affords cell shape and resistance to osmotic lysis.

The outer membrane (see Nikaido, 1996) is composed of phospholipids, porin proteins and, extending into the medium, lipopolysaccharide (LPS). The molecular basis of outer membrane integrity resides with LPS ability to bind divalent cations (Mg2+ and Ca2+) and link each other electrostatically to form a highly ordered quasi-crystalline ordered "tiled roof" on the surface (Labischinski et al., 1985). The membrane forms a very strict permeability barrier of allowing passage of molecules no greater than around 650 Da (Burman et al., 1972; Decad and Nikaido, 1976) via the porins. The large water filled porin channels are primarily responsible for allowing free passage of mono and disaccharides, ions and amino acids in to the periplasm compartment (Naeke, 1976; Nikaido and Nakae, 1979; Nikaido and Vaara, 1985). With such strict physiological regulation of access by molecules to the periplasm it may appear, at first glance, inconceivable that ALD should work unless the ligands employed are at or below the 650 Da exclusion limit or are analogues of normally permeant compounds. However, the inventors have shown that ligands can diffuse into the periplasm for ALD. Such diffusion can be aided by one or more treatments of a bacterial cell, thereby rendering the outer membrane more permeable, as is described herein below.

III. Permeabilization of the Outer Membrane

In one embodiment of the invention, methods are employed for increasing the permeability of the outer membrane to one or more labeled ligand. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Such a mechanism has been adopted to selectively label the periplasmic loops of a cytoplasmic membrane protein in vivo with a polymyxin B nonapeptide (Wada et al., 1999). Also, certain long chain phosphate polymers (100 Pi) appear to bypass the normal molecular sieving activity of the outer membrane altogether (Rao and Torriani, 1988).

Conditions have been identified that lead to the permeation of ligands into the periplasm without loss of viability or release of the expressed proteins from the cells, but the invention may be carried out without maintenance of the outer membrane. By anchoring candidate binding polypeptides to the outer side of the inner (cytoplasmic) membrane using fusion polypeptides, the need for maintenance of the outer membrane (as a barrier to prevent the leakage of the biding protein from the cell) to detect bound labeled ligand is removed. As a result, cells expressing binding proteins anchored to the outer (periplasmic) face of the cytoplasmic membrane can be fluorescently labeled simply by incubating with a solution of fluorescently labeled ligand in cells that either have a partially permeabilized membrane or a nearly completely removed outer membrane.

The permeability of the outer membrane of different strains of bacterial hosts can vary widely. It has been shown previously that increased permeability due to OmpF overexpression was caused by the absence of a histone like protein resulting in a decrease in the amount of a negative regulatory mRNA for OmpF translation (Painbeni et al., 1997). Also, DNA replication and chromosomal segregation is known to rely on intimate contact of the replisome with the inner membrane, which itself contacts the outer membrane at numerous points. A preferred host for library screening applications is *E. coli* ABLEC strain, which additionally has mutations that reduce plasmid copy number.

The inventors have also noticed that treatments such as hyperosmotic shock can improve labeling significantly. It is known that many agents including, calcium ions (Bukau et al., 1985) and even Tris buffer (Irvin et al., 1981) alter the permeability of the outer-membrane. Further, the inventors found that phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt and phage, a high degree of permeability was achieved (Daugherty et al., 1999). Cells comprising anchored binding polypeptides bound to fluorescently labeled ligands can then be easily isolated from cells that express binding proteins without affinity for the labeled ligand using flow cytometry or other related techniques. However, it will typically be desired to use less disruptive techniques in order to maintain the viability of cells. EDTA and Lysozyme treatments may also be useful in this regard.

IV. Anchored Periplasmic Expression

In one embodiment of the invention, bacterial cells are provided expressing fusion polypeptides on the outer face of the inner membrane. Such a fusion polypeptide may comprise a fusion between a candidate binding polypeptide and a polypeptide serving as an anchor to the outer face of the inner membrane. It will be understood to those of skill in the art that additional polypeptide sequences may be added to the fusion polypeptide and not depart from the scope of the invention. One example of such a polypeptide is a linker polypeptide serving to link the anchor polypeptide and the candidate binding polypeptide. The general scheme behind the invention comprises the advantageous expression of a heterogeneous collection of candidate binding polypeptides.

Anchoring to the inner membrane may be achieved by use of the leader peptide and the first six amino acids of an inner membrane lipoprotein. One example of an inner membrane lipoprotein is NlpA (new lipoprotein A). The first six amino acid of NlpA can be used as an N terminal anchor for protein to be expressed to the inner membrane. NlpA was identified and characterized in *Escherichia coli* as a non-essential lipoprotein that exclusively localizes to the inner membrane (Yu, 1986; Yamaguchi, 1988).

As with all prokaryotic lipoproteins, NlpA is synthesized with a leader sequence that targets it for translocation across the inner membrane via the Sec pathway. Once the precursor protein is on the outer side of the inner membrane the cysteine residue of the mature lipoprotein forms a thioether bond with diacylglyceride. The signal peptide is then cleaved by signal peptidase II and the cysteine residue is aminoacylated (Pugsley, 1993). The resulting protein with its lipid modified cysteine on its N terminus can then either localize to the inner or outer membrane. It has been demonstrated that this localization is determined by the second amino acid residue of the mature lipoprotein (Yamaguchi, 1988). Aspartate at this position allows the protein to remain anchored via its N terminal lipid moiety to the inner membrane, whereas any other amino acid in the second position generally directs the lipoprotein to the outer membrane (Gennity and Inouye, 1992). This is accomplished by proteins LolA, LolB and the ATP dependant ABC transporter complex LolCDE (Yakushi, 2000, Masuda 2002). NlpA has aspartate as its second amino acid residue and therefore remains anchored within the inner membrane.

It has been reported that by changing amino acid 2 of lipoproteins to an Aspartate (D) will target them to reside in the inner membrane (Yakushi, 1997). Therefore all lipoproteins in *E. coli* (and potentially other Gram negative bacteria) can be anchor sequences. All that is required is a signal sequence and an aspartate at amino acid 2 position. This construct could be designed artificially using an artificial sec signal sequence followed by the sec cleavage region and coding for cysteine as amino acid 1 and aspartate as amino acid 2 of the mature protein. Transmembrane proteins could also potentially be used as anchor sequences although this will require a larger fusion construct.

Examples of anchors that may find use with the invention include lipoproteins, Pullulanase of *K. pneumoniae*, which has the CDNSSS mature lipoprotein anchor, phage encoded celB, and *E. coli* acrE (envC). Examples of inner membrane proteins which can be used as protein anchors include: AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, PhnM, LacY, SecY, TolC, Dsb,B, DsbD, TonB, TatC, CheY, TraB, ExbD, ExbB and Aas. Further, a single transmembrane loop of any cytoplasmic protein can be used as a membrane anchor.

The preparation of diverse populations of fusion proteins in the context of phage display is known (see, e.g., U.S. Pat. No. 5,571,698). Similar techniques may be employed with the instant invention by linking the protein of interest to an anchor for the periplasmic face of the cytoplasmic membrane instead of, for example, the amino-terminal domain of the gene III coat protein of the filamentous phage M13, or another surface-associated molecule. Such fusions can be mutated to form a library of structurally related fusion proteins that are expressed in low quantity on the periplasmic face of the cytoplasmic membrane in accordance with the invention. As such, techniques for the creation of heterogeneous collections of candidate molecules which are well known to those of skill in the art in conjunction with phage display, can be adapted for use with the invention. Those of skill in the art will recognize that such adaptations will include the use of bacterial elements for expression of fusion proteins anchored to the periplasmic face of the inner membrane, including, promoter, enhancers or leader sequences. The current invention provides the advantage relative to phage display of not requiring the use of phage or expression of molecules on the outer cell surface, which may be poorly expressed or may be deleterious to the host cell.

Examples of techniques that could be employed in conjunction with the invention for creation of diverse candidate binding proteins and/or antibodies include the techniques for expression of immunoglobulin heavy chain libraries described in U.S. Pat. No. 5,824,520. In this technique, a single chain antibody library is generated by creating highly divergent, synthetic hypervariable regions. Similar techniques for antibody display are given by U.S. Pat. No. 5,922,545. These sequences may then be fused to nucleic acids encoding an anchor sequence for the periplasmic face of the inner membrane of Gram negative bacteria for the expression of anchored fusion polypeptides.

Methods for creation of fusion proteins are well known to those of skill in the art (see, for example, U.S. Pat. No. 5,780,279). One means for doing so comprises constructing a gene fusion between a candidate binding polypeptide and an anchor sequence and mutating the binding protein encoding nucleic acid at one or more codons, thereby generating a family of mutants. The mutated fusion proteins can then be expressed in large populations of bacteria. Those bacteria in which a target ligand binds, can then be isolated and the corresponding nucleic acid encoding the binding protein can be cloned.

V. Screening Candidate Molecules

The present invention provides methods for identifying molecules capable of binding a target ligand. The binding polypeptides screened may comprise large libraries of diverse candidate substances, or, alternatively, may comprise particular classes of compounds selected with an eye towards structural attributes that are believed to make them more likely to bind the target ligand. In one embodiment of the invention, the candidate binding protein is an antibody, or a fragment or portion thereof. In other embodiments of the invention, the candidate molecule may be another binding protein.

To identify a candidate molecule capable of binding a target ligand in accordance with the invention, one may carry out the steps of: providing a population of Gram negative bacterial cells comprising fusion proteins between candidate binding polypeptides and a sequence anchored to the periplasmic face of the inner membrane; admixing the bacteria and at least a first labeled target ligand capable of contacting the candidate binding polypeptide and identifying at least a first bacterium expressing a molecule capable of binding the target ligand.

In the aforementioned method, the binding between the anchored candidate binding protein and the labeled ligand will prevent diffusing out of the cell. In this way, molecules of the labeled ligand can be retained in the periplasm of the bacterium. Alternatively, the periplasm can be removed, whereby the anchoring will cause retention of the bound candidate molecule. The labeling may then be used to isolate the cell expressing a binding polypeptide capable of binding the target ligand, and in this way, the gene encoding the binding polypeptide isolated. The molecule capable of binding the target ligand may then be produced in large quantities using in vivo or ex vivo expression methods, and then used for any desired application, for example, for diagnostic or therapeutic applications, as described below.

As used herein the term "candidate molecule" or "candidate polypeptide" refers to any molecule or polypeptide that may potentially have affinity for a target ligand. The candidate substance may be a protein or fragment thereof, including a small molecule such as synthetic molecule. The candidate molecule may in one embodiment of the invention, comprise an antibody sequence or fragment thereof. Such sequences may be particularly designed for the likelihood that they will bind a target ligand.

Binding polypeptides or antibodies isolated in accordance with the invention also may help ascertain the structure of a target ligand. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen. On the other hand, one may simply acquire, from various commercial sources, small molecule libraries that are believed to meet the basic criteria for binding the target ligand. Such libraries could be provided by way of nucleic acids encoding the small molecules or bacteria expressing the molecules.

A. Cloning of Binding Protein Coding Sequences

The binding affinity of an antibody or other binding protein can, for example, be determined by the Scatchard analysis of Munson & Pollard (1980). After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein).

Once isolated, the antibody or binding protein DNA may be placed into expression vectors, which can then transfected into host cells such as simian COS cells, Chinese hamster ovary (CHO) cells, or myeloma cells that do not otherwise produce immunoglobulin protein, to obtain the synthesis of binding protein in the recombinant host cells. The DNA also may be modified, for example, by substituting the coding sequence for human heavy and light chain constant domains in place of the homologous murine sequences (Morrison, et al., 1984), or by covalently joining to the immunoglobulin coding sequence all or part of the coding sequence for a non-immunoglobulin polypeptide. In that manner, "chimeric" or "hybrid" binding proteins are prepared that have the desired binding specificity.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for the target ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

B. Maximization of Protein Affinity for Ligands

In a natural immune response, antibody genes accumulate mutations at a high rate (somatic hypermutation). Some of the changes introduced will confer higher affinity, and B cells displaying high-affinity surface immunoglobulin. This natural process can be mimicked by employing the technique known as "chain shuffling" (Marks et al., 1992). In this method, the affinity of "primary" human antibodies obtained in accordance with the invention could be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large antibody repertoires was described by Waterhouse et al., (1993), and the isolation of a high affinity human antibody directly from such large phage library was reported by Griffith et al., (1994). Gene shuffling also can be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by the phage display technique is replaced with a repertoire of human V domain genes, creating rodent-human chimeras. Selection of the antigen results in isolation of human variable regions capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

C. Labeled Ligands

In one embodiment of the invention, an antibody or binding protein is isolated which has affinity for a labeled ligand. By permeabilization and/or removal of the periplasmic membrane of a Gram negative bacterium in accordance with the invention, labeled ligands of potentially any size could be screened. In the absence of removal of the periplasmic membrane, it will typically be preferable that the labeled ligand is less that 50,000 Da in size in order to allow efficient diffusion of the ligand across the bacterial periplasmic membrane.

As indicated above, it will typically be desired in accordance with the invention to provide a ligand which has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels which could be used with the invention include, but are not limited to, enzymes, radiolabels, haptens, fluorescent labels, phosphorescent molecules, chemiluminescent molecules, chromophores, luminescent molecules, photoaffinity molecules, colored particles or ligands, such as biotin.

In one embodiment of the invention, a visually-detectable marker is used such that automated screening of cells for the label can be carried out. In particular, fluorescent labels are beneficial in that they allow use of flow cytometry for isolation of cells expressing a desired binding protein or antibody. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances and substances for X-ray imaging. Types of fluorescent labels that may be used with the invention will be well known to those of skill in the art and include, for example, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Magnetic screening techniques are well known to those of skill in the art (see, for example, U.S. Pat. No. 4,988,618, U.S. Pat. No. 5,567,326 and U.S. Pat. No. 5,779,907). Examples of paramagnetic ions that could be used as labels in accordance with such techniques include ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts include but are not limited to lanthanum (III), gold (III), lead (II), and especially bismuth (III).

Another type of ligand conjugate contemplated in the present invention are those where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups also may be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide-binding proteins in crude cell extracts (Owens & Haley, 1987; Atherton et al., 1985). The 2- and 8-azido nucleotides have also been used to map nucleotide-binding domains of purified proteins (Khatoon et al., 1989; King et al., 1989; and Dholakia et al., 1989) and may be used as ligand binding agents.

Labeling can be carried out by any of the techniques well known to those of skill in the art. For instance, ligands can be labeled by contacting the ligand with the desired label and a chemical oxidizing agent such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). Ligands also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

The ability to specifically label periplasmic expressed proteins with appropriate fluorescent ligands also has applications other than library screening. Specifically labeling with fluorescent ligands and flow cytometry can be used for monitoring production during protein manufacturing. While flow cytometry has been used previously for the analysis of bacterial cells, it has not been used for the specific labeling and quantitation of periplasmic proteins. However, a large number of commercially important proteins including IGF-1 several interleukins, enzymes such as urokinase-type plasminogen activator, antibody fragments, inhibitors (e.g., Bovine pancreatic trypsin inhibitor) are expressed in recombinant bacteria in a form secreted into the periplasmic space. The level of production of such proteins within each cell in a culture can be monitored by utilizing an appropriate fluorescent ligand and flow cytometric analysis, according to the techniques taught by the present invention.

Generally, monitoring protein expression requires cell lysis and detection of the protein by immunological techniques or following chromatographic separation. However, ELISA or western blot analysis is time-consuming and does not provide information on the distribution of expression among a cell population and cannot be used for on-line monitoring (Thorstenson et al., 1997; Berrier et al., 2000). In contrast, FACS labeling is rapid and simple and can well be applied to online monitoring of industrial size fermentations of recombinant proteins expressed in Gram-negative bacteria. Similarly, the invention could be used to monitor the production of a particular byproduct of a biological reaction. This also could be used to measure the relative concentration or specific activity of an enzyme expressed in vivo in a bacterium or provided ex vivo.

Once a ligand-binding protein, such as an antibody, has been isolated in accordance with the invention, it may be desired to link the molecule to at least one agent to form a conjugate to enhance the utility of that molecule. For example, in order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Techniques for labeling such a molecule are known to those of skill in the art and have been described herein above.

Labeled binding proteins such as antibodies which have been prepared in accordance with the invention may also then be employed, for example, in immunodetection methods for binding, purifying, removing, quantifying and/or otherwise generally detecting biological components such as protein(s), polypeptide(s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; and De Jager R et al., 1993, each incorporated herein by reference. Such techniques include binding assays such as the various types of enzyme linked immunosorbent assays (ELISAs) and/or radioimmunoassays (RIA) known in the art.

The ligand-binding molecules, including antibodies, prepared in accordance with the present invention may also, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

VI. Automated Screening with Flow Cytometry

In one embodiment of the invention, fluorescence activated cell sorting (FACS) screening or other automated flow cytometric techniques may be used for the efficient isolation of a bacterial cell comprising a labeled ligand bound to a candidate molecule and linked to the outer face of the cytoplasmic membrane of the bacteria. Instruments for carrying out flow cytometry are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry that could include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of the disclosures of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

VII. Nucleic Acid-Based Expression Systems

Nucleic acid-based expression systems may find use, in certain embodiments of the invention, for the expression of recombinant proteins. For example, one embodiment of the invention involves transformation of Gram negative bacteria with the coding sequences of fusion polypeptides comprising a candidate antibody or other binding protein having affinity for a selected ligand and the expression of such molecules on the cytoplasmic membrane of the Gram negative bacteria. In other embodiments of the invention, expression of such coding sequences may be carried, for example, in eukaryotic host cells for the preparation of isolated binding proteins having specificity for the target ligand. The isolated protein could then be used in one or more therapeutic or diagnostic applications.

A. Methods of Nucleic Acid Delivery

Certain aspects of the invention may comprise delivery of nucleic acids to target cells. For example, bacterial host cells may be transformed with nucleic acids encoding candidate molecules potentially capable binding a target ligand, In particular embodiments of the invention, it may be desired to target the expression to the cytoplasmic membrane of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into such a cell, or even an organelle thereof. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and Ser. No. 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

1. Electroporation

In certain embodiments of the present invention, a nucleic acid is introduced into a cell via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

2. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

B. Vectors

Vectors may find use with the current invention, for example, in the transformation of a Gram negative bacterium with a nucleic acid sequence encoding a candidate polypeptide which one wishes to screen for ability to bind a target ligand. In one embodiment of the invention, an entire heterogeneous "library" of nucleic acid sequences encoding target polypeptides may be introduced into a population of bacteria, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous," or "heterologous", which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art may construct a vector through standard recombinant techniques, which are described in Maniatis et al., 1988 and Ausubel et al., 1994, both of which references are incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. One example of such promoter that may be used with the invention is the *E. coli* arabinose promoter. Those of skill in the art of molecular biology generally are familiar with the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels.

Terminators contemplated for use in the invention include any known terminator of transcription described herein or known to one of ordinary skill in the art, including but not limited to, for example, rhp dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram negative bacterial cell. These bacteria are suited for use with the invention in that they posses a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp. The Gram negative bacterial cell may be still further defined as bacterial cell which has been transformed with the coding sequence of a fusion polypeptide comprising a candidate binding polypeptide capable of binding a selected ligand. The polypeptide is anchored to the outer face of the cytoplasmic membrane, facing the periplasmic space, and may comprise an antibody coding sequence or another sequence. One means for expression of the polypeptide is by attaching a leader sequence to the polypeptide capable of causing such directing.

Numerous prokaryotic cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for bacteriophage.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System and an *E. coli* expression system.

E. Candidate Binding Proteins and Antibodies

In certain aspects of the invention, candidate antibodies or other recombinant polypeptides, including proteins and short peptides potentially capable of binding a target ligand are expressed on the cytoplasmic membrane of a host bacterial cell. By expression of a heterogeneous population of such antibodies or other binding polypeptides, those antibodies having a high affinity for a target ligand may be identified. The identified antibodies may then be used in various diagnostic or therapeutic applications, as described herein.

As used herein, the term "antibody" is intended to refer broadly to any immunologic binding agent such as IgG, IgM, IgA, IgD and IgE. The term "antibody" is also used to refer to any antibody-like molecule that has an antigen binding region, and includes antibody fragments such as Fab', Fab, F(ab')$_2$, single domain antibodies (DABs), Fv, scFv (single chain Fv), and engineering multivalent antibody fragments such as dibodies, tribodies and multibodies. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Once an antibody having affinity for a target ligand is identified, the antibody or ligand binding polypeptide may be purified, if desired, using filtration, centrifugation and various chromatographic methods such as HPLC or affinity chromatography. Fragments of such polypeptides, including antibodies, can be obtained from the antibodies so produced by methods which include digestion with enzymes, such as pepsin or papain, and/or by cleavage of disulfide bonds by chemical reduction. Alternatively, antibody or other polypeptides, including protein fragments, encompassed by the present invention can be synthesized using an automated peptide synthesizer.

A molecular cloning approach comprises one suitable method for the generation of a heterogeneous population of candidate antibodies that may then be screened in accordance with the invention for affinity to target ligands. In one embodiment of the invention, combinatorial immunoglobulin phagemid can be prepared from RNA isolated from the spleen of an animal. By immunizing an animal with the ligand to be screened, the assay may be targeted to the particular antigen. The advantages of this approach over conventional techniques are that approximately $10^4$ times as many antibodies can be produced and screened in a single round, and that new specificities are generated by H and L chain combination which further increases the chance of finding appropriate antibodies.

VIII. Manipulation and Detection of Nucleic Acids

In certain embodiments of the invention, it may be desired to employ one or more techniques for the manipulation, isolation and/or detection of nucleic acids. Such techniques may include, for example, the preparation of vectors for transformation of host cells as well as methods for cloning selected nucleic acid segments from a transgenic cell. Methodology for carrying out such manipulations will be well known to those of skill in the art in light of the instant disclosure.

Nucleic acids used as a template for amplification may be isolated from cells, tissues or other samples according to standard methodologies (Sambrook et al., 1989). In certain embodiments, analysis may be performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to a selected nucleic acid sequence are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
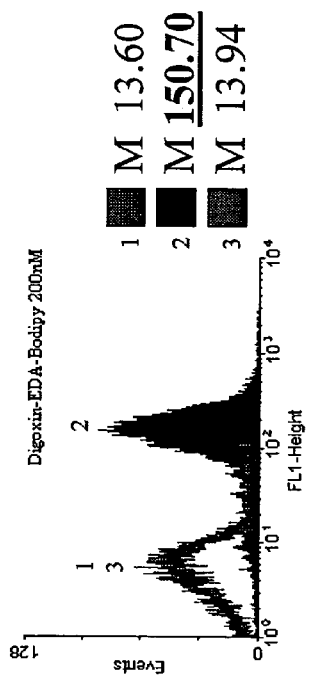
Figure 1C:
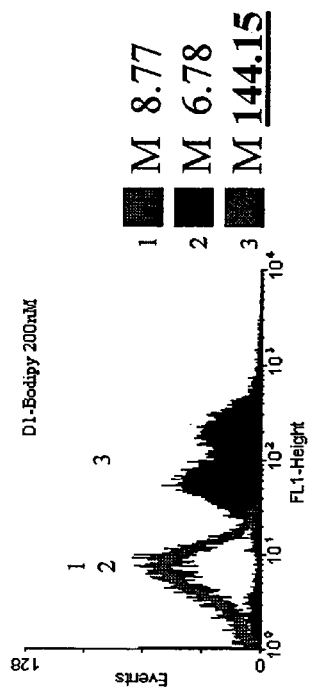

Demonstration of Anchored Periplasmic Expression to Target Small Molecules and Peptides The ability of scFvs displayed by APEx to target small molecules and peptides is shown in FIGS. 1A–1B and in FIG. 1C, respectively. Three cultures of *Escherichia coli* containing fusions of the first six amino acids of NlpA (to serve as a inner membrane targeting sequence for APEx analysis) to either an anti-methamphetamine, anti-digoxin, or anti-peptide scfv were grown up and induced for protein expression as described below. Cells of each construct were then labeled in 5×PBS buffer with 200 nM concentrations of methamphetamine-FL (FIG. 1A), digoxigenin-bodipy (FIG. 1B), or 200 nM peptide(18 mer)-BodipyFL (FIG. 1C). The data presented shows a histogram representation of 10,000 events from each of the labeled cell cultures. The results demonstrate the ability of scfvs displayed by APEx to bind to their specific antigen conjugated fluorophore, with minimal crossreactivity to non-specific ligands.

Example 2

Demonstration of Recognition of Ab Fragments by Anchored Periplasmic Expression

To demonstrate that the scFv is accessible to larger proteins, it was first demonstrated that polyclonal antibody serum against human Ab fragments or mouse Ab fragments would recognize scFvs derived from each displayed on the *E. coli* inner membrane by anchored periplasmic expression. *Escherichia coli* expressing a mouse derived scFv via anchored periplasmic expression (FIG. 2A) or expressing a human derived scFv via anchored periplasmic expression (FIG. 2B) were labeled as described below with either anti-mouse polyclonal IgG (H+L)-Alexa-FL or anti-human polyclonal IgG (Fab)-FITC. Results (FIGS. 2A, 2B) in the form of histogram representations of 10000 events of each demonstrated that the anti-human polyclonal (approximately 150 kDa in size) recognized the human derived scFv specifically while the anti-mouse polyclonal (150 kDa) recognized the mouse derived scFv.

Example 3

Demonstration of the Ability of scFvs Displayed by Anchored Periplasmic Expression to Specifically Bind Large Antigen Conjugated Fluorophores To demonstrate the ability of scFvs displayed via anchored periplasmic expression to specifically bind to large antigen conjugated fluorophores, *E. coli* were induced and labeled as described below expressing, via anchored periplasmic expression, an anti-protective antigen (PA) scFv (PA is one component of the anthrax toxin: a 83 kDa protein) or an anti-digoxigenin scFv. Histogram data of 10,000 events demonstrated specific binding to a PA-Cy5 antigen conjugated flourophore as compared to the cells expressing the an anti-digoxigenin scFv (FIG. 3A). To further illustrate this point, digoxigenin was coupled to phycoerythrin (PE), a 240 kDa fluorescent protein. Cells were labeled with this conjugate as described below. It was found that *E. coli* (10,000 events) expressing the anti-digoxigenin scFv via anchored periplasmic expression were labeled with the large PE-digoxigenin conjugate while those expressing a non-specific scFv via anchored periplasmic expression show little fluorescence (FIG. 3B).

Example 4

Figure 4:
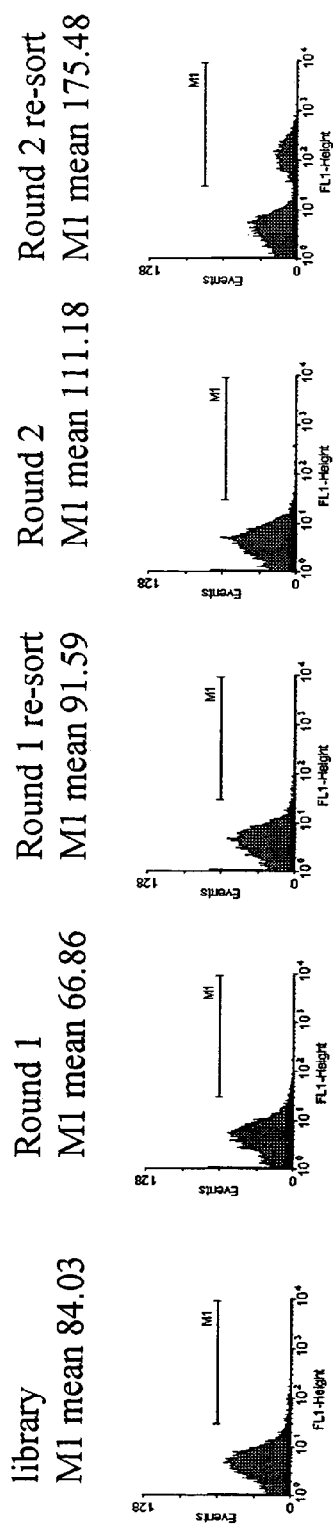
FIG. 4: Maturation of methamphetamine binding scFv for Meth-FL probe.

Demonstration of Selecting for Improved scFv Variants from a Library of scFvs by Flow Cytometric Selection Scans were carried out of polyclonal *Escherichia coli* expressing, via anchored periplasmic expression, a mutagenic library of an scFv with affinity to methamphetamine. Through two rounds of sorting and re-sorting using a Methamphetamine conjugated fluorophore, a sub-population of the library was isolated. (FIG. 4)

Figure 5:
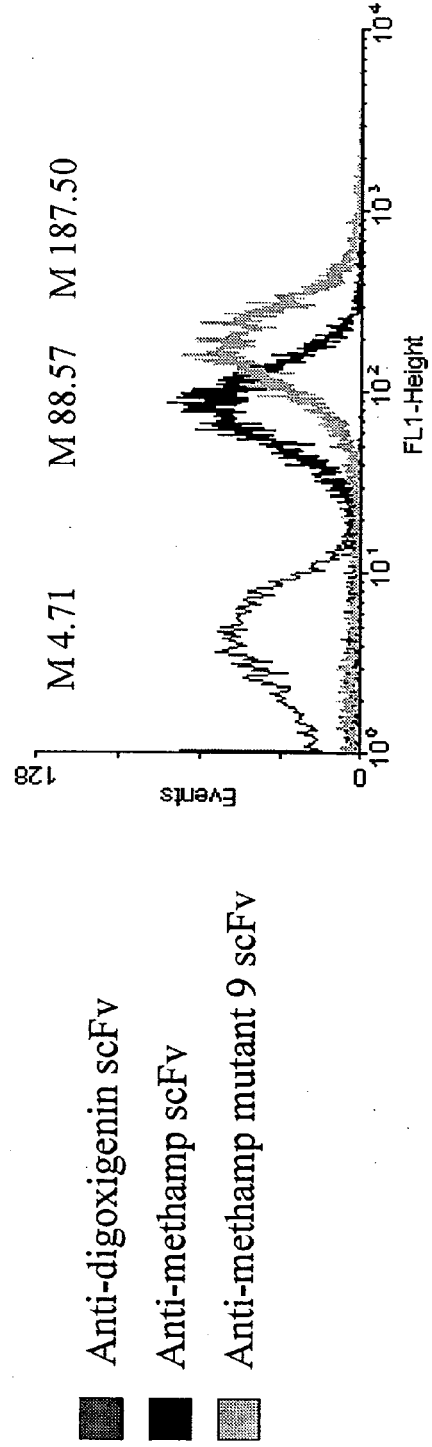
FIG. 5: Analysis of clone designated mutant 9 with higher mean FL signal than the parent anti-methamphetamine scFv. The scFvs expressed via anchored periplasmic expression are as indicated.
Figure 6:
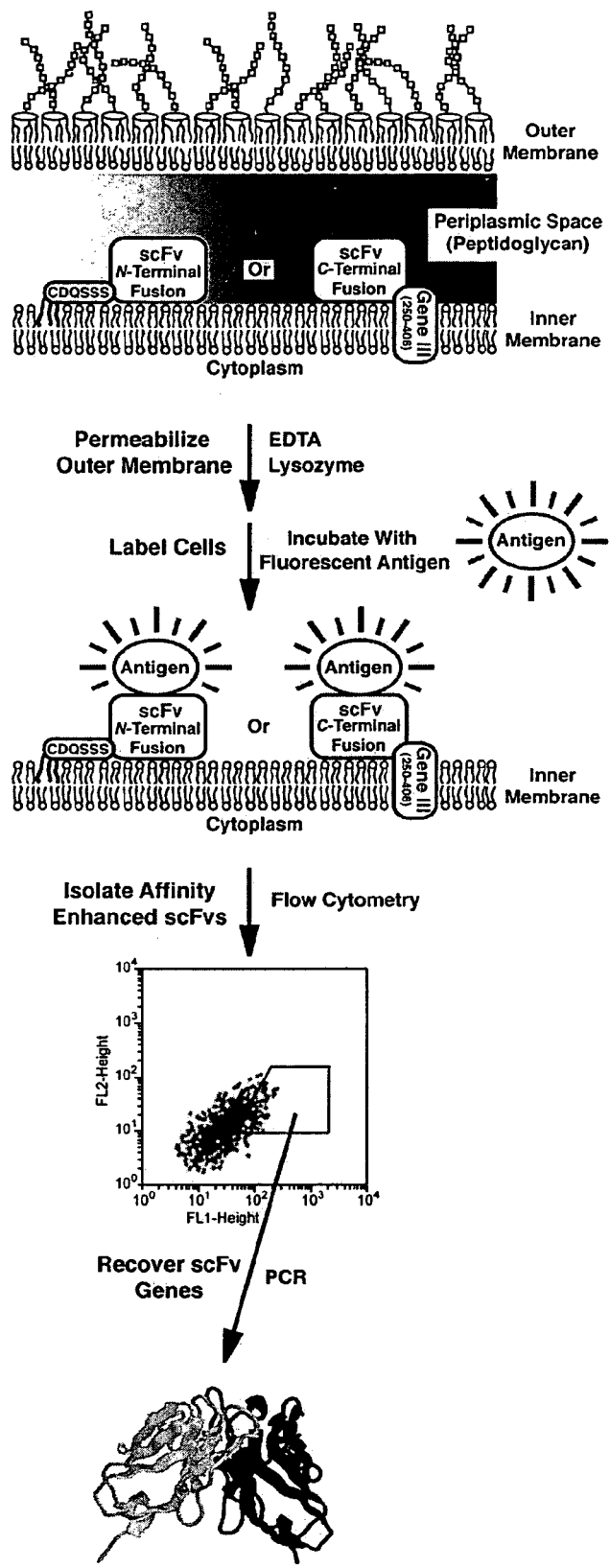
FIG. 6: A schematic diagram showing the principle of Anchored Periplasmic Expression (APEx) for the flow cytometry based isolation of high affinity antibody fragments.

Individual clones from this library were labeled with the same Methamphetamine flourophore and analyzed as described below. Shown in FIG. 5 is an example of a clone, designated mutant 9, that had a higher mean FL signal than the parent anti-methamphetamine scFv.

Example 5

Materials and Methods

A. Vector Construction

The leader peptide and first six amino acids of the mature NlpA protein were generated by whole cell PCR (Perken Elmer) on XL1-blue *Escherichia coli*, (Stratagene) using primers BRH#08 5' GAAGGAGATATACATATGAAACTGACAACACATCATCTA 3' and (SEQ ID NO:6)

BRH#9 5' CTGGGCCATGGCCGGCTGGGCCTCGCTGCTACTCTGGTCGCAACC 3', (SEQ ID NO:7)

VENT polymerase (New England Biolabs) and dNTPs (Roche). This was then cut with Nde1 and Sfi1 restriction endonucleases and cloned between a lac promoter and a multiple cloning site (MCS) in a *E. coli* expression vector with the following elements down stream of the MCS: myc and his tag, Cm resistance marker, colE1 origin and lac I. ScFvs of interest were then cloned into the MCS and the vector was transformed into AbleC *E. coli* (Stratagene).

B. Expression

*E. coli* cells are inoculated in TB media+2% glucose and 30 mg/l chloramphenicol to an OD600 of 0.1. Cells are grown for 2 hours at 37 C and then cooled to 25 C for 30 minutes. They are then induced at 25 C with 1 mM IPTG for 4 hrs.

Mutagenic libraries of scFv sequences were constructed using mutagenic PCR methods as described by Fromant M, et al. (1995) utilizing the original scFv sequence as a template. These mutagenic products were then cloned into the above mentioned APEx expression vector, transformed into ABLEC *E. coli* and plated on agar plates with SOC media containing 2% glucose and 30 ug/ml chloramphenicol. Following overnight incubation at 30 C, the *E. coli* were scraped from the plates, frozen in 15% glycerol aliquots and stored at −80 C for future flow cytometric sorting.

C. Labeling Strategies

Following induction, cells are either incubated in 5×PBS with 200 nM probe for 45 minutes or are resuspended in 350 μl of 0.75 M sucrose, 100 mM Tris. 35 μl of lysozyme at 10 mg/ml is then added followed by 7001 μl of 1 mM EDTA added dropwise with gentle shaking. This is allowed to sit on ice for 10 min followed by the addition of 50 μl of 0.5 M MgCl2. After an additional 10 minutes on ice the suspension is centrifuged at 13,200 g for 1 minute, decanted and resuspended in 500 μl 1×PBS. The cells are then labeled with 200 nM of probe for 45 minutes, and are then analyzed by flow cytometry and selected for improved fluorescence.

D. Strains and Plasmids

Strain ABLE™C (Stratagene) was used for screening with APEx. *E. coli* strains TG1 and HB2151 were provided with the Griffin library. ABLE™C and ABLE™K were purchased from Stratagene and helper phage M13K07 from Pharmacia. A positive control for FACS analysis of a phage display vehicle was constructed by replacing a pre-existing scFv in pHEN2 with the 26.10 scFv to create pHEN2.dig. The negative control was pHEN2.thy bearing the anti-thyroglobulin scFv provided with the Griffin.1 library. The $P_{tac}$ vector was a derivative of pIMS120 (Hayhurst, 2000).

E. Phage Panning

The Griffin.1 library is a semi-synthetic scFv library derived from a large repertoire of human heavy and light chains with part or all of the CDR3 loops randomly mutated and recombined in vivo (Griffiths et al., 1994). The library represents one potential source of candidate binding polypeptides for screening by anchored periplasmic expression in accordance with the invention. The library was rescued and subjected to five rounds of panning according to the web-site instruction manual (www.mrc-cpe.cam.ac.uk/~phage/glp.html), summarized in Example 9, below. Immunotubes were coated with 10 μgml$^{-1}$ digoxin-BSA conjugate and the neutralized eluates were halved and used to infect either TG-1 for the next round of phage panning, or ABLE™ C for FACS analysis.

Eluate titers were monitored to indicate enrichment of antigen binding phage. To confirm reactivity, a polyclonal phage ELISA of purified, titer normalized phage stocks arising from each round was performed on digoxin-ovalbumin conjugate. The percentage of positive clones arising in rounds 3, 4 and 5 was established by monoclonal phage ELISA of 96 isolates after each round. A positive was arbitrarily defined as an absorbance greater than 0.5 with a background signal rarely above 0.01. MvaI fingerprinting was applied to 24 positive clones from rounds 3, 4 and 5.

F. FACS Screening

For scanning with APEx expression, glycerol stocks of *E. coli* carrying the APEx construct were grown and labeled as described in section B and C. Following labeling cells were washed once in PBS and scanned. In the aforementioned studies using bodipy or FL labeled antigen, a 488 nm laser for excitation was used, while with Cy5 a 633 nm laser was used. Scanning was accomplished on a FACSCalibur (BD) using the following instrument settings: Sidescatter trigger V 400, Threshold 250, Forward scatter E01, FL1 V 400 FL2 V 400 (488 nm ex), FL4 V 700 (633 nm ex).

Sorting with APEx expression was as follows: all sorts were performed using a MoFlo FC (Cytomation). Previously described libraries were grown and labeled as described in section B and C, washed once with PBS and sorted for increased FL intensity. Subsequent rounds of sorting were applied until polyclonal scans of the population demonstrate enrichment. (See FIG. 4) Individual clones were then picked and analyzed for FL activity.

For other studies, an aliquot of phagemid containing, ABLE™C glycerol stock was scraped into 1 ml of 2×TY (2% glucose, 100 μgml$^{-1}$ ampicillin) to give an OD at 600 nm of approximately 0.1 cm$^{-1}$. After shaking vigorously at 37° C. for 2 h, IPTG was added to 1 mM and the culture shaken at 25° C. for 4 h. 50 μl of culture was labeled with 100 nM BODIPY™-digoxigenin (Daugherty et al., 1999) in 1 ml of 5×PBS for 1 h at room temperature with moderate agitation. For the last 10 min of labeling, propidium iodide was added to 2 μg/ml$^{-1}$. Cells were pelleted and resuspended in 100 μl of labeling mix. Scanning was performed with Becton-Dickinson FACSort, collecting 10$^4$ events at 1500 s$^{-1}$.

For FACS library sorting, the cells were grown in terrific broth and induced with 0.1 mMIPTG. Sorting was performed on 10$^6$ events (10$^7$ for round 2) in exclusion mode at 1000 s$^{-1}$. Collected sort liquor was passed through 0.7 μm membrane filters and colonies allowed to grow after placing the filter on top of SOC agar plus appropriate antibiotics at 30° C. for 24 h.

E. Analysis of Phage Clones

Screening phage particles by ELISA is summarized as follows. Binding of phage in ELISA is detected by primary sheep anti-M13 antisera (CP laboratories or 5 prime-3 prime) followed by a horseradish peroxidase (HRP) conjugated anti-sheep antibody (Sigma). Alternatively, a HRP-anti-M13 conjugate can be used (Pharmacia). Plates can be blocked with 2% MPBS or 3% BSA-PBS. For the polyclonal phage ELISA, the technique is generally as follows: coat MicroTest III flexible assay plates (Falcon) with 100 µl per well of protein antigen. Antigen is normally coated overnight at 4° C. at a concentration of 10–100 µg/ml in either PBS or 50 mM sodium hydrogen carbonate, pH 9.6. Rinse wells 3 times with PBS, by flipping over the ELISA plates to discard excess liquid, and fill well with 2% MPBS or 3% BSA-PBS for 2 hr at 37° C. Rinse wells 3 times with PBS. Add 10 µl PEG precipitated phage from the stored aliquot of phage from the end of each round of selection (about $10^{10}$ tfu.). Make up to 100 µl with 2% MPBS or 3% BSA-PBS. Incubate for 90 min at rt. Discard the test solution and wash three times with PBS-0.05% Tween 20, then 3 times with PBS. Add appropriate dilution of HRP-anti-M13 or sheep anti-M13 antisera in 2% MPBS or 3% BSA-PBS. Incubate for 90 min at rt, and wash three times with PBS-0.05% Tween 20, then 3 times with PBS. If sheep anti-M13 antisera is used, incubate for 90 min at rt, with a suitable dilution of HRP-anti-sheep antisera in 2% MPBS or 3% BSA and wash three times with PBS-0.05% Tween 20, then 3 times with PBS. Develop with substrate solution (100 µg/ml TMB in 100 mM sodium acetate, pH 6.0, add 10 µl of 30% hydrogen peroxide per 50 ml of this solution directly before use). Add 100 µl to each well and leave at rt for 10 min. A blue color should develop. Stop the reaction by adding 50 µl 1 M sulfuric acid. The color should turn yellow. Read the OD at 450 nm and at 405 nm. Subtract OD 405 from OD 450.

Monoclonal phage ELISA can be summarized as follows. To identify monoclonal phage antibodies the pHEN phage particles need to be rescued: Inoculate individual colonies from the plates in C10 (after each round of selection) into 100 µl 2×TY containing 100 µg/ml ampicillin and 1% glucose in 96-well plates (Corning 'Cell Wells') and grow with shaking (300 rpm.) overnight at 30° C. Use a 96-well transfer device to transfer a small inoculum (about 2 µl) from this plate to a second 96-well plate containing 200 µl of 2×TY containing 100 µg/ml ampicillin and 1% glucose per well. Grow shaking at 37° C. for 1 hr. Make glycerol stocks of the original 96-well plate, by adding glycerol to a final concentration of 15%, and then storing the plates at −70° C. To each well (of the second plate) add VCS-M13 or M13KO7 helper phage to an moi of 10. Stand for 30 min at 37° C. Centrifuge at 1,800 g. for 10 min, then aspirate off the supernatant. Resuspend pellet in 200 µl 2×TY containing 100 µg/ml ampicillin and 50 µg/ml kanamycin. Grow shaking overnight at 30° C. Spin at 1,800 g for 10 min and use 100 µl of the supernatant in phage ELISA as detailed above.

Production of antibody fragments is summarized as follows: the selected pHEN needs to be infected into HB2151 and then induced to give soluble expression of antibody fragments for ELISA. From each selection take 10 µl of eluted phage (about $10^5$ t.u.) and infect 200 µl exponentially growing HB2151 bacteria for 30 min at 37° C. (waterbath). Plate 1, 10, 100 µl, and 1:10 dilution on TYE containing 100 µg/ml ampicillin and 1% glucose. Incubate these plates overnight at 37° C. Pick individual colonies into 100 µl 2×TY containing 100 µg/ml ampicillin and 1% glucose in 96-well plates (Corning 'Cell Wells'), and grow with shaking (300 rpm.) overnight at 37° C. A glycerol stock can be made of this plate, once it has been used to inoculate another plate, by adding glycerol to a final concentration of 15% and storing at −70° C. Use a 96-well transfer device to transfer a small inocula (about 2 µl) from this plate to a second 96-well plate containing 200 µl fresh 2×TY containing 100 µg/ml ampicillin and 0.1% glucose per well. Grow at 37° C., shaking until the OD at 600 nm is approximately 0.9 (about 3 hr). Once the required OD is reached add 25 µl 2×TY containing 100 µg/ml ampicillin and 9 mM IPTG (final concentration 1 mM IPTG). Continue shaking at 30° C. for a further 16 to 24 hr. Coat MicroTest III flexible assay plates (Falcon) with 100 µl per well of protein antigen.

Antigen is normally coated overnight at rt at a concentration of 10–100 µg/ml in either PBS or 50 mM sodium hydrogen carbonate, pH 9.6. The next day rinse wells 3 times with PBS, by flipping over the ELISA plates to discard excess liquid, and block with 200 µl per well of 3% BSA-PBS for 2 hr at 37° C. Spin the bacterial plate at 1,800 g for 10 min and add 100 µl of the supernatant (containing the soluble scFv) to the ELISA plate for 1 hr at rt. Discard the test solution and wash three times with PBS. Add 50 µl purified 9E10 antibody (which detects myc-tagged antibody fragments) at a concentration of 4 µg/ml in 1% BSA-PBS and 50 µl of a 1:500 dilution of HRP-anti-mouse antibody in 1% BSA-PBS. Incubate for 60 min at rt, and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue color should develop. Stop the reaction by adding 50 µl 1 M sulphuric acid. The color should turn yellow. Read the OD at 450 nm and at 405 nm. Subtract OD 405 from OD 450.

Inserts in the library can be screened by PCR screening using the primers designated LMB3: CAG GAA ACA GCT ATG AC (SEQ ID NO:1) and Fd seq1: GAA TTT TCT GTA TGA GG (SEQ ID NO:2). For sequencing of the VH and VL, use is recommend of the primers FOR_LinkSeq: GCC ACC TCC GCC TGA ACC (SEQ ID NO:3) and pHEN-SEQ: CTA TGC GGC CCC ATT CA (SEQ ID NO:4).

Example 6

Antibody Affinity Maturation

Short et. al., (1995) isolated a 26-10 mutant, designated A4-19, having an equilibrium dissociation constant ($K_D$) for digoxin of 300 pM as measured by surface plasmon resonance. A4-19 contains 3 amino acid substitutions in heavy chain CDR1 ($V_H$:T30->P, $V_H$:D31->S and $V_H$:M34->Y). It was examined whether mutants with increased binding affinity can be obtained by soluble periplasmic expression/FACS screening even when starting with an antibody that already exhibits very tight binding. Three light chain CDR3 residues that make contact ($V_L$:T91, $V_L$:P96) or are in close proximity to ($V_L$:V94) the digoxin hapten (Jeffrey et al., 1993) were randomized using an NNS (S=G or C) strategy (Daugherty et al. 1998). A library of $2.5 \times 10^6$ transformants expressed in the periplasm via the pelB leader was generated and screened using two rounds of FACS. In the first round of screening, cells labeled with 100 nM of the fluorescent probe were washed once with PBS and sorted using recovery mode in which the instrument collects all fluorescent events even if a non-fluorescent particle is detected in the same element of fluid as a fluorescent particle. Operation in recovery mode provided a better assurance that very rare cells would be collected but at the expense of purity.

Collected cells were re-grown, labeled, washed and then incubated with a 50-fold excess (50 µM) of free digoxin for various times (15 min to 90 min). Cells that retained the desired level of fluorescence were isolated by sorting using exclusion mode, in which, coincident fluorescent and non-fluorescent events were rejected and thus a higher degree of purity was obtained. The rate of fluorescence decay for the pool of cells obtained following incubation with non-fluorescent competitor for various times was measured. A slightly faster rate compared to the starting A4-19 antibody was observed for the earlier time points (<60 minutes incubation with competitor) but the rate was reduced for the 60 min and 90 min populations. 5 random clones from the cell population obtained after 60 min of competition and 13 clones from the 90 min pool were picked at random and sequenced (Table 1). A strong sequence consensus was clearly evident. The hapten binding kinetics of the purified antibodies were determined by SPR and the results are shown in Table 1. The corresponding amino acid sequences are given by SEQ ID NOs:8–19. It should be noted that upon purification and analysis by gel filtration FPLC none of the mutants was found to dimerize. All of the mutants examined displayed association rate constants ($k_{on}$) indistinguishable from that of the starting A4-19 antibody ($0.9\pm0.2\times10^6$ M$^{-1}$). The $k_{diss}$ of the clones isolated after 60 min of competition were the same or faster than that of A4-19. Clones isolated after 90 minutes of competition exhibited slower $k_{diss}$ in solution. One clone, 90.3, exhibited a 2-fold slower dissociation rate constant resulting in a $K_D$ of 150 pM. Thus, the library screening methodology of the invention allowed specific labeling to isolate a better mutant, even when starting with an antibody that already exhibited a sub-nanomolar $K_D$. Interestingly, but not surprisingly, the effect of the three heavy chain CDR1 mutations present in 4-19 and the two mutations in residues 94 and 96 of the light chain were additive.

TABLE 1

Heavy and light chain CDR3 amino acid sequences (SEQ ID NOs:8–20) of mutants isolated by 60 min (clones 60.1–60.4 and 90 minutes (clones 90.1–90.6) off-rate selection. Number of identical clones shown in parenthesis. ND: Not Determined.

| | Light Chain Sequence 90 ... 96 | Off-rate/s |
|---|---|---|
| Wild Type 26-10 scFv | QTTHVPP | $8.4 \times 10^{-4}$ |
| A14-9 | QTTHVPP | $2.7 \times 10^{-4}$ |
| 60.1 (1 clone) | QTTHSPA | $5.5 \times 10^{-4}$ |
| 60.2 (2) | QTTHLPT | $2.8 \times 10^{-4}$ |
| 60.3 (1) | QTTHTPP | ND |
| 60.4 (1) | QTTHLPA | ND |
| 90.1 (1) | QTTHIPT | $3.2 \times 10^{-4}$ |
| 90.2 (1) | QTTHVPP | $2.7 \times 10^{-4}$ |
| 90.3 (7) | QTTHVPA | $2.2 \times 10^{-4}$ |
| 90.4 (1) | QTTHIPA | $1.4 \times 10^{-4}$ |
| 90.5 (3) | QTTHLPA | ND |
| 90.6 (1) | QTTHVPC | ND |

Example 7

Maximizing the Fluorescence Signal

The fluorescence intensity of cells expressing scFv antibodies in soluble form in the periplasm was strongly dependent on the E. coli strain used and on the growth conditions. With the 26-10 antibody, the maximum fluorescence intensity was obtained when the cells were grown at 25° C. Growth at sub-physiological temperature has several beneficial effects. Expression of scFv at low temperature (i.e., 25° C.) facilitates the proper folding of the scFv both directly, by slowing the folding pathway and indirectly by decreasing plasmid copy number to reduce expression load. Indeed, direct expression of scFv at 37° C. generally yields little or no soluble protein (for example see Gough et al., 1999). Outer membrane composition is also altered at non-physiological temperatures resulting in increased permeability (Martinez et al., 1999). Rather dramatic differences among various E. coli strains were noticed. Among several strains tested, the highest fluorescence intensities were obtained in ABLE™C. A preliminary analysis of protein expression and outer membrane protein profile in this strain indicated that the higher fluorescent signal was not due to the pcnB mutation which reduces the copy number of ColE1 origin plasmids but rather, due to differences in cell envelope protein composition. In fact, the stronger staining of ABLE™C was not related to a higher level of protein expression relative to other strains as deduced by ELISA and Western blotting.

Fluorescent labeling under hyperosmotic conditions, resulted in significantly greater fluorescence. A 5–7 fold increase in fluorescence was obtained when the cells were incubated in 5×PBS during labeling (a mean FL1>150 compared to 20–30 for cells incubated in regular PBS). However, the increased signal came at a cost, as cell viability decreased considerably. Such a decrease in viability may be undesirable when screening highly diverse libraries of proteins, whose expression may already have a deleterious effect on the host cell. Similarly, co-infection with filamentous phages such as M13KO7 induces the phage shock response, which among other things, results in an increase in outer membrane permeability. M13K07 infection resulted in a 3-fold increase in the mean fluorescence of the population. However, as with hyperosmotic shock the viability of the culture, as determined by propidium iodide staining was somewhat decreased.

Labeling of the cells with fluorescent ligand followed by incubation with a large excess of free ligand results in a time-dependent decrease in the mean fluorescence intensity. The rate of the fluorescence decay reflects the dissociation rate of the antibody-antigen complex (Daugherty et al., 2000). For digoxin the rate of fluorescence decay was found to be about 3–4 times slower compared to the dissociation rate measured with the purified antibody using BIACORE. The lower rate of fluorescence decay compared to the dissociation rate of the antibody/antigen complex in vitro stems from several effects including the collision frequency between ligands and cells, the concentration of antibody in the periplasm and, of course, the rate of diffusion through the outer membrane (see Martinez et al., (1996) for an analysis of kinetics in the periplasmic space). As may be expected, the ratio of the rate of fluorescence decay in the periplasm relative to the in vitro determined $k_{off}$ rate is antigen dependent.

Example 8

Fluorescence Detection and Enrichment of Cells Expressing scFv Antibodies in Soluble Form in the Periplasm The 26-10 scFv antibody binds with high affinity to cardiac glycosides such as digoxin and digoxigenin ($K_D$ of the purified antibodies for digoxin and digoxigenin are $0.9\pm0.2\times10^{-9}$ M$^{-1}$ and $2.4\pm0.4\times10^{-9}$ M$^{-1}$, respectively, Chen et al., 1999). The 26-10 scFv and its variants have been used extensively as a model system to understand the effect of mutations in the CDRs and in the framework regions on hapten binding (Schilbach et al., 1992; Short et al., 1995; Daugherty et al., 1998, 2000; Chen et al., 1999). A derivative of the 26-10 scFv was expressed in soluble form under the E. coli arabinose promoter and with the pelB leader peptide that allows secretion in the E. coli periplasm. The resulting plasmid vector (pBAD30pelB-Dig) was transformed in the ara⁻ E. coli strain LMG194 and protein synthesis was induced with 0.2% w/v arabinose. It was observed that upon incubation with 200 nM of digoxigenin-BODIPY™, cells that had been grown at 25° C. became strongly fluorescent and the fluorescence signal was retained even after extensive washing to remove non-specifically bound ligand. The labeling of the cells with a probe having a M.W. which is significantly higher than the generally accepted size limit of about 600 Da for the permeation of hydrophilic solutes in the periplasm (Decad and Nikaido, 1976) raised the possibility that the fluorescence signal was mainly due to non-viable, permeabilized cells. However, staining with the viability stain propidium iodide, which binds specifically to membrane damaged cells by virtue of intercalating with the normally inaccessible nucleic acids, revealed that >90% of the cells were not permeable to the dye. This is similar to the proportion of intact cells in control E. coli cultures harvested in late exponential phase.

Cells expressing the 26-10 antibody in the periplasm in soluble form could be enriched from a large excess of E. coli transformed with vector alone in a single round of sorting. Specifically, LMG194 (pBAD30pelB-Dig) were mixed with a 10,000 fold excess of E. coli containing empty vector (pBAD30). The former cells are resistant to both ampicillin and chloramphenicol (amp$^r$, Cm$^r$) whereas the latter are resistant to ampicillin only (amp$^r$). 4 hours after induction with 0.2% w/v arabinose, the cells were then labeled with 100 nM digoxigenin-BODIPY™ for 1 hour and fluorescent cells were isolated by FACS. Following re-growth of the sorted cells and re-labeling as above, the population exhibited a five to eight-fold increase in the mean fluorescence intensity (FL1=20 vs FL1=4 for the pre-sort cell mixture). The fraction of scFv-expressing clones in the enriched population was estimated from the number of amp$^r$ clones that were also Cm$^r$. 80% of the amp$^r$ colonies were also Cm$^r$ indicating that fluorescence labeling and cell sorting gave an enrichment of well over 1,000-fold in a single round Example 9

Increased Cell Permeability at Sub-Optimum Temperature

The fluorescence intensity of cells expressing scFv antibodies in soluble form in the periplasm was strongly dependent on the E. coli strain used and on the growth conditions. With the 26-10 antibody, the maximum fluorescence intensity was obtained when the cells were grown at 25° C. Growth at sub-physiological temperature has several beneficial effects. Expression of scFv at low temperature (i.e., 25° C.) facilitates the proper folding of the scFv both directly, by slowing the folding pathway and indirectly by decreasing plasmid copy number to reduce expression load. Indeed, direct expression of scFv at 37° C. generally yields little or no soluble protein (for example see Gough et al., 1999). Outer membrane composition is also altered at non-physiological temperatures resulting in increased permeability (Martinez et al., 1999). Rather dramatic differences among various E. coli strains were noticed. Among several strains tested, the highest fluorescence intensities were obtained in ABLE™C. A preliminary analysis of protein expression and outer membrane protein profile in this strain indicated that the higher fluorescent signal was not due to the pcnB mutation which reduces the copy number of ColE1 origin plasmids but rather, due to differences in cell envelope protein composition. In fact, the stronger staining of ABLE™C was not related to a higher level of protein expression relative to other strains as deduced by ELISA and Western blotting.

Fluorescent labeling under hyperosmotic conditions, resulted in significantly greater fluorescence. A 5–7 fold increase in fluorescence was obtained when the cells were incubated in 5×PBS during labeling (a mean FL1>150 compared to 20–30 for cells incubated in regular PBS). However, the increased signal came at a cost, as cell viability decreased considerably. Such a decrease in viability may be undesirable when screening highly diverse libraries of proteins, whose expression may already have a deleterious effect on the host cell. Similarly, co-infection with filamentous phages such as M13KO7 induces the phage shock response, which among other things, results in an increase in outer membrane permeability. M13 K07 infection resulted in a 3-fold increase in the mean fluorescence of the population. However, as with hyperosmotic shock the viability of the culture, as determined by propidium iodide staining was somewhat decreased.

Labeling of the cells with fluorescent ligand followed by incubation with a large excess of free ligand results in a time-dependent decrease in the mean fluorescence intensity. The rate of the fluorescence decay reflects the dissociation rate of the antibody-antigen complex (Daugherty et al., 2000). For digoxin, the rate of fluorescence decay was found to be about 3–4 times slower compared to the dissociation rate measured with the purified antibody using BIACORE. The lower rate of fluorescence decay compared to the dissociation rate of the antibody/antigen complex in vitro stems from several effects including the collision frequency between ligands and cells, the concentration of antibody in the periplasm and, of course, the rate of diffusion through the outer membrane (see Martinez et al., 1996) for an analysis of kinetics in the periplasmic space). As may be expected, the ratio of the rate of fluorescence decay in the periplasm relative to the in vitro determined $k_{off}$ rate is antigen dependent.

Example 10

Analysis and Screening of Repertoire Antibody Libraries by FACS

Antibodies can be isolated de novo, i.e., without animal immunization, by screening large, repertoire libraries that contain a wide variety of antibody sequences. The screening of such large libraries is well established (Nissim et al. 1994, Winter et al. 1994, Griffith et al. 1994, Knappik et al. 2000). So far, all the large antibody repertoire libraries available have been constructed for use with phage display. However, libraries constructed for phage display can also be used for the expression of proteins within the bacterial periplasmic space, either anchored to the inner membrane or in soluble form. In particular, for low protein copy number display on filamentous bacteriophage, recombinant polypeptides are expressed as N-terminal fusions to pIII. During the course of phage biogenesis, pIII fusions are first targeted to the periplasm and anchored in the inner membrane by a small C-terminal portion of pIII. As phage are released, the scFv-pIII fusion is incorporated alongside wild-type pIII at the terminus of the phage, thereby concluding the assembly process (Rakonjac and Model, 1998; Rakonjac et al., 1999). In the most widely used vectors for phage display, an amber codon is placed between the N-terminal scFv and the pIII gene. Thus, in a suitable *E. coli* suppressor strain, full-length scFv-pIII fusion protein is produced for displaying the scFv whereas in a non-supressor strain only soluble scFv is expressed. Alternatively, by including an inner membrane anchor peptide in the fusion, anchored expression can be achieved.

The degree of suppression with phage display varies with vector and strain but tends to allow only 10% read-through. Thus, as a consequence of the biology of phage display, all amber-codon containing libraries result in a degree of periplasmic expression regardless of host. Hence, it was of great interest to explore whether FACS can aid the isolation of ligand binding proteins from pre-existing, highly diverse, naive libraries (Griffiths et al., 1994; Vaughan et al., 1996; Sheets et al., 1998; Pini et al., 1998; de Haard et al., 1999; Knappik et al., 2000; Sblattero and Bradbury, 2000).

Conventional screening was performed of a phage library by phage panning enriched phage expressing scFvs specific for the cardiac glycoside digoxin from a naïve antibody repertoire library. The panning process was performed on a BSA conjugate and the screening was performed on an ovalbumin conjugate to reduce the incidence of protein and hapten-protein interface binders. 24 positive isolates from pan 4 shared the same fingerprint and DNA sequencing of 6 clones confirmed the same heavy and light chain sequence ("dig1") with one of six ("dig2") having a unique HCDR3 and LCDR3 combination. Repeated screening of the phage library both under identical and under different conditions resulted only in the isolation of clones with the same DNA fingerprint.

FACS analysis of the phage rescued in *E. coli* ABLE™C after each round of panning reveals an increase in mean fluorescence at round 3 which mirrors the phage ELISA signals. Significant enrichment of binding clones using a single round of FACS was obtained starting with the population obtained from the $3^{rd}$ round of phage panning. This result is consistent with the enrichment profiles obtained during the course of the panning experiment. FACS screening and sorting $10^6$ cells from rounds 3, 4 and 5 resulted in the isolation of positive clones at a frequency of 30, 80 and 100% respectively.

Out of 14 clones isolated by FACS from the round 3 population, 5 were found to be positive for binding to digoxin. Importantly, three of the clones corresponded to a different antibody that was missed by phage panning (herein known as "dig3"). The remaining 2 were the dig1 clone. This result demonstrates that FACS screening of libraries expressed in the periplasmic space and labeled with fluorescent ligands results in the isolation of clones that cannot be isolated by other library screening methodologies.

Example 11

Summary of Methodology for Use of the Griffin.1 Library

Methodology for using the Griffin.1 library can be summarized as follows. The Griffin.1 library is a scFv phagemid library made from synthetic V-gene segments. The library was made by recloning the heavy and light chain variable regions from the lox library vectors (Griffiths et al., 1994) into the phagemid vector pHEN2. A kit for use of the library will contain a tube of the synthetic scFv Library (1 ml), a glycerol stock of the positive control (TG1 containing an anti-thyroglobulin clone), a glycerol stock of the negative control (TG1 containing pHEN2), a glycerol stock of *E. coli* TG1 (Gibson, 1984) suppressor strain (K12, del(lac-pro), supE, thi, hsdD5/F'traD36, proA+B+, lacIq, lacZdelM15) for propagation of phage particles (the strain supplied is a T-phage resistant variant of this), a glycerol stock of *E. coli* HB2151 (Carter et al., 1985) and non-suppressor strain (K12, ara, del(lac-pro), thi/F'proA+B+, lacIq, lacZdelM15) for expression of antibody fragments. The library is kept frozen at −70° C. until needed.

The strains are plated and then are grown up as overnight cultures (shaking at 37° C.) of each in 2×TY containing 100 μg/ml ampicillin and 1% glucose. Cultures are diluted 1:100 with 2×TY (2×TY is 16 g Typtone, 10 g Yeast Extract and 5 g NaCl in 1 liter) containing 100 μg/ml ampicillin and 1% glucose and the phagemids rescued by following the procedures described below. A 1:100 mixture is used of positive and the negative control together for one round of selection on immunotubes, coated with thyroglobulin.

The protocol for use of the library is summarized as follows. Phage/phagemid infect F+-*E. coli* via the sex pili. For sex pili production and efficient infection *E. coli* must be grown at 37° C. and be in log phase (OD at 600 nm of 0.4–0.6). Throughout the following protocol such a culture is needed. It can be prepared as follows: transfer a bacterial colony from a minimal media plate into 5 ml of 2×TY medium and grow shaking overnight at 37° C. Next day, subculture by diluting 1:100 into fresh 2×TY medium, grow shaking at 37° C. until OD 0.4–0.6 and then infect with phage. A variety of helper phages are available for the rescue of phagemid libraries. VCS-M13 (Stratagene) and M13KO7 (Pharmacia) can be purchased in small aliquots, larger quantities for rescue of phagemid libraries can be prepared as follows: Infect 200 μl *E. coli* TG1 (or other suitable strain) at OD 0.2 with 10 μl serial dilutions of helper phage (in order to get well separated plaques) at 37° C. (waterbath) without shaking for 30 min. Add to 3 ml molten H-top agar (42° C.) and pour onto warn TYE (note 7) plates. Allow to set and then incubate overnight at 37° C. Pick a small plaque into 3–4 ml of an exponentially growing culture of TG1 (see above). Grow for about 2 hr shaking at 37° C. Inoculate into 500 ml 2×TY in a 2 liter flask and grow as before for 1 hr and then add kanamycin (25 μg/ml in water) to a final concentration of 50–70 μg/ml. Grow for a further 8–16 hr. Spin down bacteria at 10,800 g for 15 min. To the phage supernatant add ⅕ volume PEG/NaCl (20% polyethylene glycol 6000–2.5 M NaCl) and incubate for a minimum of 30 min on ice. Spin 10,800 g for 15 min. Resuspend pellet in 2 ml TE and filter sterilize the stock through a 0.45 μn filter (Minisart NML; Sartorius). Titre the stock and then dilute to about 1×1012 p.f.u./ml. Store aliquots at −20° C. All spins are performed at 4° C., unless otherwise stated.

For growth of the library, the procedure is summarized as follows: inoculate the whole of the bacterial library stock (about $1×10^{10}$ clones) into 500 ml 2×TY containing 100 μg/ml ampicillin and 1% glucose. Grow with shaking at 37° C. until the OD at 600 nm is 0.5, this should take about 1.5–2 hours. Infect 25 ml ($1×10^{10}$ bacteria) from this culture with VCS-M13 or M13KO7 helper phage by adding helper phage in the ratio of 1:20 (number of bacterial cells:helper phage particles, taking into account that 1 OD bacteria at 600 nm=around 8×108 bacteria/ml).

Spin the infected cells at 3,300 g for 10 min. Resuspend the pellet gently in 30 ml of 2×TY containing 100 μg/ml ampicillin and 25 μg/ml kanamycin. Add 470 ml of pre-warmed 2×TY containing 100 μg/ml ampicillin and 25

µg/ml kanamycin and incubate shaking at 30° C. overnight. The phage can be concentrated and any soluble antibodies removed (as in TG1 suppression of the amber stop codon encoded at the junction of the antibody gene and gIII is never complete) by precipitating with Polyethylene glycol (PEG) 6000. Spin the culture from A6 at 10,800 g for 10 min (or 3,300 g for 30 min). Add ⅕ volume PEG/NaCl (20% Polyethylene glycol 6000, 2.5 M NaCl) to the supernatant. Mix well and leave for 1 hr or more at 4° C. Spin 10,800 g for 30 min. Resuspend the pellet in 40 ml water and add 8 ml PEG/NaCl. Mix and leave for 20 min or more at 4° C. Spin at 10,800 g for 10 min or 3,300 g for 30 min and then aspirate off the supernatant. Respin briefly and then aspirate off any remaining PEG/NaCl. Resuspend the pellet in 5 ml PBS and spin 11,600 g for 10 min in a microcentrifuge to remove most of the remaining bacterial debris. Store the phage supernatant at 4° C. for short term storage or in PBS, 15% glycerol for longer term storage at −70° C. To titre the phage stock dilute 1 µl phage in 1 ml PBS and use 1 µl of this to infect 1 ml of TG1 at an OD600 0.4–0.6. Plate 50 µl of this, 50 µl of a 1:10² dilution and 50 µl of a 1:10⁴ on TYE plates containing 100 µg/ml ampicillin and 1% glucose and grow overnight at 37° C. Phage stock should be $10^{12}$–$10^{13}$/ml.

Selection on immunotubes is summarized as follows. Coat Nunc-immunotube (Maxisorp Cat. No. 4-44202) overnight with 4 ml of the required antigen. The efficiency of coating can depend on the antigen concentration, the buffer and the temperature. Usually 10–100 µg/ml antigen in PBS or 50 mM sodium hydrogen carbonate, pH 9.6 at room temperature (rt), is used. Next day wash tube 3 times with PBS (simply pour PBS into the tube and then pour it immediately out again). Fill tube to brim with 2% MPBS. Cover and incubate at 37° C. (or rt according to the stability of antigen) for 2 hr to block. Wash tube 3 times with PBS. Add $10^{12}$ to $10^{13}$ cfu. phage, from A13, in 4 ml of 2% MPBS. Incubate for 30 min at rt rotating continuously on an under-and-over turntable and then stand for at least a further 90 min at rt. Throw away the unbound phage in the supernatant. For the first round of selection wash tubes 10 times with PBS containing 0.1% Tween-20, then 10 times with PBS to remove the detergent. Each washing step is performed by pouring buffer in and immediately out. For the second and subsequent rounds of selection wash tubes 20 times with PBS containing 0.1% Tween-20, then 20 times with PBS. Shake out the excess PBS from the tube and elute phage by adding 1 ml 100 mM triethylamine (700 µl triethylamine (7.18 M) in 50 ml water, diluted on day of use) and rotating continuously for 10 min on an under-and-over turntable. During the incubation, tubes are prepared with 0.5 ml 1M Tris, pH 7.4 ready to add the eluted 1 ml phage, from 7, for quick neutralization. Phage can be stored at 4° C. or used to infect TG1 as described above. After elution add another 200 µl of 1M Tris, pH 7.4 to the immunotube to neutralize the remaining phage in the tube. Take 9.25 ml of an exponentially growing culture of TG1 and add 0.75 ml of the eluted phage. Also add 4 ml of the TG1 culture to the immunotube. Incubate both cultures for 30 min at 37° C. (waterbath) without shaking to allow for infection. Pool the 10 ml and 4 ml of the infected TG1 bacteria and take 100 µl to make 4–5 100-fold serial dilutions. Plate these dilutions on TYE containing 100 µg/ml ampicillin and 1% glucose. Grow overnight at 37° C. Take the remaining infected TG1 culture and spin at 3,300 g for 10 min. Resuspend the pelleted bacteria in 1 ml of 2×TY and plate on a large Nunc Bio-Assay dish (Gibco-BRL (note 8)) of TYE containing 100 µg/ml ampicillin and 1% glucose. Grow at 30° C. overnight, or until colonies are visible.

For further rounds of selection, add 5–6 ml of 2×TY, 15% glycerol to the Bio-Assay dish of cells and loosen the cells with a glass spreader. After inoculating 50–100 µl of the scraped bacteria to 100 ml of 2×TY containing 100 µg/ml ampicillin and 1% glucose, store the remaining bacteria at −70° C. Once again it is a good idea to check starting OD at 600 nm is =<0.1. Grow the bacteria with shaking at 37° C. until the OD at 600 nm is 0.5 (about 2 hr). Infect 10 ml of this culture with VCS-M13 or M13KO7 helper phage by adding helper phage in the ratio of 1:20 (number of bacterial cells:helper phage particles, taking into account that 1 OD bacteria at 600 nm=around $8 \times 10^8$ bacteria/ml). Incubate without shaking in a 37° C. water bath for 30 min. Spin the infected cells at 3,300 g for 10 min. Resuspend the pellet gently in 50 ml of 2×TY containing 100 µg/ml ampicillin and 25 µg/ml kanamycin and incubate shaking at 30° C. overnight. Take 40 ml of the overnight culture and spin at 10,800 g for 10 min or 3,300 g for 30 min. Add ⅕ volume (8 ml) PEG/NaCl (20% Polyethylene glycol 6000, 2.5 M NaCl) to the supernatant. Mix well and leave for 1 hr or more at 4° C. Spin 10,800 g for 10 min or 3,300 g for 30 min and then aspirate off the supernatant. Respin briefly and then aspirate off any remaining dregs of PEG/NaCl. Resuspend the pellet in 2 ml PBS and spin 11, 600 g for 10 min in a micro centrifuge to remove most of the remaining bacterial debris. 1 ml of this phage can be stored at 4° C. and the other 1 ml aliquot can be used for the next round of selection. Repeat the selection for another 2–3 rounds.

Screening phage particles by ELISA is summarized as follows. Binding of phage in ELISA is detected by primary sheep anti-M13 antisera (CP laboratories or 5 prime-3 prime) followed by a horseradish peroxidase (HRP) conjugated anti-sheep antibody (Sigma). Alternatively, a HRP-anti-M13 conjugate can be used (Pharmacia). Plates can be blocked with 2% MPBS or 3% BSA-PBS. For the polyclonal phage ELISA, the technique is generally as follows: coat MicroTest III flexible assay plates (Falcon) with 100 µl per well of protein antigen. Antigen is normally coated overnight at rt at a concentration of 10–100 µg/ml in either PBS or 50 mM sodium hydrogen carbonate, pH 9.6. Rinse wells 3 times with PBS, by flipping over the ELISA plates to discard excess liquid, and block with 200 µl per well of 2% MPBS or 3% BSA-PBS for 2 hr at 37° C. Rinse wells 3 times with PBS. Add 10 µl PEG precipitated phage from the stored aliquot of phage from the end of each round of selection (about $10^{10}$ cfu.). Make up to 100 µl with 2% MPBS or 3% BSA-PBS. Incubate for 90 min at rt. Discard the test solution and wash three times with PBS-0.05% Tween 20, then 3 times with PBS. Add appropriate dilution of HRP-anti-M13 or sheep anti-M13 antisera in 2% MPBS or 3% BSA-PBS. Incubate for 90 min at rt, and wash three times with PBS-0.05% Tween 20, then 3 times with PBS. If sheep anti-M13 antisera is used, incubate for 90 min at rt, with a suitable dilution of HRP-anti-sheep antisera in 2% MPBS or 3% BSA and wash three times with PBS-0.05% Tween 20, then 3 times with PBS. Develop with substrate solution (100 µg/ml TMB in 100 mM sodium acetate, pH 6.0. Add 10 µl of 30% hydrogen peroxide per 50 ml of this solution directly before use). Add 100 µl to each well and leave at rt for 10 min. A blue color should develop. Stop the reaction by adding 50 µl 1 M sulphuric acid. The color should turn yellow. Read the OD at 450 nm and at 405 nm. Subtract OD 405 from OD 450.

Monoclonal phage ELISA can be summarized as follows. To identify monoclonal phage antibodies the pHEN phage particles need to be rescued: Inoculate individual colonies from the plates in C10 (after each round of selection) into 100 μl 2×TY containing 100 μg/ml ampicillin and 1% glucose in 96-well plates (Corning 'Cell Wells') and grow with shaking (300 rpm.) overnight at 37° C. Use a 96-well transfer device to transfer a small inoculum (about 2 μl) from this plate to a second 96-well plate containing 200 μl of 2×TY containing 100 μg/ml ampicillin and 1% glucose per well. Grow shaking at 37° C. for 1 hr. Make glycerol stocks of the original 96-well plate, by adding glycerol to a final concentration of 15%, and then storing the plates at −70° C. To each well (of the second plate) add 25 μl 2×TY containing 100 μg/ml ampicillin, 1% glucose and 109 pfu VCS-M13 or M13KO7 helper phage. Stand for 30 min at 37° C., then shake for 1 hr at 37° C. Spin 1,800 g. for 10 min, then aspirate off the supernatant. Resuspend pellet in 200 μl 2×TY containing 100 μg/ml ampicillin and 50 μg/ml kanamycin. Grow shaking overnight at 30° C. Spin at 1,800 g for 10 min and use 100 μl of the supernatant in phage ELISA as detailed above.

Production of soluble antibody fragments is summarized as follows: the selected pHEN needs to be infected into HB2151 and then induced to give soluble expression of antibody fragments for ELISA. From each selection take 10 μl of eluted phage (about 105 t.u.) and infect 200 μl exponentially growing HB2151 bacteria for 30 min at 37° C. (waterbath). Plate 1, 10, 100 μl, and 1:10 dilution on TYE containing 100 μg/ml ampicillin and 1% glucose. Incubate these plates overnight at 37° C. Pick individual colonies into 100 μl 2×TY containing 100 μg/ml ampicillin and 1% glucose in 96-well plates (Corning 'Cell Wells'), and grow with shaking (300 rpm.) overnight at 37° C. A glycerol stock can be made of this plate, once it has been used to inoculate another plate, by adding glycerol to a final concentration of 15% and storing at −70° C. Use a 96-well transfer device to transfer a small inocula (about 2 μl) from this plate to a second 96-well plate containing 200 μl fresh 2×TY containing 100 μg/ml ampicillin and 0.1% glucose per well. Grow at 37° C., shaking until the OD at 600 nm is approximately 0.9 (about 3 hr). Once the required OD is reached add 25 μl 2×TY containing 100 μg/ml ampicillin and 9 mM IPTG (final concentration 1 mM IPTG). Continue shaking at 30° C. for a further 16 to 24 hr. Coat MicroTest III flexible assay plates (Falcon) with 100 μl per well of protein antigen. Antigen is normally coated overnight at rt at a concentration of 10–100 μg/ml in either PBS or 50 mM sodium hydrogen carbonate, pH 9.6. The next day rinse wells 3 times with PBS, by flipping over the ELISA plates to discard excess liquid, and block with 200 μl per well of 3% BSA-PBS for 2 hr at 37° C. Spin the bacterial plate at 1,800 g for 10 min and add 100 μl of the supernatant (containing the soluble scFv) to the ELISA plate for 1 hr at rt. Discard the test solution and wash three times with PBS. Add 50 μl purified 9E10 antibody (which detects myc-tagged antibody fragments) at a concentration of 4 μg/ml in 1% BSA-PBS and 50 μl of a 1:500 dilution of HRP-anti-mouse antibody in 1% BSA-PBS. Incubate for 60 min at rt, and wash three times with PBS-0.05% Tween 20, then 3 times with PBS. Develop with substrate solution (100 μg/ml TMB in 100 mM sodium acetate, pH 6.0. Add 10 μl of 30% hydrogen peroxide per 50 ml of this solution directly before use). Add 100 μl to each well and leave at rt for 10 min. A blue color should develop. Stop the reaction by adding 50 μl 1 M sulphuric acid. The color should turn yellow. Read the OD at 450 nm and at 405 nm. Subtract OD 405 from OD 450.

Inserts in the library can be screened by PCR screening using the primers designated LMB3: CAG GAA ACA GCT ATG AC (SEQ ID NO:1) and Fd seq1: GAA TTT TCT GTA TGA GG (SEQ ID NO:2). For sequencing of the VH and VL, use is recommend of the primers FOR_LinkSeq: GCC ACC TCC GCC TGA ACC (SEQ ID NO:3) and pHEN-SEQ: CTA TGC GGC CCC ATT CA (SEQ ID NO:4).

Example 12

Isolation of scFV Antibodies Specific to TNB from a Repertoire Library

This example summarizes the screening of a repertoire antibody library to the ligand TNB (trinitrobenzene). Library screening was initiated by first carrying out three rounds of phage panning of a repertoire library (Griffin-1 library) using standard protocols (see Example 9, also described in www.mrc-cpe.cam.ac.uk/~phage/glp.html). Phage rescued from various rounds of panning were used to infect the *E. coli* ABLE C. The cells were grown to mid-exponential phase, induced for expression of scFv antibodies in soluble form as described above and labeled with 100 nM TNBS conjugated to the fluorescent dye Cy5. The labeled cells were analyzed by flow cytometry using a Cytomation MoFlo instrument equipped with a 5 mM diode laser emitting at 633 nm. Highly fluorescent clones were isolated on membrane filters and analyzed further. Three out of 10 clones isolated by FACS were analyzed further and found to exhibit strong binding to a TNBS-BSA conjugate. Sequence analysis confirmed that one of the TNBS specific clones had also been found by phage display. However, the two other clones isolated by soluble periplasmic expression of the library and FACS screening did not correspond to any of the clones isolated by phage panning.

Example 13

Detection of Oligonucleotide Probes by Antibodies Expressed in Soluble Form in the *E. coli* Periplasm This example shows that modified oligonucleotides can diffuse through the outer membrane of bacteria. An oligonucleotide with the sequence 5'-digoxigenin-AAAAA-fluoroscein-3' (designated dig-5A-FL, molecular weight of 2,384 Da, SEQ ID NO:5) containing four nuclease resistant phosphorothioate linkages between the five A residues was synthesized and purified (RP HPLC) by Integrated DNA Technologies, IA. The digoxigenin moiety of this oligonucleotide can be recognized by scFv antibodies specific to digoxin (anti-digoxin scFv). Cells expressing the anti-digoxin scFv in the periplasm may bind 5A-Fl which in turn should render the cells fluorescent, provided that the probe molecule can diffuse through the outer membrane.

ABLE™C cells expressing periplasmic scFv specific for either atrazine (Hayhurst 2000) as a negative control or digoxigenin were incubated in 5× strength PBS together with either 100 nM of digoxigenin-BODIPY™ or 100 nM of dig-5A-FL. Propidium iodine was also added to serve as a viability stain. Viable cells were gated on the basis of propidium iodine exclusion (to identify cells with an intact membrane) and side scatter. Approximately 10,000 cells were analyzed at a rate of 1,000 events per second. The resulting data are shown in FIG. 3. Cells expressing an unrelated anti-atrazine antibody that does not bind to the probe exhibited only background fluorescence. In contrast, cells displaying the anti-digoxin scFv antibody became clearly labeled with both the digoxigenin-BODIPY™ as well as with 5-A-FL. The latter probe gave a signal that was clearly higher than that observed with the control cells. Even though 5-A-FL gave a lower fluorescence intensity compared to the smaller and uncharged the digoxigenin-BODIPY, the signal obtained with the former probe was sufficient for the screening of scFv libraries by FACS.

Example 14

Flow Cytometric Discrimination of *E. coli* Expressing the *Fusarium solani* Lipase Cutinase Using Commercial Fluorescent Substrates This example demonstrates that commercially available fluorescent substrates can be used to specifically label *E. coli* cells displaying relevant enzymes in the periplasm. Surprisingly, the soluble fluorescent product of these reactions is sufficiently retained within the cell to allow for the discrimination and selection of enzyme expressing *E. coli* from non-enzyme expressing bacteria.

The gene encoding *Fusarium solani* lipase cutinase was constructed by total gene synthesis and placed downstream of the strong inducible promoter pBAD in plasmid pBAD18Cm. Protein expression from the pBAD promoter is beneficial for the screening of protein libraries by FACS (Daugherty et al. 1999). The resulting plasmid encoding the cutinase gene was designated pKG3-53-1. pKG3-53-1, and pBAD18Cm as a control, were both transformed into DH5a. In this example, the ability to discriminate cells expressing cutinase (DH5a(pKG3-53-1)) from control cells was determined using two different commercially available substrates: Fluorescein dibutyrate or LysoSensor Green DND-189 (LSG) (both from Molecular Probes, OR). The latter is a positively charged fluorescent probe that detects pH changes in the cell occurring due to ester hydrolysis by the enzyme.

Cells were grown overnight with vigorous shaking at 37° C. in terrific broth/chloramphenicol 50 μg/ml (TB/Cm). Subcultures were made from 100 μl of overnight culture in 10 ml of TB/Cm(50 μg/ml). These subcultures were grown with vigorous shaking at 37° C. to $OD_{600}$=0.6. Four ml aliquots of the subcultures were pelleted at 3650 rpm for 20 minutes in a Beckman Allegra 6R Centrifuge. The supernatant was removed, and the pellets were resuspended in 4 ml of M9 minimal media containing 0.2% glucose and chloramphenicol (Cm) at 50 μg/ml. Arabinose, from a 20% stock, was added to a final concentration of 0.2%. The cultures were induced at 25° C. with vigorous shaking for 4 hours. Subsequently, 2 ml aliquots of the induced cultures were pelleted at 800 rpm for 10 minutes in an Eppendorf 5415 C Centrifuge, washed with fresh media and pelleted again at 8000 rpm for 10 min. The washed pellets were resuspended in M9 salts media without glucose to an optical density $OD_{600}$=1.0. The stock solution was diluted 1:10 and 1 ml of the diluted cell suspension was mixed with 0.1 ml 0.1 mM Fluorescein dibutyrate (FDB) stock solution in dimethyl sulfoxide (DMSO). The final FDB concentration was 10 μM. Reactions were allowed to proceed at 37° C. for 30 minutes. The labeled cells were immediately analyzed on a Becton Dickinson FACSort equipped with an Ar 488 nm laser. The fluorescence distribution of the cutinase expressing cells and the control cells is shown in FIG. 9A.

The utility of a second probe for the discrimination between positive (enzyme expressing) and control cells was also examined. *E. coli* expressing cutinase from the pKG3-53-4 plasmid, and negative cells (expressing the unmodified pBAD18Cm plasmid) were grown, induced and washed as above. The pellet was washed with 1% sucrose, pelleted again, and resuspended in fresh 1% sucrose to $OD_{600}$=1.0. This stock solution of cells was kept on ice.

For labeling, a LysoSensor Green DND-189 (LSG, Molecular Probes) stock solution was prepared to 1 mM in DMSO. Also, a 1 M 4-Nitrophenyl Butyrate stock solution was prepared in DMSO. Cell labeling was initiated by first diluting the cell stock solution, adding the LSG to a final concentration of 1 μM and diluting the 4-Nitrophenyl Butyrate 1:1000 to give a final concentration of 1 μM. The enzymatic hydrolysis of 4-Nitrophenyl Butyrate by the cells was allowed to proceed at 25° C. for 5 minutes and the cells were then immediately analyzed on a Becton Dickinson FACSort as above. The fluorescence distribution of the cutinase expressing cells and the control cells stained with the LysoSensor Green DND-189 probe is shown in FIG. 9B.

Example 15

Use of Anchored Periplasmic Expression to Isolate Antibodies with Over a 120-Fold Improvement in Affinity for the *Bacillus anthracis* Protective Antigen The screening of large libraries requires a physical link between a gene, the protein it encodes, and the desired function. Such a link can be established using a variety of in vivo display technologies that have proven invaluable for mechanistic studies, for biotechnological purposes and for proteomics research (Hoess, 2001; Hayhurst and Georgiou, 2001; Wittrup, 2000).

APEx is an alternative approach that allows screening by flow cytometry (FC). FC combines high throughput with real-time, quantitative, multi-parameter analysis of each library member. With sorting rates on the order of more than 400 million cells per hour, commercial FC machines can be employed to screen libraries of the size accessible within the constraints of microbial transformation efficiencies. Furthermore, multi-parameter FC can provide valuable information regarding the function of each and every clone in the library in real time, thus helping to guide the library construction process and optimize sorting conditions (Boder and Wittrup, 2000; Daugherty et al., 2000).

Bacterial and yeast protein display in combination with FC has been employed for the engineering of high affinity antibodies to a variety of ligands (Daugherty et al., 1999; Boder et al., 2000). However, the requirement for the display of proteins on cell surfaces imposes a number of biological constraints that can impact library screening applications. Processes such as the unfolded protein response in eucaryotes or the stringency of protein sorting to the outer membrane of Gram-negative bacteria limit the diversity of the polypeptides that are actually compatible with surface display (Sagt et al., 2002; Sathopoulos et al., 1996). In addition, microbial surfaces are chemically complex structures whose macromolecular composition can interfere with protein:ligand recognition. This problem is particularly manifest in Gram-negative bacteria because the presence of lipopolysaccharides on the outer membrane presents a steric barrier to protein:ligand recognition, a fact that likely contributed to the evolution of specialized appendages, such as pili or fimbriae (Hultgren et al., 1996).

APEx overcomes the biological constraints and antigen access limitations of previous display strategies, enabling the efficient isolation of antibodies to virtually any size antigen. In APEx, proteins are tethered to the external (periplasmic) side of the *E. coli* cytoplasmic membrane as either N- or C-terminal fusions, thus eliminating biological constraints associated with the display of proteins on the cell surface. Following chemical/enzymatic permeabilization of the bacterial outer membrane, *E. coli* cells expressing anchored scFv antibodies can be specifically labeled with fluorescent antigens, of at least 240 kDa, and analyzed by FC. By using APEx the inventors have demonstrated the efficient isolation of antibodies with markedly improved ligand affinities, including an antibody fragment to the protective antigen of *Bacillus anthracis* with an affinity that was increased over 120-fold.

A. Anchored Periplasmic Expression and Detection of Ligand Binding

For screening applications, an ideal expression system should minimize cell toxicity or growth abnormalities that can arise from the synthesis of heterologous polypeptides (Daugherty et al., 2000). Use of APEx avoids the complications that are associated with transmembrane protein fusions (Miroux and Walker, 1996; Mingarro et al., 1997). Unlike membrane proteins, bacterial lipoproteins are not known to require the SRP or YidC pathways for membrane anchoring (Samuelson et al., 2000). Lipoproteins are secreted across the membrane via the Sec pathway and once in the periplasm, a diacylglyceride group is attached through a thioether bond to a cysteine residue on the C-terminal side of the signal sequence. The signal peptide is then cleaved by signal peptidase II, the protein is fatty acylated at the modified cysteine residue, and finally the lipophilic fatty acid inserts into the membrane, thereby anchoring the protein (Pugsley, 1993; Seydel et al., 1999; Yajushi et al., 2000).

A sequence encoding the leader peptide and first six amino acids of the mature NlpA (containing the putative fatty acylation and inner membrane targeting sites) was employed for anchoring scFv antibodies to the periplasmic face of the inner membrane. NlpA is a non-essential *E. coli* lipoprotein that exclusively localizes to the inner membrane (Yu et al., 1986; Yamaguchi et al., 1988). Of particular note is the aspartate residue adjacent to the fatty acylated cysteine residue that is thought to be a consensus residue for inner membrane targeting (Yamaguchi et al., 1988). NlpA fusions to the 26-10 anti-digoxin/digoxigenin (Dig) scFv and to the anti-*B. anthracis* protective antigen (PA) 14B7 scFv were constructed and expressed from a lac promoter in *E. coli*. Following induction of the NlpA-[scFv] synthesis using IPTG, the cells were incubated with EDTA and lysozyme to disrupt the outer membrane and the cell wall. The permeabilized cells were mixed with the respective antigens conjugated to the fluorescent dye BODIPY™ (200 nM) and the cell fluorescence was determined by flow cytometry. Treated cells expressing the NlpA-[14B7 scFv] and the NlpA-[Dig scFv] exhibited an approximate 9-fold and 16-fold higher mean fluorescence intensity, respectively, compared to controls (FIG. 7A). Only background fluorescence was detected when the cells were mixed with unrelated fluorescent antigen, indicating negligible background binding under the conditions of the study.

To further evaluate the ability of antibody fragments anchored on the cytoplasmic membrane to bind bulky antigens, the inventors examined the ability of the NlpA-[Dig scFv] to recognize digoxigenin conjugated to the 240 kDa fluorescent protein phycoerythrin (PE). The conjugate was mixed with cells expressing NlpA-[Dig scFv] and treated with EDTA-lysozyme. A high cell fluorescence was observed indicating binding of digoxigenin-PE conjugate by the membrane anchored antibody (FIG. 7B). Overall, the accumulated data demonstrated that in cells treated with Tris-EDTA-lysozyme, scFvs anchored on the cytoplasmic membrane can readily bind to ligands ranging from small molecules to proteins of at least up to 240 kDa in molecular weight. Importantly, labeling with digoxigenin-PE followed by one round of flow cytometry resulted in an over 500-fold enrichment of bacteria expressing NlpA-[Dig scFv] from cells expressing a similar fusion with a scFv having unrelated antigen specificity.

B. Library Screening by APEx

A library of $1 \times 10^7$ members was constructed by errorprone PCR of the gene for the anti-PA 14B7 scFv and was fused to the NlpA membrane anchoring sequence. DNA sequencing of 12 library clones selected at random revealed an average of 2% nucleotide substitutions per gene. Following induction of NlpA-[14B7 mutant scFv] synthesis with IPTG, the cells were treated with Tris-EDTA-lysozyme, washed, and labeled with 200 nM PA-BODIPY™. Inner membrane integrity was monitored by staining with propidium iodide (PI). A total of $2 \times 10^8$ bacteria were sorted using an ultra-high throughput Cytomation Inc. MoFlo droplet deflection flow cytometer selectively gating for low PI fluorescence (630 nm emission) and high BODIPY™ fluorescence. Approximately 5% of the cells sorted with the highest 530 nm fluorescence (FL1) were collected, immediately restained with PI alone and resorted as above. Since no antigen was added during this second sorting cycle, only cells expressing antibodies that have slow dissociation kinetics remain fluorescent. The plating efficiency of this population was low, presumably due to a combination of potential scFv toxicity (Somerville et al., 1994; Hayhurst and Harris, 1999), Tris-EDTA-lysozyme treatment and exposure to the high shear flow cytometry environment. Therefore, to avoid loss of potentially high affinity clones, DNA encoding scFvs was rescued by PCR™ amplification of the approximately $1 \times 10^4$ fluorescent events recovered by sorting. It should be noted that the conditions used for PCR™ amplification result in the quantitative release of cellular DNA from the cells which have partially hydrolyzed cell walls due to the Tris-EDTA-lysozyme treatment during labeling. Following 30 rounds of PCR™ amplification, the DNA was ligated into pAPEx1 and transformed into fresh *E. coli*. A second round of sorting was performed exactly as above, except that in this case only the most fluorescent 2% of the population was collected and then immediately resorted to yield approximately 5,000 fluorescent events.

Figure 10:
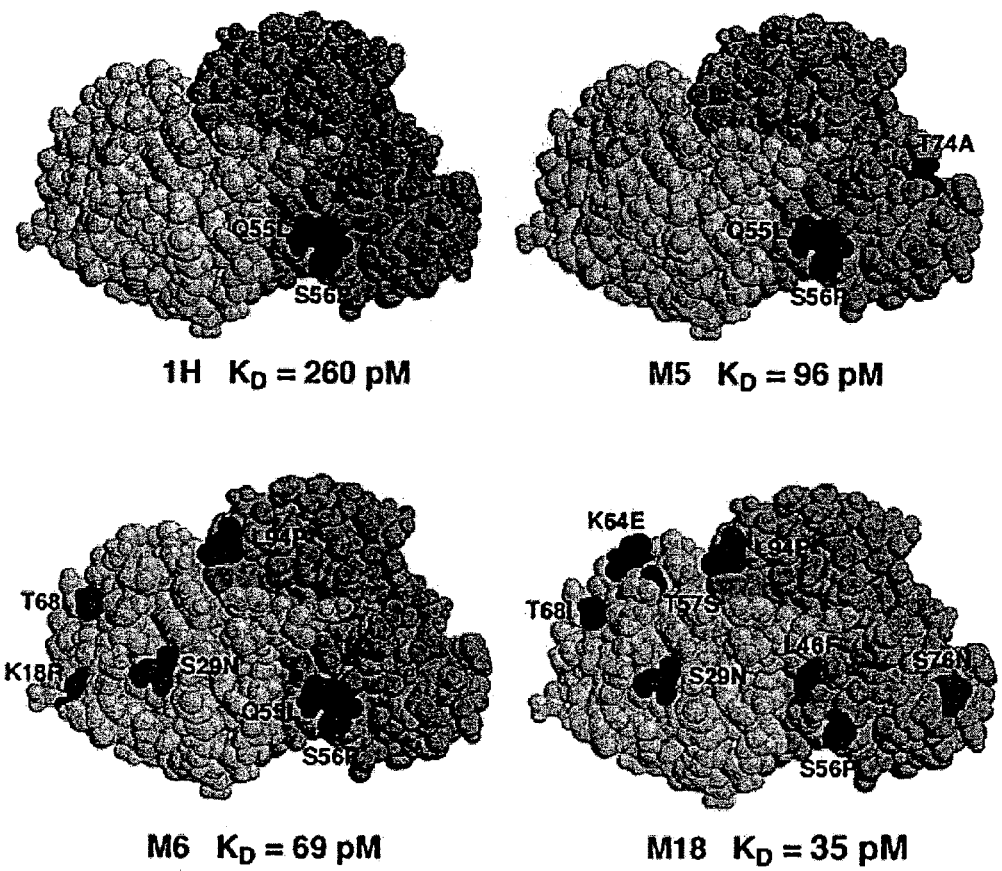
FIG. 10: View from the top of the antibody binding pocket showing the conformation and amino acid substitutions in the 1H, M5, M6 and M18 sequences.
Figure 11:
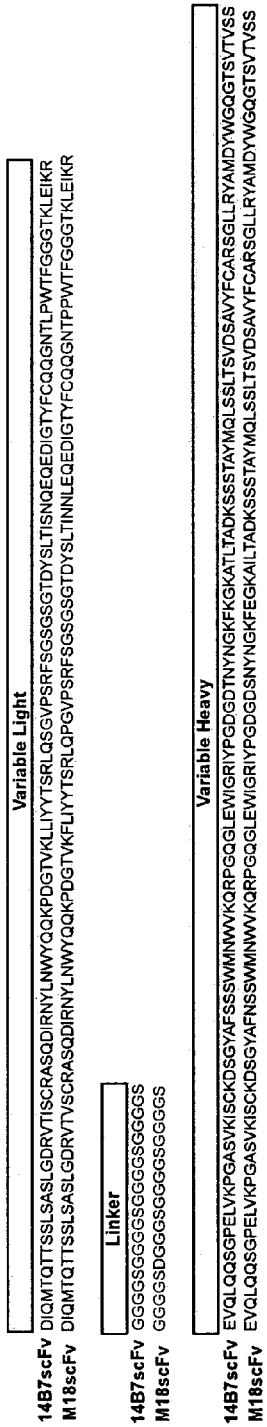
FIG. 11: Alignment of 14B7 scFv (SEQ ID NO:21) and M18 scFv (SEQ ID NO:23) sequences showing variable heavy and variable light chains and mutations made to improve binding affinity.

The scFv DNA from the second round was amplified by PCR™ and ligated into pMoPac16 (Hayhurst et al., 2003) for expression of the antibody fragments in soluble form in the scAb format. A scAb antibody fragment is comprised of an scFv in which the light chain is fused to a human kappa constant region. This antibody fragment format exhibits better periplasmic solubility compared to scFvs (Maynard et al., 2002; Hayhurst, 2000). 20 clones in the scAb format were picked at random and grown in liquid cultures. Following induction with IPTG, periplasmic proteins were isolated and the scAb proteins were rank-ordered with respect to their relative antigen dissociation kinetics, using surface plasmon resonance (SPR) analysis. 11 of the 20 clones exhibited slower antigen dissociation kinetics compared to the 14B7 parental antibody. The 3 scAbs with the slowest antigen dissociation kinetics were produced in large scale and purified by Ni chromatography followed by gel filtration FPLC. Interestingly, all the library-selected clones exhibited excellent expression characteristics and resulted in yields of between 4–8 mg of purified protein per L in shake flask culture. Detailed BIACore analysis indicated that all 3 clones exhibit a substantially lower $K_D$ for PA compared to the parental 14B7 antibody (FIGS. 8A and 8B). The improved $K_D$ resulted primarily from slower antigen dissociation, (i.e. slower $k_{off}$). The highest affinity clone, M18, exhibited $K_D$ of 35 pM, with a $k_{off}$ of $4.2 \times 10^{-5}$ M$^{-1}$ sec$^{-1}$ which corresponds to a M18-PA half life of 6.6 hours. This re over 120-fold affinity improvement compared to the parental antibody 14B7 ($K_D$=4.3 nM as determined by BIACore 3000). The mutations identified are given in FIG. 8B and a schematic showing the conformation of the 1H, M5, M6 and M18 antibodies is given in FIG. 10. The mutations for M5 were as follows: in the light chain, Q38R, Q55L, S56P, T74A, Q78L and in the heavy chain, K62R. For M6, the mutations were as follows: S22G, L33S, Q55L, S56P, Q78L AND L94 P, and in the heavy chain, S7P, K19R, S30N, T68I and M80L. For M18, the mutations were as follows: in the light chain, I21V, L46F, S56P, S76N, Q78L and L94P, and in the heavy chain, S30N, T57S, K64E and T68. FIG. 11 shows an alignment of 14B7 scFv (SEQ ID NO:21) and M18 scFv (SEQ ID NO:23) sequences indicating the variable heavy and variable light chains and mutations made. The nucleic acids encoding these sequences are given in SEQ ID NO:20 and SEQ ID NO:22, respectively.

The fluorescence intensity of Tris-EDTA-lysozyme permeabilized cells expressing NlpA fusions to the mutant antibodies varied in proportion to the antigen binding affinity. (FIG. 8C) For example, cells expressing the NlpA-[M18 scFv] protein displayed a mean fluorescence of 250 whereas the cells that expressed the parental 14B7 scFv exhibited a mean fluorescence of 30, compared to a background fluorescence of around 5 (FIG. 8B). Antibodies with intermediate affinities displayed intermediate fluorescence intensities in line with their relative affinity rank. The ability to resolve cells expressing antibodies exhibiting dissociation constants as low as 35 pM provides a reasonable explanation for why three unique very high affinity variants could be isolated and is indicative of the fine resolution that can be obtained with flow cytometric analysis.

The 3 clones analyzed in detail, M5, M6 and M18, contained 7, 12, and 11 amino acid substitutions, respectively. In earlier studies using phage display (Maynard et al., 2002), the inventors isolated a variant of the 14B7 scFv by three cycles, each consisting of 1) mutagenic error prone PCR™, 2) five rounds of phage panning and 3) DNA shuffling of the post-panning clones. The best clone isolated in that study, 1H, contained Q55L and S56P substitutions and exhibited a $K_D$ of 150 pM (as determined by a BIA-Core3000). These two mutations likely increase the hydrophobicity of the binding pocket adding to the mounting evidence that an increase in hydrophobic interactions is a dominant effect in antibody affinity maturation (Li et al., 2003). The same amino acid substitutions are also found in the M5 and M6 clones isolated by APEx. However, the presence of the additional mutations in these two clones conferred a further increase in affinity. It is noteworthy that the M5, M6 and M18 were isolated following a single round of asexual PCR™ yet they all had higher affinity relative to the best antibody that could be isolated by phage display, even following multiple rounds of sexual mutagenesis and selection.

M18, the highest affinity clone isolated by APEx, contained the S56P mutation but lacked the Q55L substitution found in 1H, M5, and M6. When the Q55L substitution was introduced into M18 by site specific mutagenesis, the resultant ScAb exhibited a further improvement in antigen binding ($K_D$=21 pM) with a $k_{on}$ of $1.1 \times 10^6$ M$^{-1}$ sec$^{-1}$ and a $k_{off}$ of $2.4 \times 10^{-5}$ sec$^{-1}$, corresponding to a complex half life of 11.6 hours. However, the introduction of this mutation reduced the yield of purified protein more than 5-fold to 1.2 mg/L in shake flask culture. The modified M18 sequence is given in SEQ ID NO:25 and the nucleic acid encoding this sequence is given in SEQ ID NO:24.

C. APEx of Phage Displayed scFv Antibodies

Numerous antibody fragments to important therapeutic and diagnostic targets have been isolated from repertoire libraries screened by phage display. It is desirable to develop a means for rapid antigen binding analysis and affinity maturation of such antibodies without the need for time consuming subcloning steps. Antibodies are most commonly displayed on filamentous phage via fusion to the N-terminus of the phage gene 3 minor coat protein (g3p) (Barbas et al., 1991). During phage morphogenesis, g3p becomes transiently attached to the inner membrane via its extreme C-terminus, before it can be incorporated onto the growing virion (Boeke and Model, 1982). The antibody fragments are thus both anchored and displayed in the periplasmic compartment. Therefore, the inventors evaluated whether g3p fusion proteins can be exploited for antibody library screening purposes using the APEx format. The high affinity anti-PA M18 scFv discussed above, the anti-digoxin/digoxigenin 26-10 scFv, and an anti-methamphetamine scFv (Meth) were cloned in frame to the N-terminus of g3p downstream from a lac promoter in phagemid pAK200, which is widely used for phage display purposes and utilizes a short variant of gene III for g3p display (Krebber et al., 1997). Following induction with IPTG, cells expressing scFv-g3p fusions were permeabilized by Tris-EDTA-lysozyme and labeled with the respective fluorescent antigens (FIG. 9). High fluorescence was obtained for all three scFvs only when incubated with their respective antigens. Significantly, the mean fluorescence intensity of the scFvs fused to the N-terminus of g3p was comparable to that obtained by fusion to the C-terminus of the NlpA anchor. The results in FIG. 9 demonstrate that: (i) large soluble domains can be tethered N-terminally to a membrane anchor; (ii) antibody fragments cloned into phagemids for display on filamentous phage can be readily analyzed by flow cytometry using the APEx format, and (iii) scFv antibodies can be anchored on the cytoplasmic membrane either as N- or C-terminal fusions without loss of antigen binding.

D. Discussion

The inventors have developed a allowing efficient selection of high affinity ligand-binding proteins, and particularly scFv antibodies, from combinatorial libraries. In one aspect, APEx is based on the anchoring of proteins to the outer side of the inner membrane, followed by disruption of the outer membrane prior to incubation with fluorescently labeled antigen and FC sorting. This strategy offers several advantages over previous bacterial periplasmic and surface display approaches: 1) by utilizing a fatty acylated anchor to retain the protein in the inner membrane, a fusion as short as 6 amino acids is all that was required for the successful display, potentially decreasing deleterious effects that larger fusions may impose; 2) the inner membrane lacks molecules such as LPS or other complex carbohydrates that can sterically interfere with large antigen binding to displayed antibody fragments; 3) the fusion must only traverse one membrane before it is displayed; 4) both N- and C-terminal fusion strategies can be employed; and 5) APEx can be used directly for proteins expressed from popular phage display vectors. This latter point is particularly important because it enables hybrid library screening strategies, in which clones from a phage panning experiment can be quantitatively analyzed or sorted further by flow cytometry without the need for any subcloning steps.

APEx can be employed for the detection of antigens ranging from small molecules (e.g. digoxigenin and methamphetamine <1 kDa) to phycoerythrin conjugates (240 kDa). In fact, the phycoerythrin conjugate employed in FIG. 3B is not meant to define an upper limit for antigen detection, as it is contemplated that larger proteins may be used as well.

In the example, genes encoding scFvs that bind the fluorescently labeled antigen, were rescued from the sorted cells by PCR™. An advantage of this approach is that it enables the isolation of clones that are no longer viable due to the combination of potential scFv toxicity, Tris-EDTA-lysozyme disruption, and FC shear forces. In this way, diversity of isolated clones is maximized. Yet another advantage of PCR™ rescue is that the amplification of DNA from pooled cells can be carried out under mutagenic conditions prior to subcloning. Thus, following each round of selection random mutations can be introduced into the isolated genes, simplifying further rounds of directed evolution (Hanes and Pluckthun, 1997). Further, PCR™ conditions that favor template switching among the protein encoding genes in the pool may be employed during the amplification step to allow recombination among the selected clones. It is likely that PCR™ rescue would be advantageous in other library screening formats as well.

An important issue with any library screening technology is the ability to express isolated clones at a high level. Existing display formats involve fusion to large anchoring sequences which can influence the expression characteristics of the displayed proteins. For this reason, scFvs that display well may not necessarily be amenable to high expression in soluble form as non-fusion proteins (Hayhurst et al., 2003). In contrast, the short (6 amino acid) tail that may be used for N-terminal tethering of proteins onto the cytoplasmic membrane in the current invention is unlikely to affect the expression characteristics of the fusion. Consistent with this hypothesis, all three affinity enhanced clones to the anthrax PA toxin isolated by APEx exhibited excellent soluble expression characteristics despite having numerous amino acid substitutions. Similarly, well-expressing clones have been obtained in the affinity maturation of a methamphetamine antibody, suggesting that the isolation of clones that can readily be produced in soluble form in bacteria at a large scale might be an intrinsic feature of selections with the invention.

In this example, the inventors employed APEx for affinity maturation purposes and have engineered scFvs to the *B. anthracis* protective antigen exhibiting $K_D$ values as low as 21 pM. The scFv binding site exhibiting the highest affinity for PA has been humanized, converted to full length IgG and its neutralizing potential to anthrax intoxication is being evaluated in preclinical studies. In addition to affinity maturation, APEx can be exploited for several other protein engineering applications including the analysis of membrane protein topology, whereby a scFv antibody anchored in a periplasmic loop is able to bind fluorescent antigen and serves as a fluorescent reporter, and also, the selection of enzyme variants with enhanced function. Notably, APEx can be readily adapted to enzyme library sorting, as the cell envelope provides sites for retention of enzymatic catalytic products, thereby enabling selection based directly on catalytic turnover (Olsen et al., 2000). The inventors are also evaluating the utilization of APEx for the screening of ligands to membrane proteins. In conclusion, it has been demonstrated that anchored periplasmic expression has the potential to facilitate combinatorial library screening and other protein engineering applications.

E. Materials and Methods

1. Recombinant DNA Techniques

The leader peptide and first six amino acids of the mature NlpA protein flanked by NdeI and SfiI sites was amplified by whole cell PCR of XL1-Blue (Stratagene, CA) using primers

```
BRH#08 5'-GAAGGAGATATACATATGAAACTGACAACACATCATCTA-3' and    (SEQ ID NO:6)

BRH#09 5'-CTGGGCCATGGCCGGCTGGGCCTCGCTGCTACTCTGGTCGCAACC-3'. (SEQ ID NO:7)
```

The resulting NlpA fragment was used to replace the pelB leader sequence of pMoPac1 (Hayhurst et al., 2003) via NdeI and SfiI to generate pAPEx1. scFv specific for digoxin (Chen et al., 1999), *Bacillus anthracis* protective antigen PA (Maynard et al., 2002) and methamphetamine were inserted downstream of the NlpA fragment in pAPEx1 via the non-compatible SfiI sites. Corresponding g3p fusions of the scFv were made by cloning the same genes into phage display vector pAK200 (Krebber et al., 1997).

2. Growth Conditions

*E. coli* ABLE C™ (Stratagene) was the host strain used throughout. *E. coli* transformed with the pAPEx1 or pAK200 derivatives were inoculated in terrific broth (TB) supplemented with 2% glucose and chloramphenicol at 30 ug/ml to an OD600 of 0.1. Cell growth and induction were performed as described previously (Chen et al., 2001). Following induction, the cellular outer membrane was permeabilized as described (Neu and Heppel, 1965). Briefly, cells (equivalent to approx 1 ml of 20 OD600) were pelleted and resuspended in 350 μl of ice-cold solution of 0.75M sucrose, 0.1M Tris-HCl pH 8.0, 100 μg/ml hen egg lysozyme. 700 μof ice-cold 1 mM EDTA was gently added and the suspension left on ice for 10 min. 50 μl of 0.5M $MgCl_2$ was added and the mix left on ice for a further 10 min. The resulting cells were gently pelleted and resuspended in phosphate buffered saline (1×PBS) with 200 nM probe at room temperature for 45 min, before evaluation by FC.

3. Fluorescent Probe

The synthesis of digoxigenin-BODIPY has been described previously (Daugherty et al., 1999). Methamphetamine-fluorescein conjugate was a gift from Roche Diagnostics. Purified PA protein kindly provided by S. Leppla NIH, was conjugated to BODIPY™ at a 1 to 7 molar ratio with bodipy FL SE D-2184 according to the manufacturers instructions. Unconjugated BODIPY™ was removed by dialysis.

To synthesize digoxigenin-phycoerythrin, R-phycoerythrin and 3-amino-3-dioxydigxigenin hemisuccinamide, succinimidyl ester (Molecular Probes) were conjugated at a 1 to 5 molar ratio according to the manufacturers instructions. Free digoxigenin was removed by dialysis in excess PBS.

4. Affinity Maturation of scFv Libraries with FC

Libraries were made from the 14B7 parental scFv using error prone PCR using standard techniques (Fromant et al., 1995) and cloned into the pAPEx1 expression vector. Upon transformation, induction and labeling the cells were then stained with propidium iodide (PI emission 617 nm) to monitor inner membrane integrity. Cells were analyzed on a MoFlo (Cytomation) droplet deflection flow cytometer using 488 nm Argon laser for excitation. Cells were selected based on improved fluorescence in the Fluorescein/Bodipy FL emission spectrum detecting through a 530/40 band pass filter and for the absence of labeling in PI emission detecting through a 630/40 band pass filter.

E. coli captured after the first sort were immediately resorted through the flow cytometer. Subsequently, the scFv genes in the sorted cell suspension were amplified by PCR™. Once amplified, the mutant scFv genes were then recloned into pAPEx1 vector, retransformed into cells and then grown overnight on agar plates at 30° C. The resulting clones were subjected to a second round of sorting plus resorting as above, before scFv genes were subcloned into pMoPac16 (Hayhurst et al., 2003) for expression of scAb protein.

5. Surface Plasmon Resonance Analysis

Monomeric scAb proteins were purified by IMAC/size-exclusion FPLC as described previously (Hayhurst et al., 2003). Affinity measurements were obtained via SPR using a BIACore3000 instrument. Approximately 500RUs of PA was coupled to a CM5 chip using EDC/NHS chemistry. BSA was similarly coupled and used for in line subtraction. Kinetic analysis was performed at 25° C. in BIA HBS-EP buffer at a flow rate 100 µl/min. Five two fold dilutions of each antibody beginning at 20 nM were analyzed in triplicate.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Am J Pediatr Hematol Oncol*, 12(4): 480–9, 1990.
Almendro et al., *J Immunol.* 157:5411, 1996.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Atherton et al., *Biol. of Reproduction*, 32:155, 1985.
Banerji et al., *Cell*, 27:299, 1981.
Banerji et al., *Cell*, 35:729, 1983.
Barbas et al., *Proc. Natl. Acad. Sci. USA*, 88:7978–7982, 1991.
Bellus, *J Macromol. Sci. Pure Appl. Chem.*, RS3241(1): 1355–1376, 1994.
Berberian et al., *Science*, 261:1588–1591, 1993.
Berkhout et al., *Cell*, 59:273, 1989.
Berrier et al., *J Bacteriol.*, 182:248, 2000.
Blanar et al, *EMBO J*, 8:1139, 1989.
Boder and Wittrup, *Methods Enzymol.*, 328:430–444, 2000.
Boder et al., *Proc. Natl. Acad. Sci. USA*, 97:10701–10705, 2000.
Bodine and Ley, *EMBO J.*, 6:2997, 1987.
Boeke and Model, *Proc. Natl. Acad. Sci. USA*, 79:5200–5204, 1982.
Boeke et al., *Mol. Gen. Genet.*, 186: 1982.
Boshart et al., *Cell*, 41:521, 1985.
Bosze et al., *EMBO J.*, 5:1615, 1986.
Braddock et al., *Cell*, 58:269, 1989.
Bukau et al., *J. Bacteriol.*, 163:61, 1985.
Bulla and Siddiqui, *J. Virol.*, 62:1437, 1986.
Burioni et al., *Res. Virol.*, 149:327, 1998.
Burman et al., *J. Bacteriol.*, 112:1364, 1972.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carter et al., Nucleic Acids Res 13:4431, 1985.
Celander and Haseltine, *J. Virology*, 61:269, 1987.
Celander et al., *J. Virology*, 62:1314, 1988.
Chandler et al., *Cell*, 33:489, 1983.
Chang et al., *Mol. Cell. Biol.*, 9:2153, 1989.
Chattejee et al., *Proc. Nat'l Acad. Sci. USA*., 86:9114, 1989.
Chen et al., *J. Mol. Biol.*, 293:865, 1999.
Chen et al., *Nat. Biotechnol.*, 19:537–542, 2001.
Chen et al., *Protein Eng.*, 12:349–356, 1999.
Choi et al., *Cell*, 53:519, 1988.
Chowdhury and Pastan, *Nat. Biotech.*, 17:568, 1999.
Cleary et al., Trends Microbiol., 4:131–136, 1994.
Coffin, In: *Virology*, ed., New York: Raven Press, pp. 1437–1500, 1990.
Cohen et al., *Proc. Nat'l Acad. Sci. USA* 75:472, 1987.
Coia et al., *Gene* 201:203, 1997.
Corey et al., *Gene*, 128:129, 1993.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dall'Acqua and Carter, *Curr. Opin. Struct. Biol.*, 8:443, 1998.
Dandolo et al., *J. Virology*, 47:55, 1983.
Daugherty et al., *J. Immunol. Methods*. 243:211, 2000.
Daugherty et al., *Proc. Natl. Acad. Sci. USA*, 97:2029–2034, 2000.
Daugherty et al., *Prot. Eng.*, 11:825, 1998.
Daugherty et al., *Protein Eng.*, 12:613–621, 1999.
De Haard et al., *J. Biol. Chem.*, 274:18218, 1999.
De Jager R et al., *Semin Nucl Med* 23:165, 1993.
De Villiers et al., *Nature*, 312:242, 1984.
De Wildt et al., Nat. Biotechnol. 18: 989, 2000.
Decad and Nikaido, *J. Bacteriol.*, 128:325, 1976.
Deng et al., *J. Biol. Chem.*, 269:9533, 1994.
Deng et al., *Proc. Natl. Acad. Sci. USA*. 92:4992, 1995.
Deschamps et al., *Science*, 230:1174, 1985.
Dholakia et al., J. Biol. Chem., 264, 20638–20642, 1989.
Doolittle M H and Ben-Zeev O, *Methods Mol Biol.*, 109: 215, 1999.
Duenas and Borrebaeck, *Biotechnology*, 12:999, 1994.
Edbrooke et al., *Mol. Cell. Biol.*, 9:1908, 1989.
Edlund et al., *Science*, 230:912, 1985.
Farmer et al., *FEMS Microbiol. Lett.*, 176:11, 1999.
Feldhaus et al., *Nat. Biotechnol.*, 21:163–170, 2003.
Feng and Holland, *Nature*, 334:6178, 1988.
Firak and Subramanian, *Mol. Cell. Biol.*, 6:3667, 1986.
Frohman, In: *PCR PROTOCOLS: A GUIDE TO METHODS AND APPLICATIONS*, Academic Press, N.Y., 1990.

Fromant et al., *Anal. Biochem.*, 224:347–353, 1995.
Fujita et al., *Cell*, 49:357, 1987.
Gennity and Inouye *J. Bacteriol* 174(7):2095, 1992
Georgiou et al., *Nat. Biotechnol.* 15:29, 1997.
Georgiou, *Adv. Protein Chem.*, 55:293–315, 2000.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Nat'l Acad. Sci. USA*, 85:1447, 1988.
Goodbourn et al., *Cell*, 45:601, 1986.
Gough et al., *J. Immunol. Met.*, 228:97, 1999.
Greene et al., *Immunology Today*, 10:272, 1989.
Griep et al., *Prot. Exp. Purif.*, 16:63, 1999.
Griffiths et al., *EMBO J.*, 13: 3245, 1994.
Grosschedl and Baltimore, *Cell*, 41:885, 1985.
Gulbis and Galand, *Hum Pathol* 24:1271, 1993.
Hanes and Pluckthun, *Proc. Natl. Acad. Sci. USA*, 94:4937–4942, 1997.
Haslinger and Karin, *Proc. Nat'l Acad. Sci. USA.*, 82:8572, 1985.
Hauber and Cullen, *J. Virology*, 62:673, 1988.
Hawkins et al., *J. Mol. Biol.*, 226:889, 1992.
Hayhurst and Georgiou, *Curr. Opin. Chem. Biol.*, 5:683–689, 2001.
Hayhurst and Harris, *Protein Expr. Purif.*, 15:336–343, 1999.
Hayhurst et al., *J. Immunol. Methods*, 276:185–196, 2003.
Hayhurst, *Protein Expr. Purif.*, 18:1–10, 2000.
Hearing et al., *J. Virol.*, 67:2555–2558, 1987.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10: 1959, 1990.
Hobot et al., *J. Bacteriol.* 160:143, 1984.
Hoess, *Chem. Rev.*, 101:3205–3218, 2001.
Holbrook et al., *Virology*, 157:211, 1987.
Hoogenboom et al., *Adv. Drug. Deliv. Rev.*, 31:5, 1998.
Horlick and Benfield, *Mol. Cell. Biol.*, 9:2396, 1989.
Hsiung et al, *Biotechnology*, 4:991, 1994.
Huang et al., *Cell*, 27:245, 1981.
Hudson and Souriau, *Nat. Med.* 9:129–134, 2003.
Hudson, *Curr. Opin. Biotechnol.*, 9:395, 1998.
Hultgren et al., *Bacterial Adhesins Assembly*, Vol. 2., 1996.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*. 85:9436, 1988.
Irvin et al, *J. Bacteriol.*, 145:1397, 1981.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jeffrey et al., *Proc. Natl. Acad. Sci. USA*. 90:10310, 1993.
Johns et al., *J. Immunol. Methods*, 239:137, 2000.
Johnson et al., *Mol. Cell. Biol.*, 9:3393, 1989.
Jouenne and Junter, FEMS Microbiol. Lett., 56:313, 1990.
Kadesch and Berg, *Mol. Cell. Biol.*, 6:2593, 1986.
Kang et al., *Science*, 240:1034–1036, 1988.
Karin et al., *Mol. Cell. Biol.*, 7:606, 1987.
Katinka et al., *Cell*, 20:393, 1980.
Katinka et al., *Nature*, 290:720, 1981.
Kawamoto et al., *Mol. Cell. Biol.*, 8:267, 1988.
Khatoon et al., Ann. of Neurology, 26, 210–219, 1989.
Kiledjian et al., *Mol. Cell. Biol.*, 8:145, 1988.
King et al., *J. Biol. Chem.*, 269:10218, 1989.
Kjaer et al., *FEBS Lett.*, 431:448, 1998.
Klamut et al., *Mol. Cell. Biol.*, 10:193, 1990.
Knappick et al., *J. Mol. Biol.*, 296:57, 2000.
Koch et al., *Mol. Cell. Biol.*, 9:303, 1989.
Kohler et al., *Methods Enzymol.*, 178:3, 1989.
Kraus et al., *FEBS Lett.*, 428:165, 1998.
Krebber et al., *Gene*, 178:71, 1996.
Krebber et al., *J. Immunol. Methods*, 201:35–55, 1997.
Kreier et al., Infection, Resistance and Immunity, Harper & Row, New York, (1991)).
Kriegler and Botchan, *In: Eukaryotic Viral Vectors*, Y. Gluzman, ed., Cold Spring Harbor: Cold Spring Harbor Laboratory, NY, 1982.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., *In: Gene Expression*, D. Hamer and M. Rosenberg, eds., New York: Alan R. Liss, 1983.
Kuhl et al., *Cell*, 50:1057, 1987.
Kunz et al., *Nucl. Acids Res.*, 17:1121, 1989.
Kwoh et al, *Proc Natl Acad Sci USA*. 86:1173, 1989.
Labischinski et al., *J. Bacteriol.*, 162:9, 1985.
Lareyre et al., *J Biol Chem.*, 274:8282, 1999.
Larsen et al., *Proc. Nat'l Acad. Sci. USA.*, 83:8283, 1986.
Laspia et al., *Cell*, 59:283, 1989.
Latimer et al., *Mol. Cell. Biol.*, 10:760, 1990.
Lee et al., *J Auton Nerv Syst*. 74:86, 1997
Lee et al., *Nature*, 294:228, 1981.
Lenert et al., *Science*, 248:1639–1643, 1990.
Levinson et al., *Nature*, 295:79, 1982.
Levitan, *J. Mol. Biol.*, 277:893, 1998.
Li et al., *Nat. Struct. Biol.*, 10:482–488, 2003.
Lin et al., *Mol. Cell. Biol.*, 10:850, 1990.
Luria et al., *EMBO J.*, 6:3307, 1987.
Lusky and Botchan, *Proc. Nat'l Acad. Sci. USA.*, 83:3609, 1986.
Lusky et al., *Mol. Cell. Biol.*, 3:1108, 1983.
MacKenzie and To, *J. Immunol. Methods*, 220:39, 1998.
MacKenzie et al., *J. Biol. Chem.*, 271:1527, 1996.
Maenaka et al., *Biochem Biophys Res Commun.*, 218:682, 1996.
Majors and Varmus, *Proc. Nat'l Acad. Sci. USA.*, 80:5866, 1983.
Malmborg et al., *J. Immunol. Methods*, 198:51, 1996.
Marciano et al., *Science* 284:1516, 1999.
Marks et al., *Bio/Technol.* 10:779, 1992.
Marks et al., *J. Mol. Biol.*, 222:581, 1991.
Martinez et al., *Biochemistry*, 35:1179, 1996.
Martinez et al., *J. Biotechnol.*, 71:59, 1999.
Masuda K et al. *PNAS* 99(11):7390, 2002.
Maynard et al., *Nat. Biotechnol.*, 20:597–601, 2002.
McNeall et al., *Gene*, 76:81, 1989.
Miksicek et al., *Cell*, 46:203, 1986.
Mingarro et al., *Trends Biotechnol.*, 15:432–437, 1997.
Miroux and Walker, *J. Mol. Biol.*, 260:289–298, 1996.
Mitchell et al., *Ann. N.Y Acad. Sci.*, 690:153, 1993.
Mordacq and Linzer, *Genes and Dev.*, 3:760, 1989.
Moreau et al., *Nucl. Acids Res.*, 9:6047, 1981.
Morrison, et al., *Proc. Nat'l. Acad. Sci USA*. 81:6851, 1984.
Muesing et al., *Cell*, 48:691, 1987.
Munson & Pollard, Anal. Biochem. 107:220, 1980.
Mutuberria et al., *J. Immunol. Methods*, 231:65, 1999.
Nakae, *J. Biol. Chem.*, 251:2176, 1976.
Neu and Heppel, *J. Biol. Chem.*, 240:3685–3692, 1965.

Nikaido and Nakae, *Adv. Microb. Physiol.*, 20:163, 1979.
Nikaido and Vaara, *Microbiol. Rev.* 49:1, 1985.
Nissim et al., *EMBO J.*, 13:692, 1994.
Nomoto et al., *Gene*, 236:259, 1999.
Ohara et al., "One-sided polymerase chain reaction: the amplification of cDNA,"
Oka et al, Proc. Natl. Acad. Sci. U.S.A., Vol 82, pp 7212–7216, November 1985
Olsen et al., *Nat. Biotechnol*, 18:1071–1074, 2000.
O'Shannessy et al., J. Immun. Meth., 99, 153–161, 1987.
Owens & Haley, J. Biol. Chem., 259:14843–14848, 1987.
Painbeni et al., *Proc Natl. Acad. Sci. USA*, 94:6712, 1997.
Palmiter et al., *Nature*, 300:611, 1982.
Pech et al., *Mol. Cell. Biol.*, 9:396, 1989.
Perez-Stable and Constantini, *Mol. Cell. Biol.*, 10:1116, 1990.
Picard and Schaffner, *Nature*, 307:83, 1984.
Pini et al., *J. Biol. Chem.*, 273:21769, 1998.
Pinkert et al., *Genes and Dev.*, 1:268, 1987.
Ponta et al., *Proc. Nat'l Acad Sci. USA.*, 82:1020, 1985.
Porton et al., *Mol. Cell. Biol.*, 10:1076, 1990.
Potter & Haley, Meth. in Enzymol., 91, 613–633, 1983.
Pugsley, *Microbiol. Rev.*, 57:50–108, 1993.
Queen and Baltimore, *Cell*, 35:741, 1983.
Quinn et al., *Mol. Cell. Biol.*, 9:4713, 1989.
Rakonjac and Model, *J. Mol. Biol.*, 282:25, 1998.
Rakonjac et al., *J. Mol. Biol.*, 289:1253, 1999.
Rao and Torriani, *J. Bacteriol.*, 170, 5216, 1988.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ripe et al., *Mol. Cell. Biol.*, 9:2224, 1989.
Rittling et al., *Nucl. Acids Res.*, 17:1619, 1989.
Rodi and Makowski, *Curr. Opin. Biotechnol.*, 10: 87–93, 1999.
Rosen et al., *Cell*, 41:813, 1988.
Sagt et al., *Appl. Environ. Microbiol.*, 68:2155–2160, 2002.
Sakai et al., *Genes and Dev.*, 2:1144, 1988.
Sambrook et al., In: *Molecular Cloning: A Laboratory Manual*, Vol. 1, Cold Spring Harbor Laboratory Press, Cold Spring Harbor, N.Y., Ch. 7,7.19–17.29, 1989.
Samuelson et al., *Nature*, 406:637–641, 2000.
Sasso et al., *J. Immunol.*, 142:2778–2783, 1989.
Satake et al., *J. Virology*, 62:970, 1988.
Sblattero and Bradbury, *Nat. Biotechnol.*, 18:75, 2000.
Schaffner et al., *J. Mol. Biol.*, 201:81, 1988.
Searle et al., *Mol. Cell. Biol.*, 5:1480, 1985.
Seydel et al., *Mol. Microbiol.*, 34:810–821, 1999.
Sharp and Marciniak, *Cell*, 59:229, 1989.
Shaul and Ben-Levy, *EMBO J.*, 6:1913, 1987.
Sheets et al., *Proc. Natl. Acad. Sci. USA.*, 95:6157, 1998.
Sherman et al., *Mol. Cell. Biol.*, 9:50, 1989.
Shorki et al., J. Immunol., 146:936–940, 1991.
Shusta et al., *J. Mol. Biol.*, 292:949, 1999.
Silvermann et al., *J. Clin. Invest.*, 96:417–426, 1995.
Sleigh and Lockett, *J. EMBO*, 4:3831, 1985.
Smith, *Science*, 228:1315–1317, 1985.
Somerville et al., *Appl. Microbiol. Biotechnol.*, 42:595–603, 1994.
Spalholz et al., *Cell*, 42:183, 1985.
Spandau and Lee, *J. Virology*, 62:427, 1988.
Spandidos and Wilkie, *EMBO J.*, 2:1193, 1983.
Stathopoulos et al., *Appl. Microbiol. Biotechnol.*, 45:112–119, 1996.
Stephens and Hentschel, *Biochem. J.*, 248:1, 1987.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
T. J. Gibson, PhD thesis, University of Cambridge (1984).
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Thompson et al., *J. Mol. Biol.* 256, 77, 1999????.
Thorstenson et al., *J. Bacteriol.*, 179:5333, 1997.
Tomlinson et al., *J. Mol. Biol.* 227:776, 1992.
Tronche et al., *Mol. Biol. Med.*, 7:173, 1990.
Tronche et al., *Mol. Cell. Biol.*, 9:4759, 1989.
Trudel and Constantini, *Genes and Dev.*, 6:954, 1987.
Tsumaki et al., *J Biol Chem.* 273:22861, 1998.
Van Wielink and Duine, *Trends Biochem Sci.*, 15:136, 1990.
Vannice and Levinson, *J. Virology*, 62:1305, 1988.
Vasseur et al., *Proc. Natl. Acad. Sci. USA.*, 77:1068, 1980.
Vaughan et al., *Nat. Biotechnol.*, 14:309, 1996.
Walker et al., *Nucleic Acids Res.* 20:1691, 1992
Wang and Calame, *Cell*, 47:241, 1986.
Waterhouse et al., Nucl. Acids Res. 21, 2265–2266 (1993)
Watson, M. Nucleic Acids Research, Vol 12, No. 13, 1984, pp. 5145–5164),
Weber et al., *Cell*, 36:983, 1984.
Weinberger et al. *Mol. Cell. Biol.*, 8:988, 1984.
Winoto and Baltimore, *Cell*, 59:649, 1989.
Winter et al., *Ann. Rev. Immunol.* 12: 433, 1994.
Wittrup, *Nat. Biotechnol.*, 18:1039–1040, 2000.
Wu et al., *Biochem Biophys Res Commun.* 233:221, 1997.
Yakushi et al., *Nat. Cell. Biol.*, 2:212–218, 2000.
Yakushi T. et al. *Journal of Bacteriology* 179(9):2857, 1997.
Yamaguchi and Inouye., *Journal of Bacteriology* 170 no. 8: 3747, 1988.
Yamaguchi et al., *Cell*, 53:423–432, 1988.
Yu et al., *J. Biol. Chem.*, 261:2284–2288, 1986.
Yutzey et al. *Mol. Cell. Biol.*, 9:1397, 1989.
Zhao-Emonet et al., *Gene Ther.* 6:1638, 1999.

What is claimed is:

1. A method of obtaining a bacterium comprising a nucleic acid sequence encoding a binding polypeptide having specific affinity for a target ligand comprising the steps of:

(a) providing a Gram negative bacterium comprising an inner and an outer membrane and a periplasm, said bacterium expressing a nucleic acid sequence encoding a candidate binding polypeptide, wherein the candidate binding polypeptide is exposed within the periplasm of said bacterium;

(b) contacting the bacterium with a labeled ligand under conditions wherein the labeled ligand contacts the binding polypeptide; and (c) selecting said bacterium based on the presence of said labeled ligand bound to said candidate binding polypeptide.

2. The method of claim 1, further defined as a method of obtaining a nucleic acid sequence encoding a binding polypeptide having a specific affinity for a target ligand, the method further comprising the step of:
   (d) cloning a nucleic acid sequence encoding said candidate binding polypeptide from said bacterium.

3. The method of claim 1, wherein said nucleic acid sequence as further defined as operably linked to a leader sequence that directs the expression of said fusion polypeptide to the outer side of the inner membrane.

4. The method of claim 1, wherein said Gram negative bacterium is an *E. coli* bacterium.

5. The method of claim 1, wherein step (a) is further defined as comprising providing a population of Gram negative bacteria.

6. The method of claim 1, wherein the candidate binding polypeptide is anchored to the outer side of the inner membrane of said bacterium.

7. The method of claim 5, wherein said population of bacteria is further defined as collectively expressing a plurality of nucleic acid sequences encoding a plurality of candidate binding polypeptides.

8. The method of claim 2, wherein the bacterium is non-viable.

9. The method of claim 2, wherein the bacterium is viable.

10. The method of claim 2, wherein cloning comprises amplification of the nucleic acid sequence.

11. The method of claim 7, wherein said plurality of nucleic acid sequences are further defined as encoding a fusion polypeptide comprising a candidate binding polypeptide and a polypeptide anchored to the to the outer side of the inner membrane of the bacterium.

12. The method of claim 5, wherein said population of bacteria is produced by a method comprising the steps of:
   (a) preparing a plurality of nucleic acid sequences encoding a plurality of fusion polypeptides comprising a candidate binding polypeptide and an inner membrane anchor polypeptide; and
   (b) transforming a population of Gram negative bacteria with said DNA inserts.

13. The method of claim 5, wherein said population of Gram negative bacteria is contacted with said labeled ligand.

14. The method of claim 5, wherein selecting in step (c) is further defined as comprising at least two rounds of selecting, wherein a sub-population of bacteria is selected based on the presence of said labeled ligand bound to said candidate binding polypeptide and further wherein the sub-population is subjected to at least one additional selection based on the presence of said labeled ligand bound to said candidate binding polypeptide.

15. The method of claim 14, wherein from about two to six rounds of selecting are carried out.

16. The method of claim 14, wherein selecting is carried out by flow-cytometry or magnetic separation.

17. The method of claim 1, wherein said candidate binding polypeptide is further defined as an antibody or fragment thereof.

18. The method of claim 17, wherein said candidate binding polypeptide is further defined as a scAb, Fab or scFv.

19. The method of claim 1, wherein said candidate binding polypeptide is further defined as a binding protein of at least 40 amino acids other than an antibody.

20. The method of claim 1, wherein said candidate binding polypeptide is further defined as comprising less than 39 amino acids.

21. The method of claim 1, wherein said candidate binding polypeptide is further defined as an enzyme.

22. The method of claim 1, wherein said labeled ligand is selected from the group consisting of a peptide, a polypeptide, an enzyme, a nucleic acid, a small molecule (<1 kDa) and a synthetic molecule.

23. The method of claim 1, wherein said labeled ligand is further defined as fluorescently labeled.

24. The method of claim 1, wherein said nucleic acid encoding a candidate binding polypeptide if further defined as flanked by known nucleic acid sequences.

25. The method of claim 1, further comprising treating said bacterium to increase the permeability of the outer membrane of said bacterium to said labeled ligand.

26. The method of claim 25, wherein treating comprises a method selected from the group consisting of: treatment with hyperosmotic conditions, treatment with physical stress, infecting the bacterium with a phage, treatment with lysozyme, treatment with EDTA, treatment with a digestive enzyme and treatment with a chemical that disrupts the outer membrane.

27. The method of claim 26, wherein treating comprises a combination of said methods.

28. The method of claim 27, wherein treating comprises treatment with lysozyme and EDTA.

29. The method of claim 25, wherein treating comprises heating the bacterium with a combination of physical, chemical and enzyme disruption of the outer membrane.

30. The method of claim 1, wherein said bacterium comprises a mutation conferring increased permeability of said outer membrane to said labeled ligand.

31. The method of claim 1, further comprising removing the outer membrane of said bacterium.

32. The method of claim 1, wherein said bacterium is grown at a sub-physiological temperature.

33. The method of claim 32, wherein said sub-physiological temperature is about 25° C.

34. The method of claim 1, further comprising removing labeled ligand not bound to said candidate binding polypeptide.

35. The method of claim 1, further defined as comprising contacting the bacterium with at least two labeled ligands.

36. The method of claim 1, wherein said selecting comprises flow cytometry.

37. The method of claim 1, wherein said selecting comprises magnetic separation.

38. The method of claim 1, wherein said ligand and said candidate binding polypeptide are reversibly bound.

39. The method of claim 6, wherein the polypeptide anchored to the outer side of the inner membrane comprises a transmembrane protein or fragment thereof.

40. The method of claim 6, wherein the polypeptide anchored to the outer side of the inner membrane comprises a sequence selected from the group consisting of: the first two amino acids encoded by the *E. coli* NlpA gene, the first six amino acids encoded by the *E. coli* NlpA gene, the gene III protein of filamentous phage or a fragment thereof, an inner membrane lipoprotein or fragment thereof.

41. The method of claim 6, wherein the polypeptide anchored to the outer side of the inner membrane is anchored via an N- or C-terminus of the polypeptide.

42. The method of claim 40, wherein the sequence is an inner membrane lipoprotein or fragment thereof selected from the group consisting of: AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, Dsb, B, DsbD, TouB, TatC, CheY, TraB, ExbD, ExbB and Aas.

43. A method of obtaining a bacteria comprising a nucleic acid sequence encoding at least a first binding polypeptide having specific affinity for a target ligand comprising the steps of:
  (a) providing a Gram negative bacterium comprising an inner and an outer membrane and a periplasm, said bacteria expressing a nucleic acid sequence encoding a least a candidate binding polypeptide, wherein the candidate binding polypeptide is exposed within the periplasm of said bacterium;
  (b) contacting the bacterium with a fluorescently labeled ligand under conditions wherein the labeled ligand contacts the binding polypeptide; and
  (c) selecting said bacterium for the presence of the fluorescently labeled ligand using Fluorescence Activated Cell Sorting (FAGS).

44. The method of claim 43, further defined as a method of obtaining a nucleic acid sequence encoding a binding polypeptide having a specific affinity for a target ligand, the method further comprising the step of:
  (d) cloning a nucleic acid sequence encoding said candidate binding polypeptide from said bacterium.

45. The method of claim 43, further defined as comprising providing a population of Gram negative bacteria.

46. The method of claim 45, wherein said population of bacteria is further defined as collectively expressing a plurality of nucleic acid sequences encoding a plurality of candidate binding polypeptides.

47. The method of claim 43, wherein the candidate binding polypeptide is anchored to the outer side of the inner membrane of said bacterium.

48. A method of obtaining a nucleic acid sequence encoding a binding polypeptide having a specific affinity for a target ligand comprising the steps of:
  (a) providing a Gram negative bacterium comprising an inner and an outer membrane and a periplasm, said bacterium expressing a nucleic acid sequence encoding a candidate binding polypeptide, wherein the candidate binding polypeptide is anchored to the outer side of the inner membrane of said bacterium;
  (b) disrupting the outer membrane of said bacterium;
  (c) contacting the bacterium with a labeled ligand under conditions wherein the labeled ligand contacts the binding polypeptide;
  (d) selecting said bacterium based on the presence of said labeled ligand bound to said candidate binding polypeptide; and
  (e) cloning a nucleic acid sequence encoding said candidate binding polypeptide from said bacterium.

* * * * *

UNITED STATES PATENT AND TRADEMARK OFFICE
CERTIFICATE OF CORRECTION

PATENT NO. : 7,094,571 B2
APPLICATION NO. : 10/620278
DATED : August 22, 2006
INVENTOR(S) : Harvey et al.

It is certified that error appears in the above-identified patent and that said Letters Patent is hereby corrected as shown below:

Column 71, line 8, delete "sequence as" and insert --sequence is-- therefor.

Column 72, line 27, delete "heating" and insert --treating-- therefor.

Column 72, line 67, delete "ThuD" and insert --FhuD-- therefor.

Column 73, line 2, delete "Pod" and insert --PotI-- therefor.

Column 73, line 3, delete "TouB" and insert --TonB-- therefor.

Column 73, line 19, delete "FAGS" and insert --FACS-- therefor.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,094,571 B2 |
| APPLICATION NO. | : 10/620278 |
| DATED | : August 22, 2006 |
| INVENTOR(S) | : Barrett R. Harvey et al. |

It is certified that error appears in the above-identified patent and that said Letters Patent is hereby corrected as shown below:

In column 1, lines 10-14, delete
"The government may own rights in the present invention pursuant to the U.S. Army ARO MURI program and the Texas Consortium for Development of Biological Sensors and in connection with contract number DADD17-01-D-0001 with the U.S. Army Research Laboratory"
and insert
--This invention was made with government support under contract number DAAD19-99-1-0207 awarded by the Army Research Office, and contract number DAAD17-01-D-0001 awarded by the Army Research Laboratory. The government has certain rights in the invention. -- therefor.

Signed and Sealed this

Twenty-second Day of December, 2009

David J. Kappos
*Director of the United States Patent and Trademark Office*